United States Patent
Allen

(10) Patent No.: US 11,123,482 B2
(45) Date of Patent: Sep. 21, 2021

(54) DEVICE AND METHODS FOR TRANSVASCULAR TUMOR EMBOLIZATION

(71) Applicant: Embolx, Inc., Sunnyvale, CA (US)

(72) Inventor: Michael P. Allen, Los Altos, CA (US)

(73) Assignee: Embolx, Inc., Sunnyvale, CA (US)

( * ) Notice: Subject to any disclaimer, the term of this patent is extended or adjusted under 35 U.S.C. 154(b) by 133 days.

(21) Appl. No.: 16/196,398

(22) Filed: Nov. 20, 2018

(65) Prior Publication Data
US 2019/0083705 A1   Mar. 21, 2019

Related U.S. Application Data

(60) Continuation of application No. 14/954,699, filed on Nov. 30, 2015, now Pat. No. 10,130,762, which is a
(Continued)

(51) Int. Cl.
*A61M 29/00* (2006.01)
*A61M 31/00* (2006.01)
(Continued)

(52) U.S. Cl.
CPC ......... *A61M 5/16804* (2013.01); *A61B 17/12* (2013.01); *A61B 17/1204* (2013.01);
(Continued)

(58) Field of Classification Search
CPC .... A61B 17/12136; A61M 2025/0002; A61M 2025/0003; A61M 2025/105;
(Continued)

(56) References Cited

U.S. PATENT DOCUMENTS 4,198,981 A * 4/1980 Sinnreich ............... A61B 17/42
604/101.05
4,545,390 A   10/1985 Leary
(Continued)

FOREIGN PATENT DOCUMENTS

CN   101400400 A   4/2009
CN   102802698 A   11/2012
(Continued)

OTHER PUBLICATIONS

Cook Medical; Flexor technology; 16 pages; retrieved from the internet (https:cookmedical.com/data/resources/PI-BM-KCF-EN-201302_WEB.pdf) on May 5, 2019.
(Continued)

*Primary Examiner* — Rebecca E Eisenberg
(74) *Attorney, Agent, or Firm* — Shay Glenn LLP; Thomas M. Zlogar

(57) ABSTRACT

A method of embolizing a tumor includes advancing a distal end of a device having a catheter body and an occlusion structure to a target tumor site within a blood vessel of a body. The occlusion structure is activated within the blood vessel, and a real time pressure measurement in the vascular space distal to the activated occlusion structure is monitored. The method further includes waiting for a pressure drop in the vascular space distal to the activated occlusion structure and for the pressure drop to cause a blood flow reversal in branch vessels antegrade to the occlusion. An embolic substance is injected from the distal end of the delivery device to permit the reversed blood flow to carry the embolic substance into the vasculature of the target tumor and the device is withdrawn from the body. Other catheter assemblies and methods of use are also disclosed.

9 Claims, 47 Drawing Sheets

Related U.S. Application Data division of application No. 14/273,445, filed on May 8, 2014, now Pat. No. 9,205,226.

(60) Provisional application No. 61/821,058, filed on May 8, 2013, provisional application No. 61/915,425, filed on Dec. 12, 2013, provisional application No. 61/917,131, filed on Dec. 17, 2013.

(51) Int. Cl.
| | |
|---|---|
| *A61M 37/00* | (2006.01) |
| *A61M 5/168* | (2006.01) |
| *A61B 17/12* | (2006.01) |
| *A61M 5/172* | (2006.01) |
| *A61M 25/00* | (2006.01) |
| *A61M 25/10* | (2013.01) |

(52) U.S. Cl.
CPC .......... *A61M 5/172* (2013.01); *A61M 5/1723* (2013.01); *A61M 25/00* (2013.01); *A61M 25/0068* (2013.01); *A61M 25/0069* (2013.01); *A61M 25/0075* (2013.01); *A61M 25/10* (2013.01); *A61M 25/1025* (2013.01); *A61B 17/12109* (2013.01); *A61B 17/12136* (2013.01); *A61M 25/1002* (2013.01); *A61M 2005/1726* (2013.01); *A61M 2025/0001* (2013.01); *A61M 2025/0002* (2013.01); *A61M 2025/0003* (2013.01); *A61M 2025/0076* (2013.01); *A61M 2025/105* (2013.01); *A61M 2025/109* (2013.01); *A61M 2025/1052* (2013.01); *A61M 2025/1061* (2013.01); *A61M 2025/1081* (2013.01); *A61M 2025/1093* (2013.01); *A61M 2025/1097* (2013.01); *A61M 2210/12* (2013.01)

(58) Field of Classification Search
CPC .... A61M 2025/1052; A61M 2025/109; A61M 2025/1093; A61M 2025/1097; A61M 25/10; A61M 25/1002; A61M 5/16804
See application file for complete search history.

(56) References Cited

U.S. PATENT DOCUMENTS

| | | |
|---|---|---|
| 4,581,017 A | 4/1986 | Sahota |
| 4,737,153 A | 4/1988 | Shimamura et al. |
| 4,748,982 A | 6/1988 | Horzewski et al. |
| 4,892,519 A | 1/1990 | Songer et al. |
| 4,896,669 A | 1/1990 | Bhate et al. |
| 4,909,252 A | 3/1990 | Goldberger |
| 4,944,745 A | 7/1990 | Sogard et al. |
| 4,976,690 A | 12/1990 | Solar et al. |
| 4,990,143 A | 2/1991 | Sheridan |
| 5,000,734 A | 3/1991 | Boussignac et al. |
| 5,040,548 A | 8/1991 | Yock |
| 5,045,072 A | 9/1991 | Castillo et al. |
| 5,047,045 A | 9/1991 | Arney et al. |
| 5,078,685 A | 1/1992 | Colliver |
| 5,090,958 A | 2/1992 | Sahota |
| 5,100,386 A | 3/1992 | Inoue |
| 5,137,513 A | 8/1992 | Mcinnes et al. |
| 5,156,594 A | 10/1992 | Keith et al. |
| 5,217,434 A | 6/1993 | Arney |
| 5,234,416 A | 8/1993 | Macaulay et al. |
| 5,279,562 A | 1/1994 | Sirhan et al. |
| 5,334,154 A | 8/1994 | Samson et al. |
| 5,342,386 A | 8/1994 | Trotta |
| 5,356,388 A | 10/1994 | Sepetka et al. |
| 5,370,655 A | 12/1994 | Burns |
| 5,423,754 A | 6/1995 | Cornelius et al. |
| 5,423,829 A | 6/1995 | Pham et al. |
| 5,429,605 A | 7/1995 | Richling |
| 5,454,795 A | 10/1995 | Samson |
| 5,470,314 A | 11/1995 | Walinsky |
| 5,484,409 A | 1/1996 | Atkinson et al. |
| 5,498,251 A | 3/1996 | Dalton |
| 5,501,667 A | 3/1996 | Verduin |
| 5,509,910 A | 4/1996 | Lunn |
| 5,556,383 A | 9/1996 | Wang et al. |
| 5,582,619 A | 12/1996 | Ken |
| 5,588,442 A | 12/1996 | Scovil et al. |
| 5,599,326 A | 2/1997 | Carter |
| 5,624,449 A | 4/1997 | Pham et al. |
| 5,643,254 A | 7/1997 | Scheldrup et al. |
| 5,647,198 A | 7/1997 | Mihailovic |
| 5,649,949 A | 7/1997 | Wallace et al. |
| 5,658,263 A | 8/1997 | Dang et al. |
| 5,669,905 A | 9/1997 | Scheldrup et al. |
| 5,674,198 A | 10/1997 | Leone |
| 5,690,666 A | 11/1997 | Berenstein et al. |
| 5,690,667 A | 11/1997 | Gia |
| 5,718,711 A | 2/1998 | Berenstein et al. |
| 5,722,424 A | 3/1998 | Engelson |
| 5,749,837 A | 5/1998 | Palermo et al. |
| 5,766,192 A | 6/1998 | Zacca |
| 5,769,830 A | 6/1998 | Parker |
| 5,775,327 A | 7/1998 | Randolph et al. |
| 5,792,300 A | 8/1998 | Inderbitzen et al. |
| 5,797,874 A | 8/1998 | Spears |
| 5,800,454 A | 9/1998 | Jacobsen et al. |
| 5,807,355 A | 9/1998 | Ramzipoor et al. |
| 5,820,592 A | 10/1998 | Hammerslag |
| 5,830,182 A | 11/1998 | Wang et al. |
| 5,833,705 A | 11/1998 | Ken et al. |
| 5,843,032 A | 12/1998 | Kastenhofer |
| 5,843,050 A | 12/1998 | Jones et al. |
| 5,851,203 A | 12/1998 | Van Muiden |
| 5,853,418 A | 12/1998 | Ken et al. |
| 5,891,128 A | 4/1999 | Gia et al. |
| 5,911,717 A | 6/1999 | Jacobsen et al. |
| 5,951,539 A | 9/1999 | Nita et al. |
| 5,951,929 A | 9/1999 | Wilson |
| 5,984,878 A | 11/1999 | Engelson |
| 5,984,929 A | 11/1999 | Bashiri et al. |
| 6,013,084 A | 1/2000 | Ken et al. |
| 6,014,919 A | 1/2000 | Jacobsen et al. |
| 6,019,757 A | 2/2000 | Scheldrup |
| 6,022,340 A | 2/2000 | Sepetka et al. |
| 6,036,382 A | 3/2000 | Lange et al. |
| 6,036,670 A | 3/2000 | Wijeratne et al. |
| 6,036,682 A | 3/2000 | Lange et al. |
| 6,066,157 A | 5/2000 | Barbere |
| 6,066,667 A | 5/2000 | Ashbrook |
| 6,071,286 A | 6/2000 | Mawad |
| 6,090,099 A | 7/2000 | Samson et al. |
| 6,123,714 A | 9/2000 | Gia et al. |
| 6,156,061 A | 12/2000 | Wallace et al. |
| 6,165,163 A | 12/2000 | Chien et al. |
| 6,187,027 B1 | 2/2001 | Mariant et al. |
| 6,190,358 B1 | 2/2001 | Fitzmaurice et al. |
| 6,190,393 B1 | 2/2001 | Bevier et al. |
| 6,203,547 B1 | 3/2001 | Nguyen et al. |
| 6,258,080 B1 | 7/2001 | Samson |
| 6,270,495 B1 | 8/2001 | Palermo |
| 6,280,457 B1 | 8/2001 | Wallace et al. |
| 6,287,301 B1 | 9/2001 | Thompson et al. |
| 6,319,228 B1 | 11/2001 | Kastenhofer |
| 6,344,041 B1 | 2/2002 | Kupiecki et al. |
| 6,397,850 B1 | 6/2002 | Scheldrup et al. |
| 6,423,085 B1 | 7/2002 | Murayama et al. |
| 6,428,489 B1 | 8/2002 | Jacobsen et al. |
| 6,440,088 B1 | 8/2002 | Jacobsen et al. |
| 6,468,266 B1 | 10/2002 | Bashiri et al. |
| 6,471,673 B1 | 10/2002 | Kastenhofer |
| 6,508,804 B2 | 1/2003 | Sarge et al. |
| 6,553,880 B2 | 4/2003 | Jacobsen et al. |
| 6,575,959 B1 | 6/2003 | Sarge et al. |
| 6,579,246 B2 | 6/2003 | Jacobsen et al. |
| 6,635,069 B1 | 10/2003 | Teoh et al. |
| 6,638,245 B2 | 10/2003 | Miller et al. |
| 6,652,508 B2 | 11/2003 | Griffin et al. |

(56) References Cited

U.S. PATENT DOCUMENTS

| | | |
|---|---|---|
| 6,656,550 B1 | 12/2003 | Zamore |
| 6,702,782 B2 | 3/2004 | Miller et al. |
| 6,702,802 B1 | 3/2004 | Hancock et al. |
| 6,706,025 B2 | 3/2004 | Engelson et al. |
| 6,766,720 B1 | 7/2004 | Jacobsen et al. |
| 6,780,181 B2 | 8/2004 | Kroll et al. |
| 6,835,189 B2 | 12/2004 | Musbach et al. |
| 6,860,893 B2 | 3/2005 | Wallace et al. |
| 6,860,899 B1 | 3/2005 | Rivelli |
| 6,878,151 B2 | 4/2005 | Garrison et al. |
| 6,921,410 B2 | 7/2005 | Porter |
| 6,936,055 B1 | 8/2005 | Ken et al. |
| 6,997,937 B2 | 2/2006 | Jacobsen et al. |
| 7,004,962 B2 | 2/2006 | Stinson |
| 7,037,330 B1 | 5/2006 | Rivelli et al. |
| 7,060,083 B2 | 6/2006 | Gerberding |
| 7,070,607 B2 | 7/2006 | Murayama et al. |
| 7,144,407 B1 | 12/2006 | Lasersohn |
| 7,153,323 B1 | 12/2006 | Teoh et al. |
| 7,166,122 B2 | 1/2007 | Aganon et al. |
| 7,294,137 B2 | 11/2007 | Rivelli et al. |
| 7,332,689 B2 | 2/2008 | Mertens et al. |
| 7,412,285 B2 | 8/2008 | Schroeppel et al. |
| 7,468,070 B2 | 12/2008 | Henry et al. |
| 7,481,800 B2 | 1/2009 | Jacques |
| 7,621,904 B2 | 11/2009 | McFerran et al. |
| 7,645,259 B2 | 1/2010 | Goldman |
| 7,654,979 B2 | 2/2010 | Simpson |
| 7,742,811 B2 | 6/2010 | Schroeppel et al. |
| 7,780,626 B2 | 8/2010 | Wu et al. |
| 7,942,847 B2 | 5/2011 | Stupecky et al. |
| 7,998,165 B2 | 8/2011 | Huffmaster |
| 8,066,667 B2 | 11/2011 | Hayman et al. |
| 8,092,508 B2 | 1/2012 | Leynov et al. |
| 8,202,292 B2 | 6/2012 | Kellett |
| 8,206,373 B2 | 6/2012 | Zhou |
| 8,348,890 B2 | 1/2013 | Gerrans et al. |
| 8,961,550 B2 | 2/2015 | Lenker et al. |
| 9,174,020 B2 | 11/2015 | Allen et al. |
| 9,205,226 B2 | 12/2015 | Allen et al. |
| 9,427,550 B2 | 8/2016 | Dakin et al. |
| 9,550,046 B1 | 1/2017 | Allen |
| 9,555,165 B2 | 1/2017 | Phan |
| 9,844,383 B2 | 12/2017 | Allen |
| 10,086,174 B2 | 10/2018 | Crall et al. |
| 10,130,762 B2 | 11/2018 | Allen |
| 2001/0041862 A1 | 11/2001 | Glickman |
| 2002/0032457 A1 | 3/2002 | Sirhan et al. |
| 2003/0050600 A1 | 3/2003 | Ressemann et al. |
| 2003/0114878 A1 | 6/2003 | Diederich et al. |
| 2003/0144657 A1 | 7/2003 | Bowe et al. |
| 2003/0191435 A1 | 10/2003 | Shkolnik |
| 2003/0199914 A1 | 10/2003 | Diaz |
| 2004/0073158 A1 | 4/2004 | Shah et al. |
| 2004/0167415 A1* | 8/2004 | Gelfand ........... A61B 17/12136 600/500 |
| 2005/0131453 A1 | 6/2005 | Parodi |
| 2005/0267407 A1 | 12/2005 | Goldman |
| 2006/0106413 A1 | 5/2006 | Bence et al. |
| 2006/0149186 A1 | 7/2006 | Wantink et al. |
| 2006/0276886 A1 | 12/2006 | George et al. |
| 2007/0088380 A1 | 4/2007 | Hirszowicz et al. |
| 2007/0137651 A1 | 6/2007 | Glassenberg et al. |
| 2007/0149927 A1 | 6/2007 | Itou et al. |
| 2008/0045908 A1 | 2/2008 | Gould et al. |
| 2008/0208118 A1 | 8/2008 | Goldman |
| 2008/0262470 A1 | 10/2008 | Lee et al. |
| 2009/0131831 A1 | 5/2009 | Wright et al. |
| 2009/0156999 A1 | 6/2009 | Adams et al. |
| 2009/0177183 A1 | 7/2009 | Pinkernell et al. |
| 2010/0030200 A1 | 2/2010 | Strauss et al. |
| 2010/0113939 A1 | 5/2010 | Mashimo et al. |
| 2010/0222637 A1 | 9/2010 | Kassab |
| 2010/0249491 A1 | 9/2010 | Farnan et al. |
| 2012/0203173 A1 | 8/2012 | Davies et al. |
| 2012/0253447 A1 | 10/2012 | Hayasaka et al. |
| 2013/0131610 A1 | 5/2013 | Dewaele et al. |
| 2014/0163421 A1 | 6/2014 | Van Hoven |
| 2014/0371709 A1 | 12/2014 | Allen et al. |
| 2014/0371718 A1 | 12/2014 | Alvarez et al. |
| 2015/0112255 A1 | 4/2015 | Jensen et al. |
| 2015/0351729 A1 | 12/2015 | Chin et al. |
| 2016/0008585 A1 | 1/2016 | Tano |
| 2016/0213893 A1 | 7/2016 | Franklin |
| 2017/0049495 A1 | 2/2017 | Yu et al. |
| 2018/0125502 A1 | 5/2018 | Allen |
| 2019/0329007 A1 | 10/2019 | Allen et al. |
| 2020/0297351 A1 | 9/2020 | Allen |

FOREIGN PATENT DOCUMENTS

| | | |
|---|---|---|
| CN | 102805893 A | 12/2012 |
| EP | 1131126 B1 | 8/2004 |
| EP | 2389968 A2 | 11/2011 |
| JP | H03-207376 A | 9/1991 |
| JP | H05-15604 A | 1/1993 |
| JP | H06-277296 A | 10/1994 |
| JP | H07-213617 A | 8/1995 |
| JP | 2003500121 A | 1/2003 |
| JP | 2005511108 A | 4/2005 |
| JP | 2006511271 A | 4/2006 |
| JP | 2007319468 A | 12/2007 |
| JP | 2008522716 A | 7/2008 |
| JP | 2008544801 A | 12/2008 |
| JP | 2011152181 A | 8/2011 |
| WO | WO89/08471 A1 | 9/1989 |
| WO | WO2004/107965 A2 | 12/2004 |
| WO | WO2012/009486 A2 | 1/2012 |
| WO | WO2012/099979 A1 | 7/2012 |
| WO | WO2014/008489 A1 | 1/2014 |

OTHER PUBLICATIONS

Halstead et al.; U.S. Appl. No. 16/545,519 entitled "Balloon catheters and methods of manufacture and use," filed Aug. 20, 2019.
Angiodynamics; Soft-vu angiographic catheters; 2 pages; retrieved from the internet (http://www.angiodynamics.com/products/soft-vu) on Aug. 17, 2018.
BMI ESPICOM Pharmaceutical and Medical Device News; Business Monitor Online: Vascular solutions expands complex intervention offerings with turnpike LP catheter; newsleter; 2pages; retrieved from the internet (https://dialog.proquest.com/professional/docview/1753127273?accountid=157282) on Apr. 18, 2018 (Abstract Only).
Cliffton et al.; Technique for visualization and perfusion of bronchial arteries: suggested clinical and diagnostic applications; Cancer; 16; pp. 444-452; Apr. 1963.
Matsuda et al.; Electrospinning fabrication of high-trackable catheter tip with gradually graded or gradient flexibility; J. Biomed. Mater. Res. B Appl. Biomater.; 1(35); pp. 35-41 doi: 10.1002/jbm.b.31061; (Abstract Only); Oct. 2008.
Nordson Medical; Extruded tubing technical information; 7 pages; retrieved from the internet (https://www.nordsonmedical.com/Components-and-Technologies/Medical-Tubing/Extruded-Tubing/Technical-Information/) on Aug. 17, 2018.
Rousselot et al.; Selective concentration of anticancer drugs in the liver: Hepatic-artery infusion and induced hepatic outflow block; JAMA; 191(9); pp. 707-710; Mar. 1965.
Vante Plasticweld Systems; Bonds and welds; 13 pages; retrieved from the internet (https://cathetertipping.com/home/our-products/bonding/) on Aug. 17, 2018.
Worldwide Videotex; Angiodynamics PCTA balloon catheter gets FDA market clearance; Biotech Equipment Update 5.9: N/A. Worldwide Videotex; Sep. 1, 1997; 2 pages; retrieved from the internet (https://dialog.proquest.com/professional/docview/680080033?accountid=157282) on Apr. 18, 2018 (Abstract Only).
Zeus; FluoroPEELZ peelable heat shrink; 9 pages; retrieved from the internet (https://www.zeusinc.com/products/heat-shrinkable-tubing/fluoropeelz-peelable-heat-shrink) on Aug. 17, 2018.
Allen et al.; U.S. Appl. No. 15/413,262 entitled "Balloon catheter and methods of fabrication and use," filed Jan. 23, 2017.

(56) References Cited

OTHER PUBLICATIONS

Halstead et al.; U.S. Appl. No. 16/004,247 entitled "High torque catheter and methods of manufacture," filed Jun. 8, 2018.
Halstead et al.; U.S. Appl. No. 16/047,922 entitled "Shaped catheter tip for tracking over a guidewire through turns in the vasculature," filed Jul. 27, 2018.

\* cited by examiner

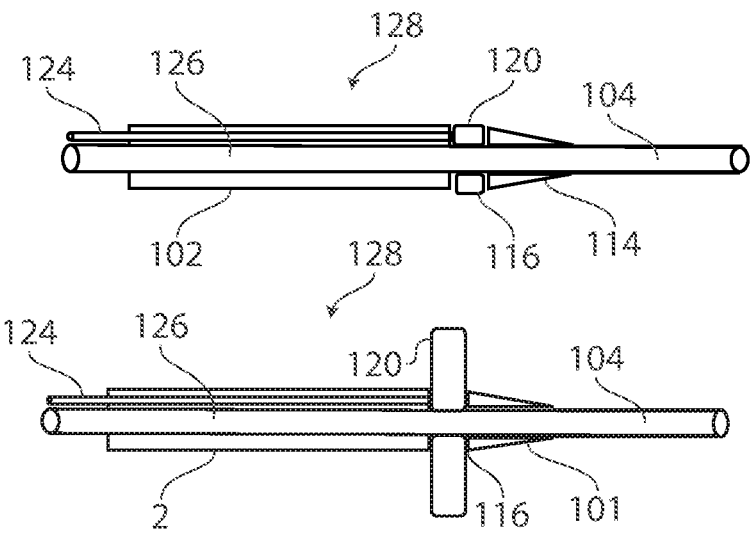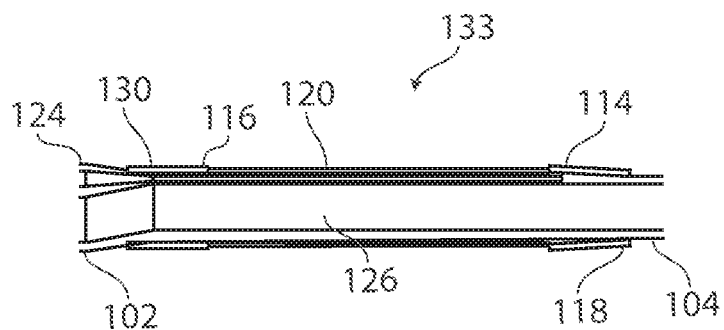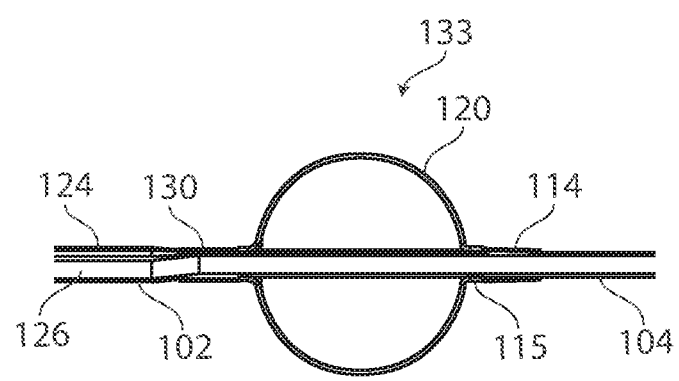

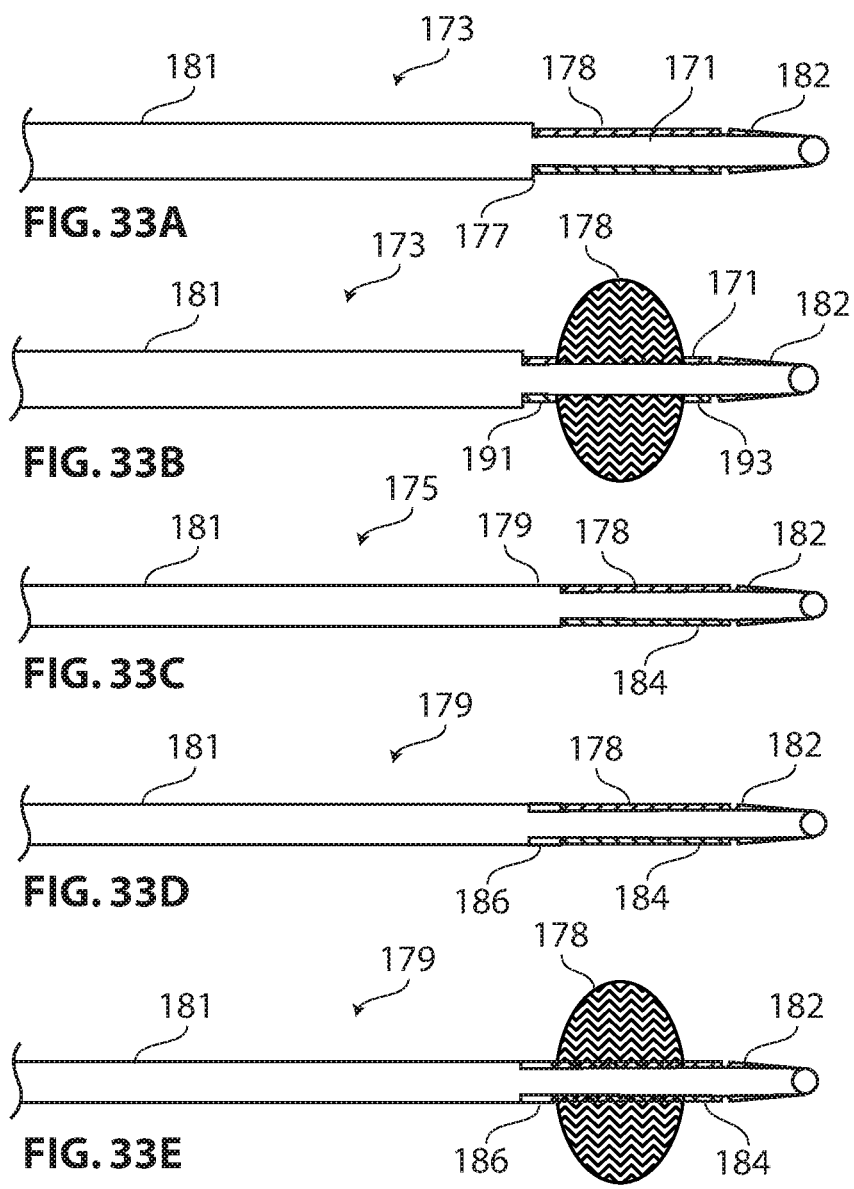

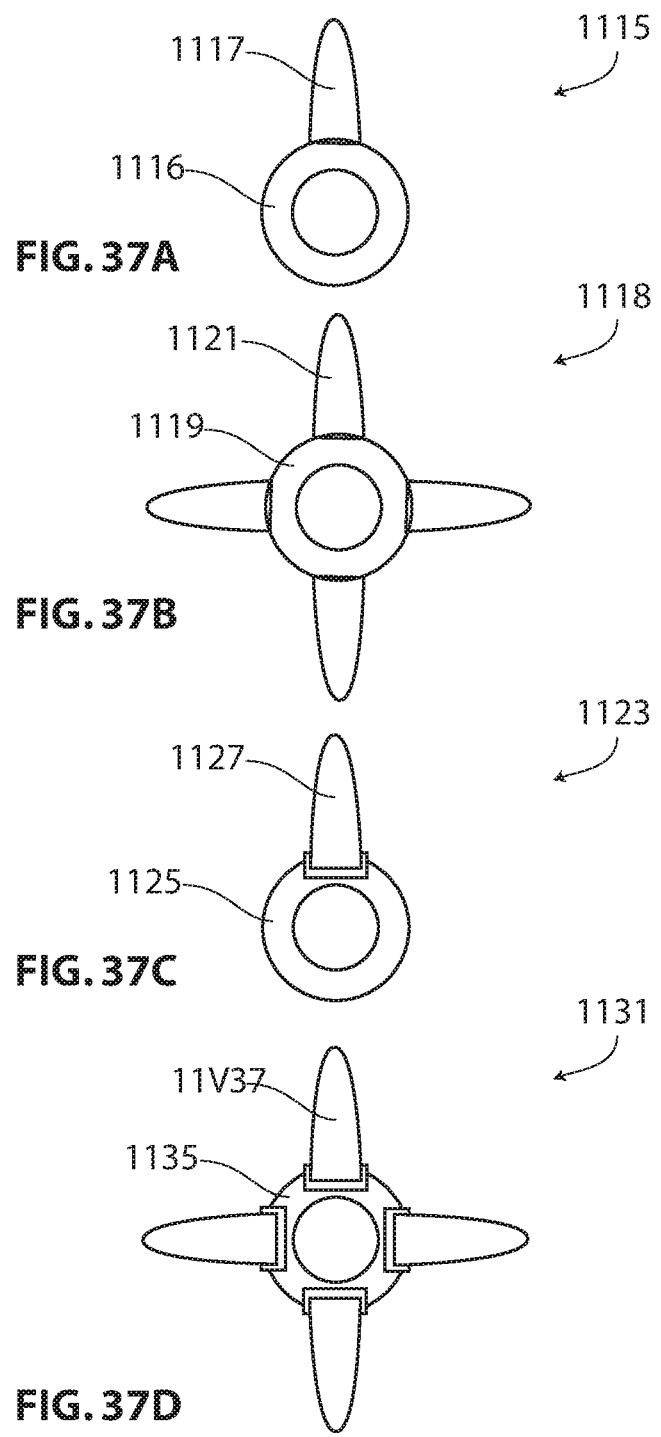

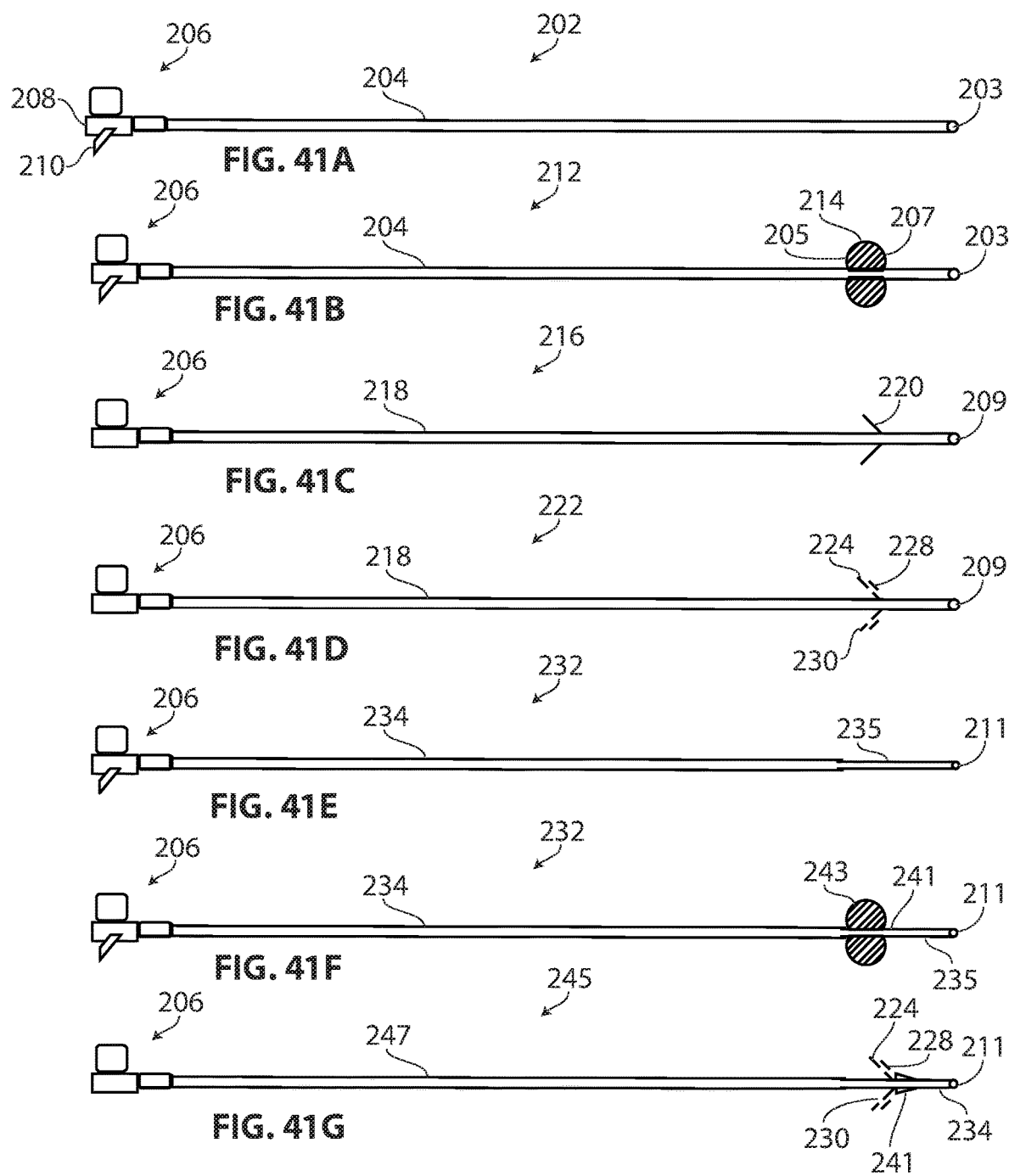

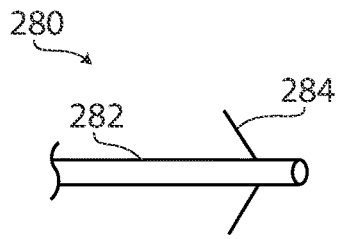
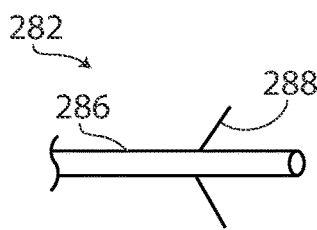
FIG. 45A  FIG. 45B
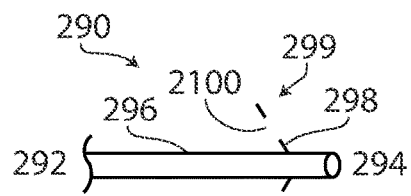
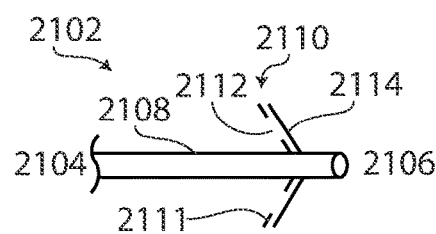
FIG. 46A  FIG. 46B
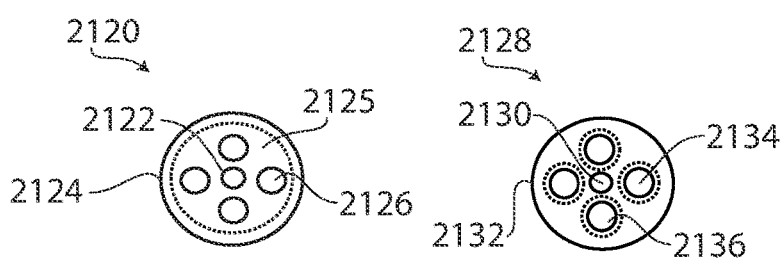
FIG. 47A  FIG. 47B
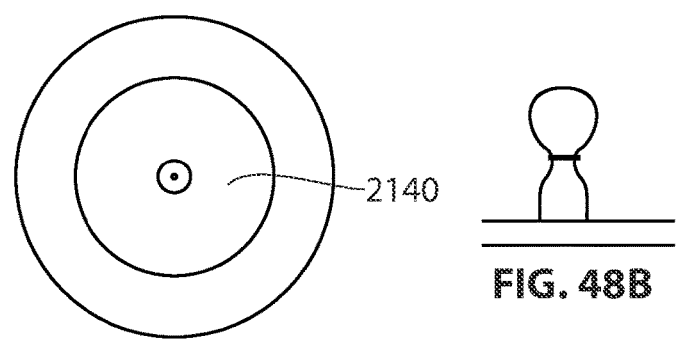
FIG. 48A  FIG. 48B

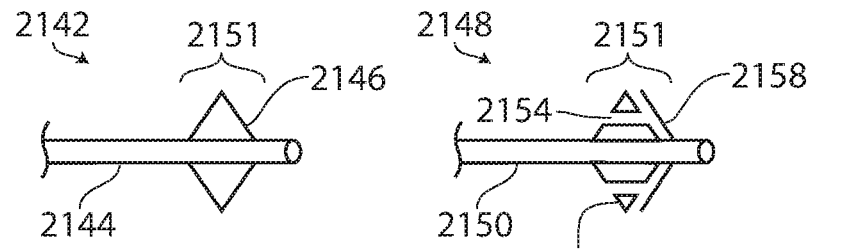
FIG. 49A
FIG. 49B
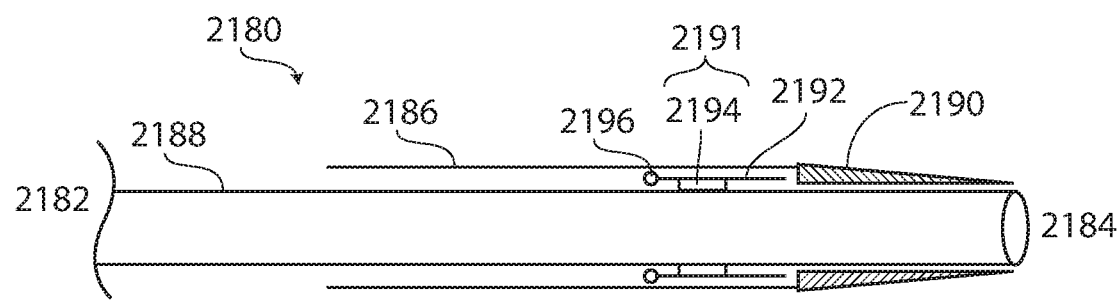
FIG. 50A
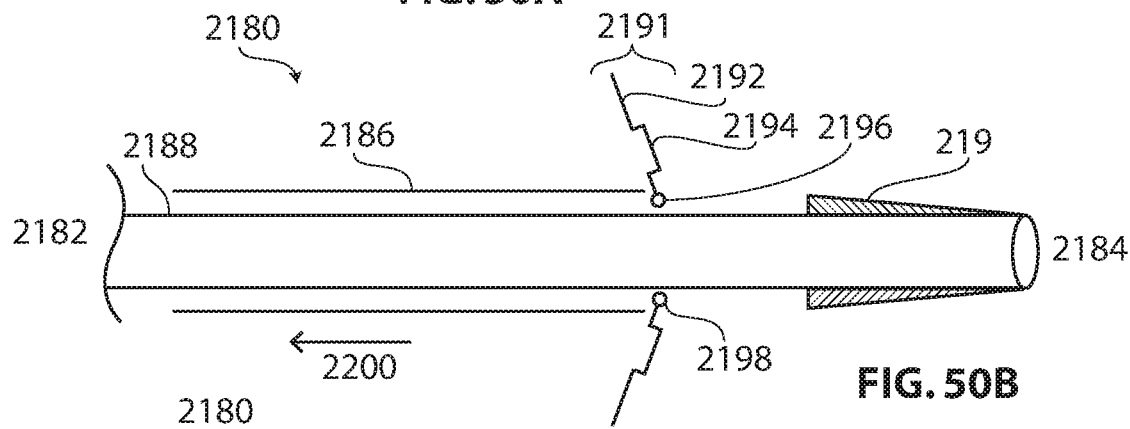
FIG. 50B
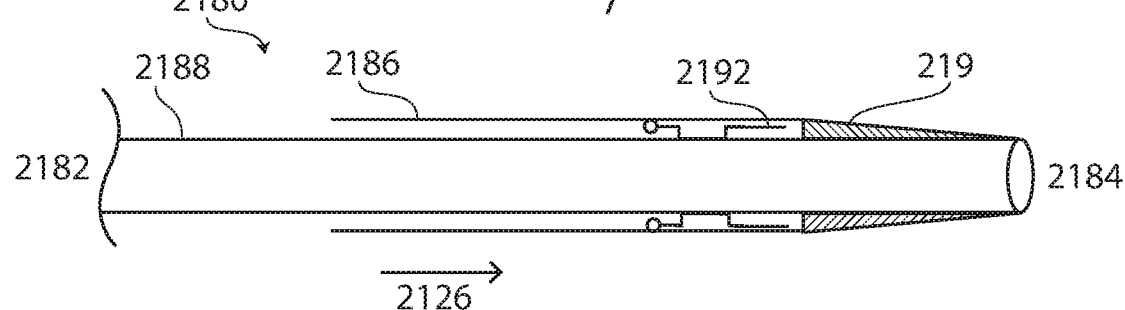
FIG. 50C

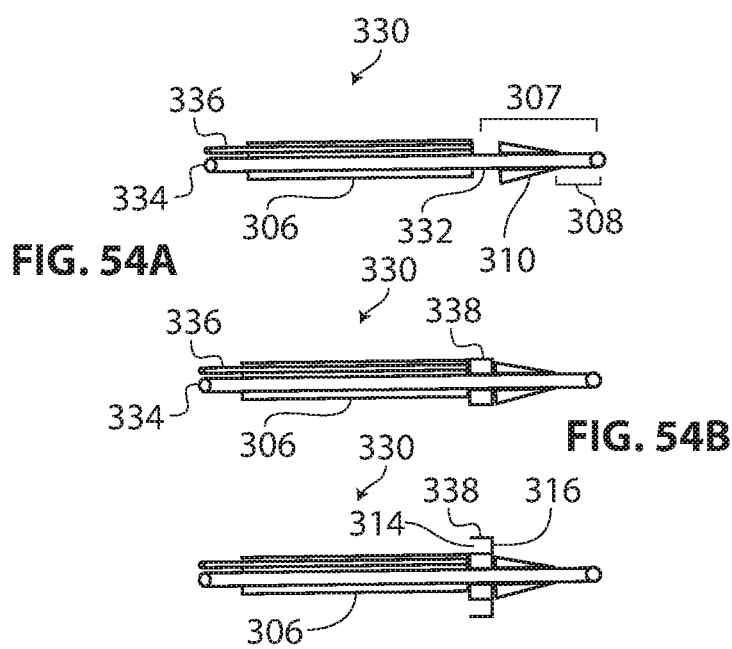
FIG. 54A
FIG. 54B
FIG. 54C
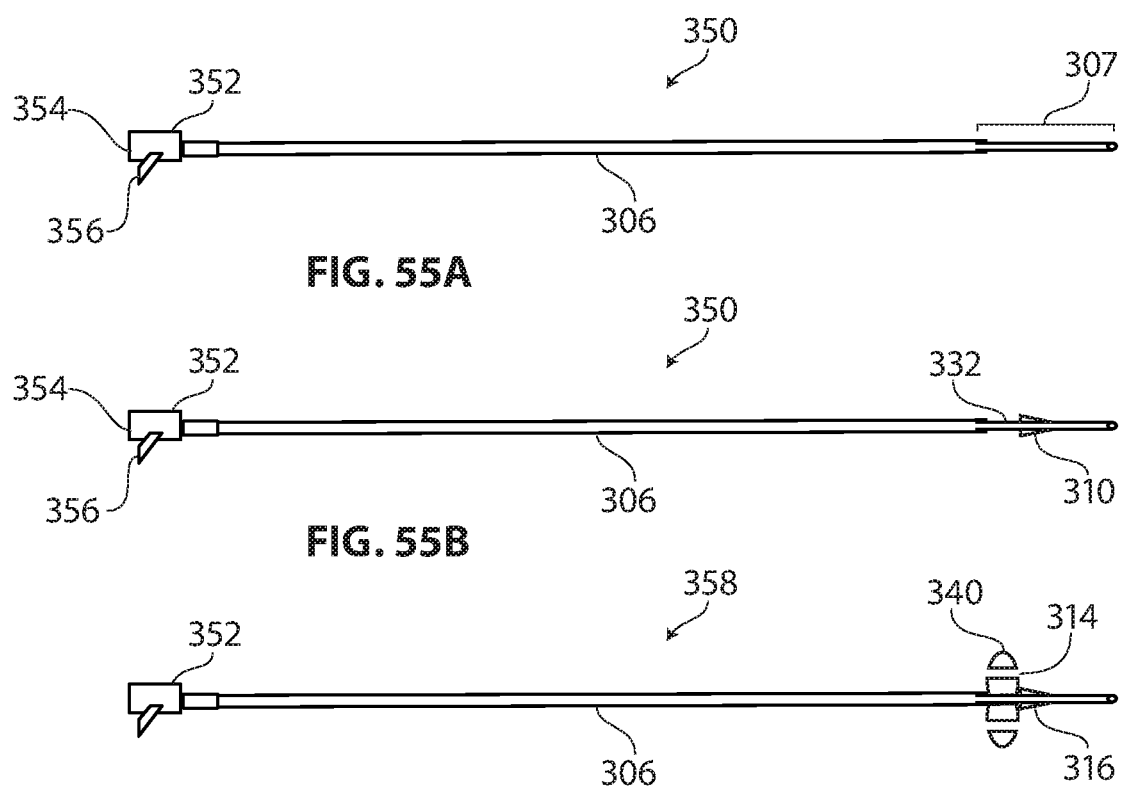
FIG. 55A
FIG. 55B
FIG. 55C

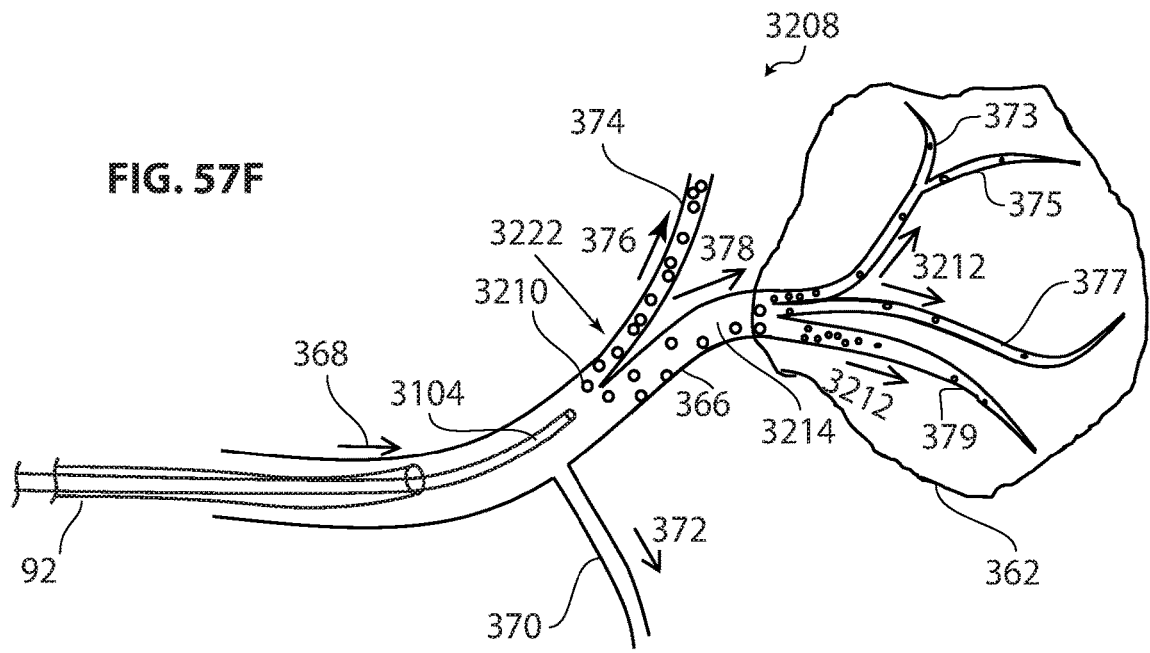
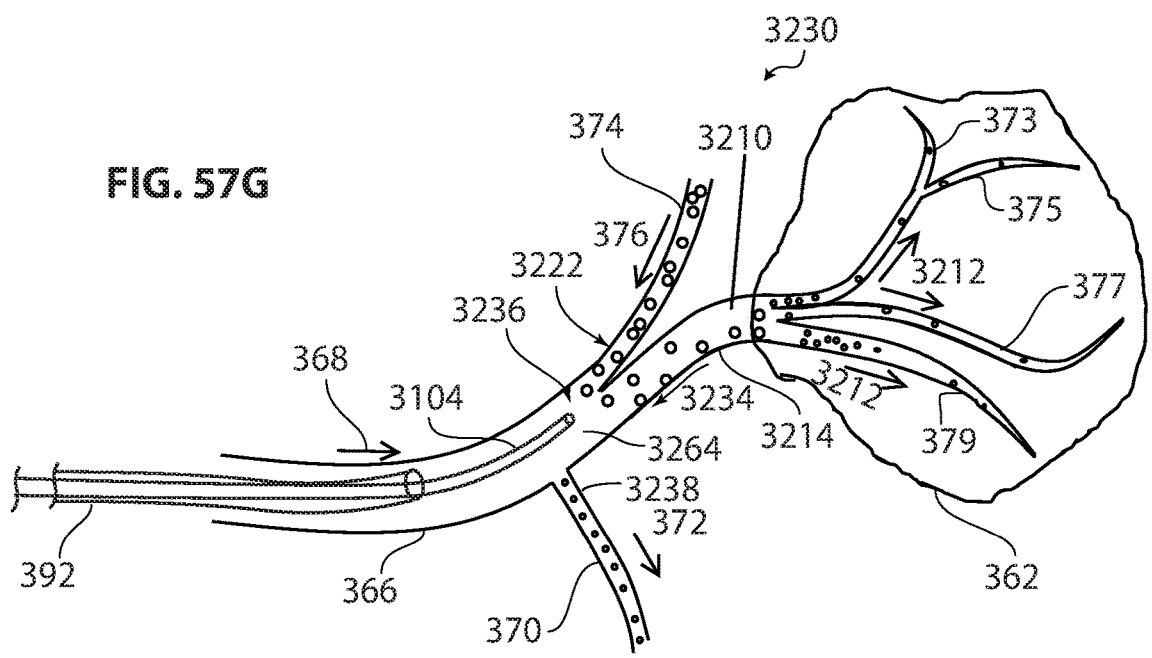

DEVICE AND METHODS FOR TRANSVASCULAR TUMOR EMBOLIZATION

CROSS REFERENCE TO RELATED APPLICATIONS

This application is a continuation of U.S. patent application Ser. No. 14/954,699, filed Nov. 30, 2015, now U.S. Pat. No. 10,130,762, which is a divisional of U.S. application Ser. No. 14/273,445 filed May 8, 2014, now U.S. Pat. No. 9,205,226, which claims the benefit of U.S. Provisional Patent Application No. 61/821,058 filed May 8, 2013, U.S. Provisional Patent Application No. 61/915,425 filed Dec. 12, 2013, and U.S. Provisional Patent Application No. 61/917,131 filed Dec. 17, 2013, each of which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

This application relates generally to medical methods and devices. More specifically, the present application discloses various embodiments of occlusion devices adapted to a catheter, and methods for their use in delivering fluids, embolic materials and other therapeutic agents to sites within the body.

BACKGROUND

There are over one million cases of cancer diagnosed each year in the United States and numerous approaches of therapy including systemic chemotherapy, radiation and surgical resection. Given that systemic chemotherapy and radiation interact with healthy tissue, complications and toxicity often result. Targeted drugs are now being used and produce a lower rate of complications. Ablative approaches, including microwave, radiofrequency and cryogenic therapies have been used; however, these methods are often not selective and tissues and organs surrounding or below the tumor can be affected.

According to the National Institute of Health, 30,640 people were diagnosed with primary liver cancer (hepatocellular carcinoma, HCC) and 142,820 people were diagnosed with colorectal cancer in the U.S. in 2013. Seventy-five percent of these will metastasize to the liver. Liver resection and transplant are the only curative means; however, only small numbers of patients are eligible. Systemic chemotherapy for primary and metastatic tumors in the liver is ineffective, having a response rate of about 20% and a survival benefit of 10.7 months vs. 7.9 months over symptomatic care.

Catheters are commonly used in medicine for delivery of fluids, therapeutics, and implants, and in sampling tissues and bodily fluids. Catheters can be constructed with balloons or other tools to dilate tissue, block fluid flow or isolate segments of the anatomy, such as in treatment of the cancers described above.

Trans-Arterial Embolization therapy is the transvascular injection of drug and/or embolic agents directly into the tumor vasculature using a microcatheter. Embolization therapy causes a shutdown of blood flow and, when drug or radioactivity is present, simultaneous release of high concentrations of drug or radioactivity. The technique is also noted for its very low level of toxicity.

In the early 1980's, transarterial chemoembolization (TACE) began to be used as a selective cancer therapy. In this method, chemotherapeutic and embolic agents are injected directly into the vasculature of the tumor, a technique that is most common for the treatment of hepatocellular carcinoma. More recently, transarterial radioembolization (TARE) has been used clinically. In this method, radioactive embolic particles, typically yttrium-90 (y90), are injected rather than chemotherapeutic agents. Although the liver is a common target for TACE and TARE, other organs, including, but not limited to, the pancreas, lung, kidney, prostate, stomach, colon and head and neck have been treated using these methods. Chemoembolization was established as a standard of care for intermediate stage hepatocellular carcinoma in 2006.

Numerous studies have demonstrated transarterial embolization to be effective on a number of primary cancers and to have better performance than chemotherapy for both HCC and metastatic colorectal cancers in the liver; however, studies show inconsistent outcomes with reported tumor responses from 15% to 85%. Although anatomical and individual differences are clearly of significance in between-patient variation, clinical studies, each of which include a range of patients, show very different outcomes, indicating that there currently is little procedural optimization or standardization.

The above procedures are accomplished by inserting a small catheter into the femoral artery at the groin and navigating it into the liver vasculature, typically the hepatic artery, then into the right or left lobe of the liver or more selectively into particular segments of the liver or super-selectively directly into or adjacent to the tumor. Super-selective transarterial delivery of antitumor agents into the tumor vasculature has become state-of-the-art and requires catheters that can reach into small vessels. Presently, standard microcatheters, typically at or about 3 Fr are used to inject antitumor agents into the target vasculature. These standard microcatheters rely on normal blood flow as the means by which the embolic agent moves into the tumor and systolic pressure as the packing force. However, the injection pressure is typically higher than the blood pressure and blood flow can be reversed. When this happens, the cancer agent flows in a retrograde direction with respect to normal blood flow and away from the tumor, with a concomitant risk of delivery of the anti-cancer therapy to organs that can be damaged by these toxic agents. This situation also results in loss of an unknown amount of drug.

The endpoint of the above procedures is determined by physicians' visual observation and can range between fully embolized to partially embolized with the amount of dose delivered being highly variable. Retrograde and anterograde reflux, distribution, packing, quantity of dose delivered and procedure endpoint are variables that can be highly dependent on the rate and pressure of injection, the selection of the type of endpoint, the patient's systolic pressure and the operator. As such, clinical trials using TACE to treat hepatocellular carcinoma have demonstrated wide variations in tumor response. The most significant problems that occur with the current means of delivery and methods of embolization therapy include inconsistent efficacy and non-target embolization.

Using standard straight-tip catheters, non-target embolization in the retrograde direction can be caused when the pressure of injection exceeds the systolic blood pressure and the embolic agents flow backwards over the catheter and into the general circulation. Anterograde reflux and non-target embolization occurs when the embolic agents flow into distal vasculature, through arteriovenous shunting and into the venous circulation. This can easily occur because venous blood pressure on average is about 10 to 15 mmHg as compared to arterial diastolic blood pressure of about 80 mmHg.

When therapeutic agents are delivered into the vasculature of a target structure using the normal anterograde blood flow to carry the therapy to the target, injection rate and pressure of the therapy must be carefully controlled in relation to the flow volume and pressure of blood to avoid retrograde reflux of drug backward over the catheter and into the general circulation. In particular, when injecting embolic agents into the vasculature of a tumor, pressure distal to the catheter tip continues to increase as embolization progresses, causing a resistance that prevents embolic agents from filling the target vasculature and the possibility of retrograde reflux and non-target embolization. It would be desirable to eliminate this retrograde reflux, non-target embolization, and the inconsistent dosages that are delivered to targets with current state of the art procedures. It would be further desirable to eliminate the low levels of particle distribution and density throughout the target vasculature. It would be still further desirable to replace current delivery devices that are not always capable of fully isolating the target vasculature and often do not allow the operator to control pressure, flow rate and other parameters associated with therapeutic delivery.

The present state-of-the-art embolization therapy for tumors in the liver relies on high volume forward flow from the hepatic artery to deliver embolization agents into the tumor. However; distal embolization of larger capillaries causes: (1) high intra-tumor vascular pressure, (2) high pressure in arteries feeding the tumor, (3) proximal reflux backwards over the delivery catheter, (4) increased anterograde bypass in distal hepatoenteric arteries and (5) poor filling and distribution of embolic agents in the tumor. This situation results in an uncontrollable number of particles entering the tumor and procedural high variability.

Problems with the current method of embolization therapy that cause inconsistent outcomes include: variable procedural endpoints, unknown quantity of dose delivered, reflux of embolization agents into the general circulation, anterograde bypass of embolization particles into the general circulation, non-target embolization, rising intra-tumor arterial pressures during the initial stages of embolization and catheter movement during injection. The current delivery catheters are unable to control many of the above mentioned variables, making any standardization of the current procedures difficult or impossible to achieve.

The following patents and published patent applications provide some examples of the current state of this art. U.S. Pat. No. 5,647,198 describes a catheter with a pair of spaced apart balloons that define an intra-balloon space. A lumen passes through the catheter and exits within the intra-balloon space allowing injection of drugs, emulsions, fluids and fluid/solid mixtures. A perfusion lumen or bypass extends from a location proximal to the proximal balloon and to the distal tip to allow shunting of blood past the inflated balloons. U.S. Pat. No. 5,674,198 describes a two balloon catheter that is designed for treating a solid tumor. The balloons are positioned to isolate the blood flow into the tumor and allow injection of a vaso-occlusive collagen material to block the tumor blood supply. Clifton et al. (1963) Cancer 16:444-452 describes a two balloon catheter for the treatment of lung carcinoma. The four lumen catheter includes a lumen for independent injection in the space between the balloons. Rousselot et al. (1965) JAMA 191: 707-710 describes a balloon catheter device for delivering anticancer drugs into the Liver. See also U.S. Pat. Nos. 6,780,181; 6,835,189; 7,144,407; 7,412,285; 7,481,800; 7,645,259; 7,742,811; U.S. App. No. 2001/008451; U.S. App. No. 2001/0041862; U.S. App. No. 2003/008726; U.S. App. No. 2003/0114878; U.S. App. No. 2005/0267407; U.S. App. No. 2007/0137651; U.S. App. No. 2008/0208118; U.S. App. No. 2009/0182227 and U.S. App. No. 2010/0114021.

What is needed and is not provided by the prior art is a delivery system and method that enable optimization and standardization of treatment delivery, such as by delivering a known quantity of embolic agent to a prescribed target area, and elimination of non-target embolization.

SUMMARY OF THE DISCLOSURE

According to aspects of the present disclosure, devices and methods are provided for partial occlusion with unidirectional bypass flow, designed to be adapted to a catheter for delivery of therapeutic agents to a target site within the body. Such delivery devices may be intended for any medical purpose, but the embodiments described herein are focused on devices intended for performing transarterial delivery of therapeutic agents to a target site within the body. The entry point for the delivery catheter can be any arterial access point, typically the femoral artery located at the groin. The target can be any structure; however, of particular interest are tumors, primary or metastatic, of any organ or tissue that is accessible by a microcatheter through the arterial system. Cancers of particular interest include, but are not limited to, primary and metastatic cancers in the liver, pancreas, colon, rectum, kidney, stomach, lung, bladder, head and neck and uterus. Procedures that can benefit from the access and delivery methods and devices of the present disclosure include, but are not limited to, transarterial chemoembolization using drug eluting beads (DEB TACE), transarterial chemoembolization using Lipiodol (Lipiodol TACE), transarterial radioembolization (TARE) and transarterial embolization (TAE). Other procedures which can benefit from methods and devices of the present disclosure include direct delivery of chemotherapy or targeted drugs to the site of the cancer, the general delivery of drugs, venous or arterial embolization or other substances to specific regions of the body and drainage or aspiration of fluid or tissue.

In some embodiments, microcatheter methods and devices disclosed herein create a partial occlusion (in the hepatic artery) with concomitant reduction of pressure and flow in the vascular compartment distal to the occlusion. This can: (1) eliminate proximal reflux, (2) reverse hepatoenteric arterial flow distal to the occlusion, (3) limit or stop anterograde bypass, (3) reduce flow rate into the tumor, (4) delay the onset of high intra-tumor pressure, (5) increase the extent of embolization and (6) enable a quantitative pressure measurement as an endpoint.

In some embodiments, the device includes an occlusion structure adapted to the distal section of a two lumen catheter, whereby the occlusion structure has one or more channels disposed from its proximal surface to its distal surface allowing flow therethrough. The channels are configured to permit a controllable arterial or venous flow which is less than the un-occluded flow of the artery or vein, and the channel(s) may have one-way valve(s) that allow flow in only one direction. The flow rate can be any amount as compared to the normal un-occluded flow rate from 0% flow up to 100% flow, most typically from 85% flow to 95% flow. The flow channels and/or valves can be configured so as to regulate flow and/or pressure from one side of the occlusion structure to the other. The flow and/or pressure regulation can be static or variable, permitting a single continuous flow rate or multiple flow rates that are pre-calibrated or adjusted by the operator. Of particular interest in some embodiments is arterial flow regulation to a constant flow rate that is pre-calibrated.

In some embodiments, the flow rate reduction results in a pressure drop in the vascular space distal to the partial occlusion. When this occurs, distal arterial side branches of the occluded artery that are flowing away from the occluded artery, and part of arterial networks, may reverse direction and begin to flow toward the occluded artery. By way of example, embolization of tumors in the right lobe of the liver are accessed by a catheter advanced through the right hepatic artery (RHA) and to the vicinity of the tumor. Typically, the catheter tip does not enter the tumor vasculature and remains proximal to the tumor and within the right hepatic artery or branch thereof. In this example, the artery feeding the tumor is typically a branch of the RHA. However, there other distal hepatoenteric arteries that branch from the RHA and flow away from the RHA and to the liver and gastrointestinal tract. In this instance, when using a standard straight catheter, injection of embolic agents from the distal tip of the catheter results in flow of embolic agents into both the tumor and side branch arteries causing antero-grade bypass and non-target embolization of the liver and gastrointestinal tract, a situation that causes toxicity and complications.

In some embodiments of the present disclosure, the blood pressure drop in the arterial space distal to the partial occlusion device causes the branch hepatoenteric arteries to reverse flow and now flow toward the tumor. This situation prevents anterograde bypass, reduces non-target embolization and focuses substantially all injected drug and/or embolic agents into the tumor.

In some embodiments of the present disclosure, a partial occlusion device comprises a balloon with flow regulating channels and one-way valves which, when inflated in an artery, permits limited anterograde flow from vascular space proximal to the partial occlusion to the vascular space distal to the partial occlusion and prevents retrograde flow. So constructed, the device will significantly reduce the hepatic arterial flow into the tumor which is the tumor's main source of blood flow. In this instance, injected anti-cancer agents will flow into the tumor at a significantly slower rate and delay the onset of a high pressure in tumor vessels and retrograde blood flow toward the catheter tip. This slower filling of the tumor will improve the amount and distribution of embolic agents in the tumor. The lower pressure distal to the occlusion will cause the reversal of flow in distal hepatoenteric arteries during embolization and limit antero-grade bypass, and the one-way valves will eliminate retrograde bypass of embolic agents into proximal branch arteries such as the gastroduodenal artery.

By isolating the distal arterial space that is adjacent to the tumor from the arterial blood supply, the device of the present disclosure enables pressure measurement to be used to signal a procedural endpoint at a predetermined pressure or pressures. By way of example, the endpoint of the procedure can occur at a point when systolic pressure (120 mmHg) is first reached or at a point when systolic pressure is stabilized, however any pressure, pressure profile or algorithm can be used to determine an endpoint of the procedure. Such a measurable endpoint can contribute to standardization of the procedure and improved efficacy.

The occlusion structure of the device of the present disclosure may be held within a pocket within the catheter such that the outer diameter of the radially constrained occlusion structure is approximately equal to or less than the outer diameter of the catheter as described in co-pending U.S. provisional patent applications 61/821,058, 61/915,425 and 61/917,131. The pocket can be a longitudinal space in the catheter and can be formed as a reduction in the catheter diameter of a defined length and a depth equal to or greater than the thickness of the occlusion structure in a radially constrained configuration. Alternately, a pocket can be formed using an extension projecting distally beyond the catheter body, the distal extension having a diameter smaller than the catheter body. In this instance, the distal end of the catheter pocket is defined by the proximal end of a nose-piece. In some embodiments, the nose-piece has a diameter equal to or less than the diameter of the catheter body and is positioned over the distal extension at a defined distance from the distal end of the catheter body.

The occlusion structure of devices of the present disclosure can be advanced in a radially constrained configuration, to at least the proximity of a target within the body and then placed in its radially expanded configuration. Alternately, the device can be pre-formed in a fully expanded configuration, adapted to the distal end of a catheter and delivered to the target site. The valves are typically configured to allow proximal to distal (anterograde) bypass flow; however the opposite is possible or the valves may be absent allowing two way flow.

In some embodiments, a catheter assembly may be provided with a catheter body and an inflatable balloon. The catheter body has a proximal end, a distal end and a balloon inflation lumen. The inflatable balloon is attachable to the distal end of the catheter body. The balloon has an inner surface that at least partially defines an interior volume. The balloon is configured such that the interior volume can be in fluid communication with the inflation lumen of the catheter body to inflate the balloon. The balloon also has a proximal surface and a distal surface. The balloon is provided with a channel that extends through the balloon. The channel is configured to provide fluid communication between the proximal surface of the balloon and the distal surface of the balloon.

In some embodiments, a device for delivering a therapeutic agent to a target site within a body is provided. The device comprises a catheter body having a proximal end, a distal end, a first axial lumen and a second axial lumen. The first axial lumen extends from the proximal end of the catheter body to the distal end of the catheter body and provides fluid communication therebetween. The second axial lumen extends from the proximal end of the catheter body to a more distal location on the catheter body. The device further comprises a balloon radially disposed near the distal end of the catheter body. The balloon has a proximal balloon surface, a distal balloon surface, a radially constrained configuration and a radially expanded configuration. The balloon is in fluid communication with the second axial lumen and has at least one channel extending from the proximal balloon surface to the distal balloon surface, thereby providing fluid communication therebetween. The device also comprises a balloon sheath, disposed over an outer surface of the balloon. The sheath has a proximal side and a distal side. The proximal side has an opening that is in alignment with a proximal end of the balloon channel. The distal side of the sheath extends over a distal end of the balloon channel. The distal side of the sheath is capable of deflecting distally when a distally directed fluid pressure is applied through the opening in the proximal side, through the balloon channel and against a proximal surface of the distal side of the sheath, thereby allowing fluid to pass through the balloon channel and into a vascular compartment distal to the balloon and the balloon sheath. The distal side of the sheath is also capable of deflecting proximally onto the distal balloon surface when a pressure is applied to the distal side of the sheath, thereby preventing proximally directed flow in the balloon channel.

In some embodiments, a method of embolizing a tumor is provided. The method comprises advancing a device including a catheter body and a partial occlusion structure to a target tumor site within the body, and allowing an anterograde blood flow past the partial occlusion structure. The allowed anterograde blood flow is less than a blood flow that would normally be present if the partial occlusion structure were not in place. The method further comprises injecting an embolic substance from the device to allow the anterograde blood flow to carry the embolic substance into a vasculature of the tumor target. The method also comprises monitoring a real time pressure measurement in a vascular space distal to the partial occlusion structure, signaling a procedural endpoint based on the monitoring of the pressure measurement, and withdrawing the device from the body.

While aspects of the present disclosure will be described with particular reference to delivery of chemotherapeutic agents, radiotherapeutic agents, embolic agents or combinations thereof into the vasculature that supplies blood to a tumor, the same principles apply to the delivery or aspiration of a variety of materials into or from other locations, and through other luminal structures in the body.

BRIEF DESCRIPTION OF THE DRAWINGS

The novel features of the disclosure are set forth with particularity in the claims that follow. A better understanding of the features and advantages of the present disclosure will be obtained by reference to the following detailed description that sets forth illustrative embodiments, in which the principles of the disclosure are utilized, and the accompanying drawings of which:

FIGS. 25A and 25B illustrate a cross sectional view of the distal portion of one embodiment of the device according to the present disclosure;

FIGS. 26A and 26B illustrate a view of an embodiment including an occlusion balloon concealed within pocket formed between proximal and distal surfaces;

FIGS. 33A, 33B, 33C, 33D and 33E illustrate a cross sectional view of a sequential construction of an embodiment of the present disclosure including a balloon pocket and separate nose cone;

FIGS. 37A, 37B, 37C and 37D illustrate an embodiment of the present disclosure with a balloon or balloons placed on the circumference of the catheter;

FIGS. 41A, 41B, 41C, 41D, 41E, 41F and 41G illustrate constructions of embodiments of the present disclosure;

FIGS. 45A and 45B illustrate embodiments of the present disclosure for complete occlusion;

FIGS. 46A and 46B illustrate an embodiment with bidirectional and unidirectional channels;

FIGS. 47A and 47B illustrate valve constructions of an embodiment of a unidirectional occlusion structure of the present disclosure;

FIGS. 48A and 48B show a prototype micro-valve;

FIGS. 49A and 49B show an alternate embodiment of an occlusion structure;

FIGS. 50A, 50B and 50C illustrate a method of operation of one embodiment of a unidirectional occlusion structure of the present disclosure;

FIGS. 54A, 54B and 54C illustrate a distal end construction including pocket, constrained balloon and expanded partial occlusion balloon with channels and valves in closed position;

FIGS. 55A, 55B and 55C illustrate a serial construction of a full length catheter device;

FIGS. 57A, 57B, 57C, 57D, 57E, 57F, 57G and 57H illustrate a tumor embolization method for a standard catheter;

DETAILED DESCRIPTION

The device of the present disclosure allows improved distribution of anti-cancer agents into target tumor vasculature by reducing arterial flow and pressure during drug and/or embolic agent injection. The present device reduces toxicity and complications by eliminating reflux of embolic materials and/or anti-cancer agents into proximal arterial branches and reduces or eliminates anterograde bypass of embolic materials and/or anticancer agents into distal arterial branches. Further, the present disclosure enables pressure measurement as a means to a quantitative endpoint of the procedure. Such a device can improve efficacy and reproducibility of the technique and reduce complications.

Figure 1:
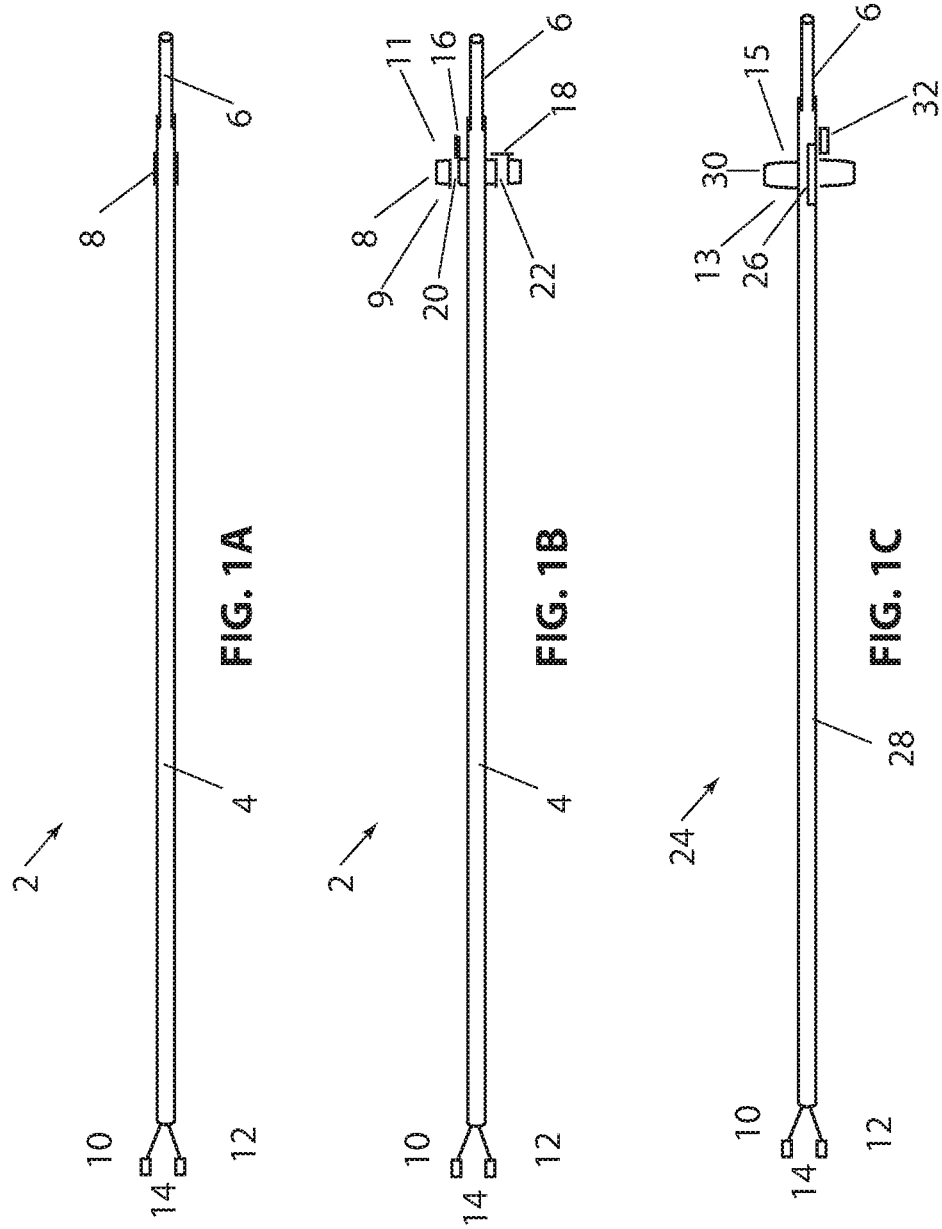
FIGS. 1A, 1B and 1C illustrate embodiments of the disclosure herein.

Referring to FIG. 1A, a longitudinal cross section of device 2 of the present disclosure is shown with catheter body 4, distal tip 6, balloon 8 (unexpanded configuration), balloon inflation tube 10, guidewire and injection tube 12 and fittings 14. Catheter body 4 can have a length of 10 cm to 400 cm, typically 60 cm to 250 cm and a diameter of 0.25 mm to 5 mm, typically 0.5 mm to 1.5 mm. Device 2 may or may not include a distal tip 6, the distal tip having a length of 1 mm to 50 mm, more typically from 5 mm to 30 mm. The balloon inflation tube 10, positioned at the proximal end of catheter body 4, is connected to, and in fluid communication with a balloon inflation lumen that runs longitudinally through the length of catheter body 4 and terminates at, and is in fluid communication with balloon 8. The guidewire and injection tube 12, positioned at the proximal end of catheter body 4, is connected to, and in fluid communication with a lumen that runs longitudinally through the length of catheter body 4 and terminates at the distal end or distal tip of catheter body 4, thereby allowing a guidewire to enter through fitting 14 and exit through the distal end of device 2 through catheter body 4. Fittings 14 are connected to each of balloon inflation tube 10 and guidewire and injection tube 12 and can connect to a syringe, inflation device or any other device or means to inject air, gas, fluid, suspensions, emulsions, contrast, therapeutic agents, embolic agents or any other material capable of being injected through balloon tube 10 or guidewire tube 12 and longitudinal lumens that run to the balloon or distal end of device 2.

Referring to FIG. 1B, a longitudinal cross section of a first embodiment of the present disclosure is shown, with device 2, balloon 8 (in the expanded configuration) having valve 16 in the open position and valve 18, in the closed position. In this embodiment flow channels 20 and 22 are constructed through balloon 8. Valves 16 and 18 allow fluid to flow in only one direction. Balloon 8 has a proximal side 9 and a distal side 11. By way of example, if fluid pressure is higher on the proximal side of balloon 8 and lower on the distal side of balloon 8, both valves 16 & 18 will open in response to the pressure difference and allow fluid to flow distally through the valves. If the pressure is higher on the distal side of balloon 8, valves 16 and 18 will close and prevent fluid from flowing proximally. Alternately, the valves can be position or constructed so that fluid can pass proximally and be prevented from flowing in the distal direction. Valves 16 and 18 are shown as a simple "flap" type valve, however, they can be any type of valve, such as a diaphragm that open and close in response to a pressure differential. Balloon 8 is shown with two channels and two valves; however there can be 1, 2, 3 or more channels and/or valves. Device 2 of this embodiment may include channels and may or may not include valves. If valves are not included, a bidirectional flow will result.

Referring to FIG. 1C, a longitudinal cross section of another embodiment of the present disclosure is shown with device 24 and channel 26 running through and within catheter body 28. Balloon 30 has a proximal side 13 and a distal side 15. Channel 26 extends from the proximal side of balloon 30 to the distal side of balloon 30. A valve 32 is illustrated over channel 26 on the distal side of balloon 30, however, if desired the valve can be positioned on the proximal side of channel 26 and balloon 30. The function and operation of valve 32 of this embodiment of the present disclosure is identical to that presented in FIG. 1A and FIG. 1B. As in this embodiment, if valve 32 is not included, a bidirectional flow will result.

Figure 2:
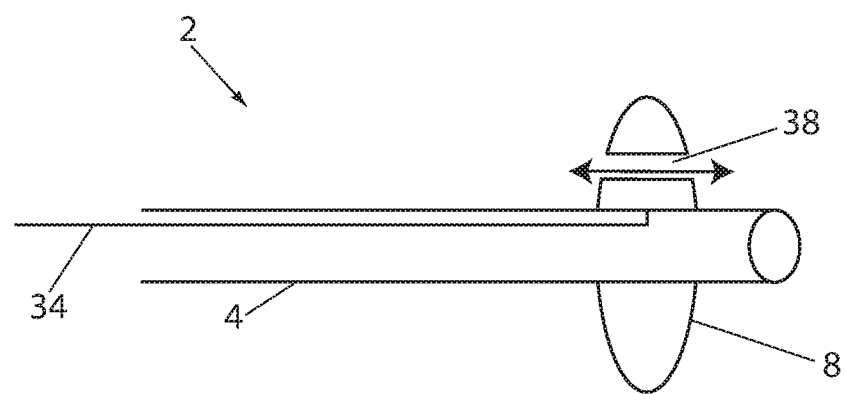
FIG. 2 illustrates a distal cross sectional view of a bidirectional embodiment.

FIG. 2 illustrates an exemplary embodiment of a longitudinal cross section of the distal end of device 2 with catheter body 4, balloon inflation lumen 34, balloon 8, and channel 38. Balloon inflation lumen 34 extends from the proximal end of catheter body 4 and exits at balloon 8. In this case, a valve in balloon 8 is not included and a bidirectional flow will result. The optimal balloon inflation lumen diameter is 0.1 mm to 0.5 mm; however this lumen can be in the range of 0.25 mm to 1 mm.

Figure 3:
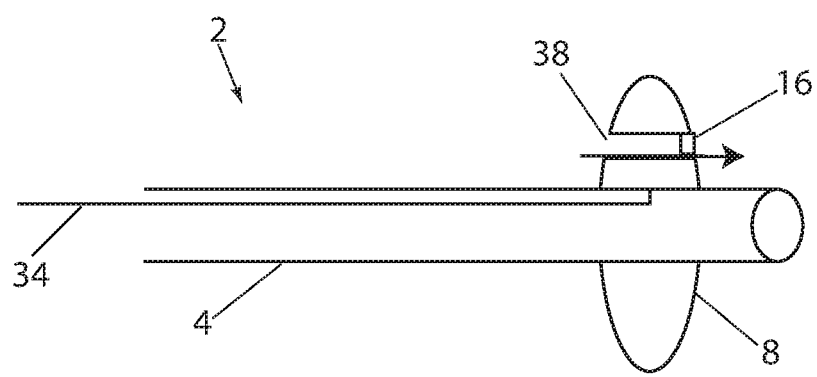
FIG. 3 illustrates a unidirectional embodiment.

FIG. 3 illustrates an example of a longitudinal cross section of the distal end of device 2 with catheter body 4, balloon inflation lumen 34, balloon 8, channel 38 and valve 16. Valve 16 is shown over the distal opening of channel 38 in the closed position, however if pressure is applied to the proximal valve surface through channel 38, the valve will allow fluid to pass distally. The valve 16 will prevent proximal flow. The valve can be positioned at the proximal or distal opening or anywhere within the cannel. Location and configuration of the valve will determine flow direction.

Figure 4:
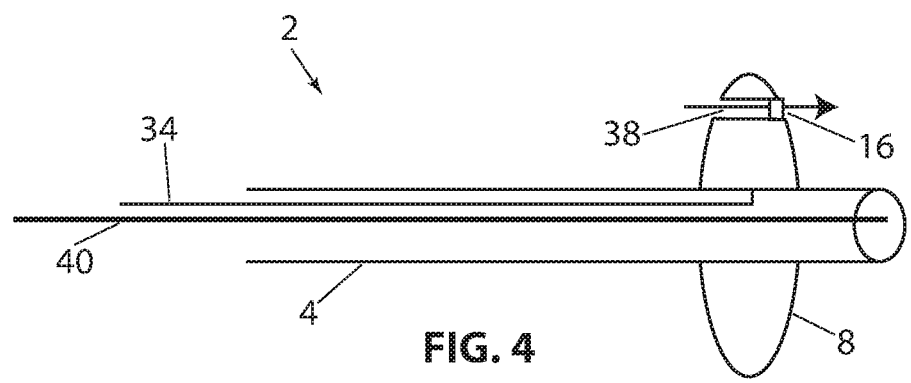
FIG. 4 illustrates a unidirectional embodiment with balloon inflation and guidewire/injection lumens.

Referring to FIG. 4, a longitudinal cross section of the distal end of device 2 is shown with catheter body 4, balloon inflation lumen 34, balloon 8, channel 38 and guidewire/injection lumen 40. Guidewire/injection lumen 40 extends from the proximal end of catheter body 4 and exits at the distal end of catheter body 4 or distal tip 6. The optimal guidewire/injection lumen diameter is 0.1 to 1.0 mm; however, this lumen can be in the range form 0.025 mm to 2 mm.

Figure 5:
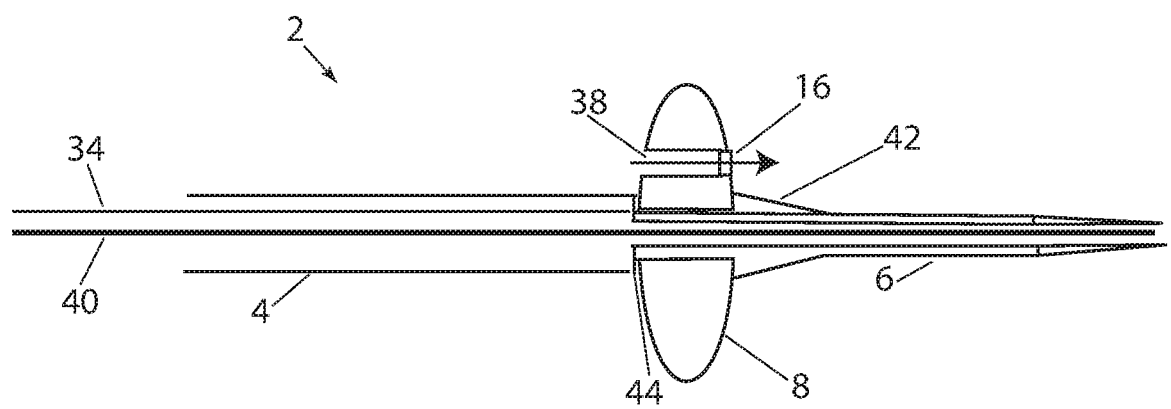
FIG. 5 illustrates an embodiment of the present disclosure including a distal tip and adapter.

Referring to FIG. 5, an example of a longitudinal cross section of the distal end of device 2 is shown with catheter body 4, balloon inflation lumen 34, balloon 8, channel 38, guidewire/injection lumen 40, adapter 42, balloon pocket 44 and distal tip 6. Distal tip 6 has an optimal diameter of 0.3 mm to 1.3 mm; however, distal tip 6 can range from 0.1 mm to 4 mm. Adapter 42 is adapted to create a smooth transition from the distal tip 6 to the catheter body 4. By way of example, if the distal tip 6 is 1 mm in diameter and the catheter body 4 is 2 mm in diameter, the adapter will taper from a diameter of 1 mm at its distal most point to 2 mm at its proximal most point to create a smooth transition from the smaller diameter distal tip to the larger diameter catheter body. As shown in FIG. 5, adapter 42 is positioned on the distal tip 6 at a location that is distal to distal end of catheter body 4, such that a balloon pocket 44 is formed between the distal end of catheter body 4 and the proximal end of adapter 42. Balloon pocket 44 holds unexpanded balloon 8 such that its unexpanded profile is minimized. Optimally balloon 8 would conform to an outer diameter that is equal to the diameter of the catheter body 4. By way of example, if the distal tip diameter is 1 mm and the catheter body is 2 mm, a balloon pocket is formed that is 0.5 mm deep. If balloon 8 is no more than 0.5 mm thick when unexpanded, it will lie equal to or below the surface of catheter body 4. This allows facilitation of the movement of the caterer within the artery or vein.

Figure 6:
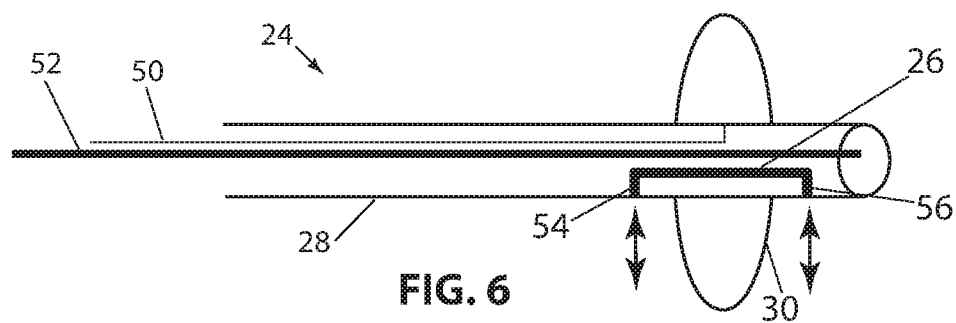
FIG. 6 illustrates an embodiment of the present disclosure with a bidirectional channel within the catheter.

Referring to FIG. 6, a longitudinal cross section of the distal end of device 24 is shown with catheter body 28, balloon inflation lumen 50, guidewire/injection lumen 52, balloon 30, and channel 26 with proximal port 54 and distal port 56. Channel 26 passes through and within catheter body 28 and extends from the proximal side of balloon 30 to the distal side of balloon 30. Port 54, at the proximal end of channel 26 is in fluid communication with the outside of the catheter body that is proximal to balloon 30 and port 56, at the distal end of channel 26, is in fluid communication with the area outside of catheter body 28 that is distal to the balloon 30. In this case, the flow through channel 26 is bidirectional. The optimal channel diameter is 0.1 mm to 1 mm; however this channel can be in the range of 0.05 mm to 2 mm.

Figure 7:
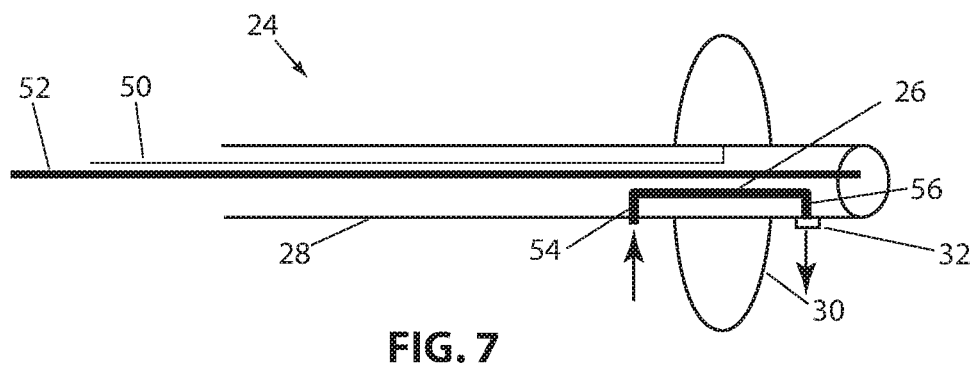
FIG. 7 illustrates an embodiment of the present disclosure with a unidirectional channel.

FIG. 7 illustrates an exemplary embodiment of a longitudinal cross section of the distal end of device 24 with catheter body 28, balloon inflation lumen 50, guidewire/injection lumen 52, balloon 30, valve 32 and channel 26 with proximal port 54 and distal port 56. Channel 26 passes through and within catheter body 28 and extends from the proximal side of balloon 30 to the distal side of balloon 30. Port 54, at the proximal end of channel 26 is in fluid communication with the outside of the catheter body that is proximal to balloon 30 and port 56, at the distal end of channel 26, is in fluid communication with the area outside of catheter body 28 that is distal to the balloon 30. Valve 32, is shown at the opening of port 56 of channel 26. Valve 32 allows flow in the distal direction and prevents flow in the proximal direction. In this case, the flow through channel 26 is unidirectional. The optimal channel diameter is 0.1 mm to 1 mm; however this channel can be in the range of 0.05 mm to 2 mm. The valve can be positioned at the proximal or distal opening or anywhere within the channel. Location and configuration of the valve will determine flow direction.

Figure 8:
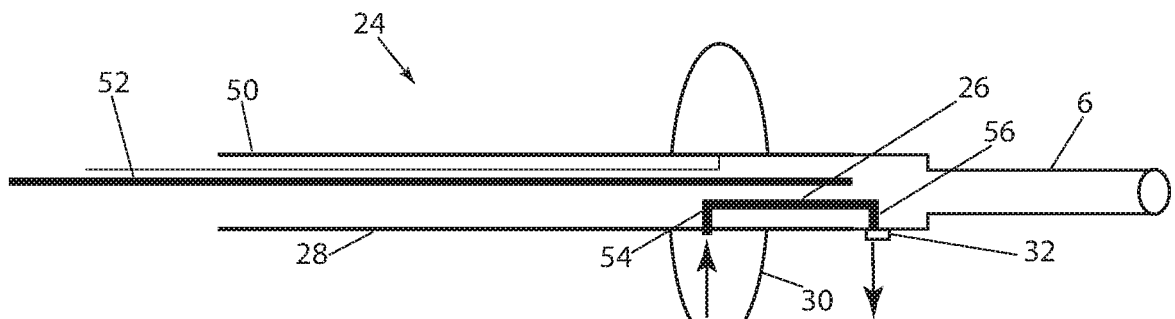
FIG. 8 illustrates a device of the present disclosure with a distal tip.
Figure 9A:
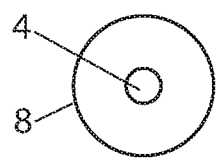
FIG. 9A shows a linear cross section through the catheter and balloon.
Figure 9B:
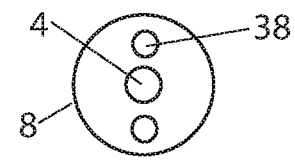
FIG. 9B shows a linear cross section through the catheter and balloon and two circular bidirectional channels.
Figure 9C:
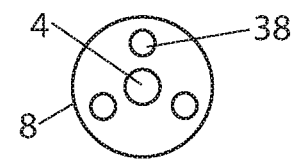
FIG. 9C shows a linear cross section through the catheter and balloon and three circular bidirectional channels.
Figure 9D:
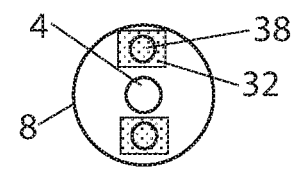
FIG. 9D shows a linear cross section through the catheter and balloon and two circular unidirectional bypass channels with individual valves on each channel.
Figure 9E:
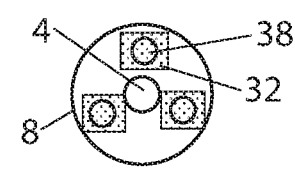
FIG. 9E shows a linear cross section through the catheter and balloon and three circular unidirectional bypass channels with individual valves on each channel.
Figure 9F:
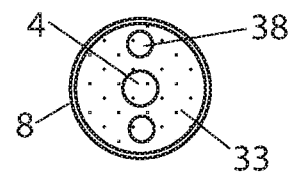
FIG. 9F shows a linear cross section through the catheter and balloon and two circular unidirectional channels with a one-piece valve covering both channels.
Figure 9G:
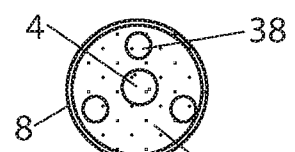
FIG. 9G shows a linear cross section through the catheter and balloon and two circular unidirectional channels with a one-piece valve covering three channels.
Figure 9H:
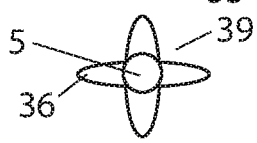
FIG. 9H shows a linear cross section through the catheter and balloon and four bidirectional bypass channels formed from pleats in the balloon.
Figure 9I:
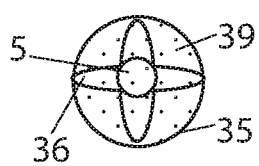
FIG. 9I shows a linear cross section through the catheter and balloon and four unidirectional bypass channels formed from pleats in the balloon and a one-piece valve covering all 4 channels.
Figure 9J:
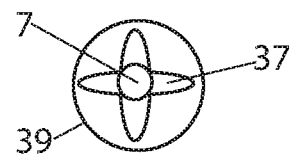
FIG. 9J shows a linear cross section through the catheter and balloon and four bidirectional channels which radiate outward from the catheter.
Figure 9K:
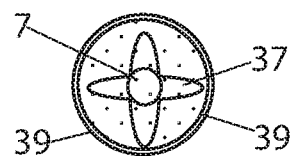
FIG. 9K shows a linear cross section through the catheter and balloon and four unidirectional channels which radiate outward from the catheter and a one-piece valve covering all four valves.
Figure 9L:
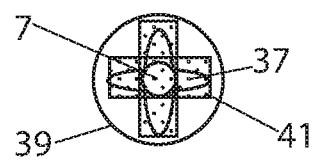
FIG. 9L shows a linear cross section through the catheter and balloon and four unidirectional channels which radiate outward from the catheter outward and a single cross shaped valve covering all four channels.

Referring to FIG. 8, a longitudinal cross section of the distal end of device 24 is shown with catheter body 28, balloon inflation lumen 50, guidewire/injection lumen 52, balloon 30, valve 32, channel 26 and distal tip 6.

Referring to FIG. 9, linear cross sections through catheter body 4 and balloon 8 are shown. FIG. 9 illustrates examples of flow channels through a balloon positioned on a catheter, however, various alternatives, modifications, and equivalents may be used. FIG. 9A shows catheter 4 and balloon 8 without a channel. FIG. 9B shows catheter 4 and balloon 8 with two channels 38 through balloon 8. In this case the flow is bidirectional. FIG. 9C shows a catheter and balloon with three bidirectional cannels. FIG. 9D shows a catheter 4 with a balloon 8 with two channels, each with a one-way valve. In this case the channel flow in each channel is unidirectional. FIG. 9E shows catheter 4 with balloon 8 and three channels 38, each with an independent valve 38. The flow is unidirectional. FIG. 9F is a catheter and balloon with two channels and a single circumferential valve 33 that covers both channels 38 and allows flow in only 1 direction. FIG. 9G shows a catheter 4 and balloon 8 with three channels and a single circumferential valve 33 that covers all three channels. FIG. 9H shows a catheter 5, and four bidirectional channels 39 that are formed by pleating balloon 36 from the outer circumference of the expanded balloon, inward toward the central catheter and securing the inner apex of the balloon to the catheter, thereby forming triangular channels which radiate outward from the central catheter, forming a "V" shape. The lower point of the 'V' is positioned at the catheter surface and the open end of the "V" is positioned at the outer circumference of the circle defined by the largest diameter of the inflated balloon. FIG. 9I shows four channels 39, with a single circumferential valve 35 covering all four triangular channels. Although the figure shows four channels, the device of this disclosure can have one, two, three, four or any number of channels. FIG. 9J shows a catheter 7 and a balloon 39 with four channels 37 that are formed by pleating the balloon 39 from the inner catheter 7 toward the outer circumference of the expanded balloon 39. FIG. 9K shows four channels 37 as in FIG. 9J with a single circumferential valve 39 that covers all four channels 37. FIG. 9L shows four channels 37 as in FIG. 9J with a one piece cross-shaped flap valve 41.

While the above is a complete description of exemplary embodiments of the present disclosure, various alternatives, modifications, and equivalents may be used. Therefore, the above description should not be taken as limiting the scope of the disclosure, which is defined by the appended claims and the claims in any subsequent applications claiming priority hereto.

Figure 10:
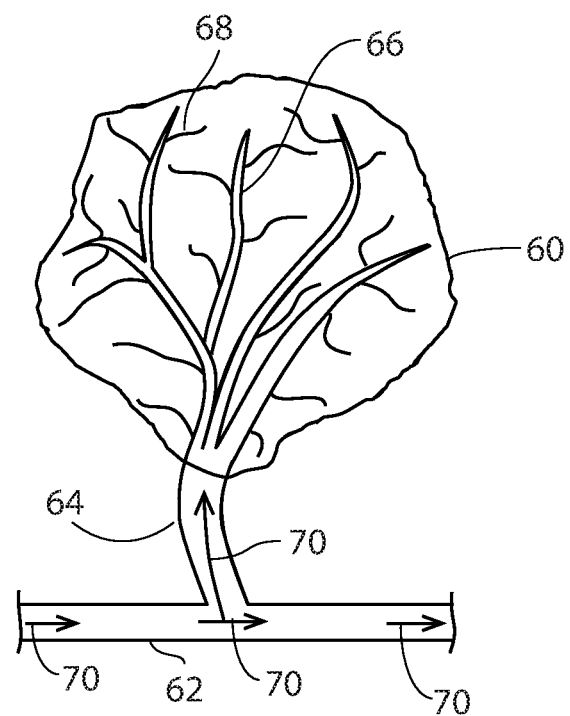
FIG. 10 shows a tumor and associated vasculature.

FIG. 10 illustrates a tumor and its associated vasculature with tumor 60, main artery 62, side branch artery 64, tumor artery 66, tumor capillary 68 and anterograde arterial flow direction illustrated by arrows 70.

Figure 11:
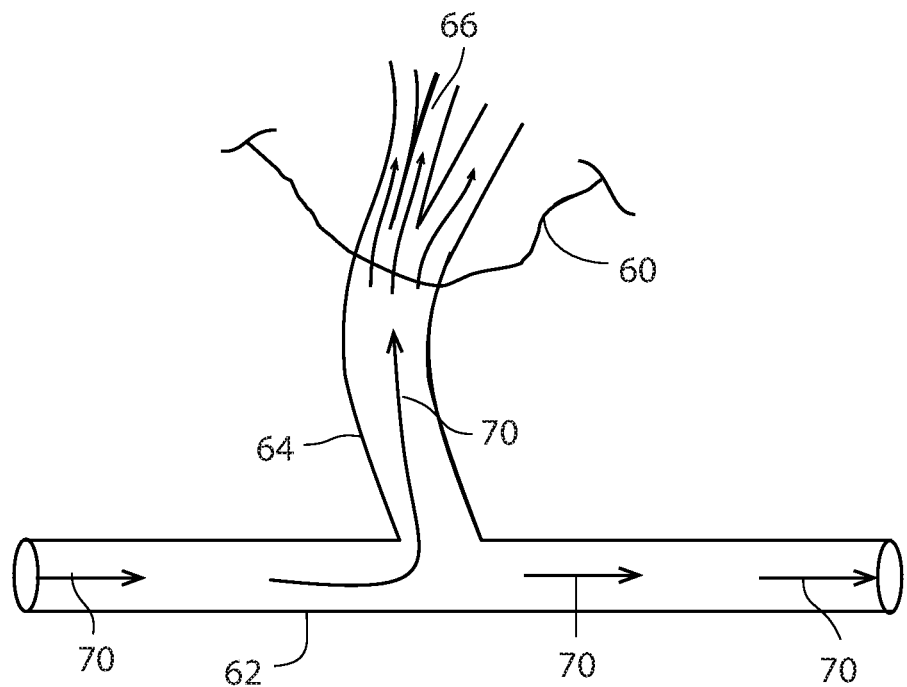
FIG. 11 shows an expanded view of a tumor and its vasculature including blood flow direction.

FIG. 11 is an expanded view of FIG. 10 with tumor 60, main artery 62, side branch artery 64, tumor artery 66 and anterograde arterial flow direction illustrated by arrows 70.

Figure 12:
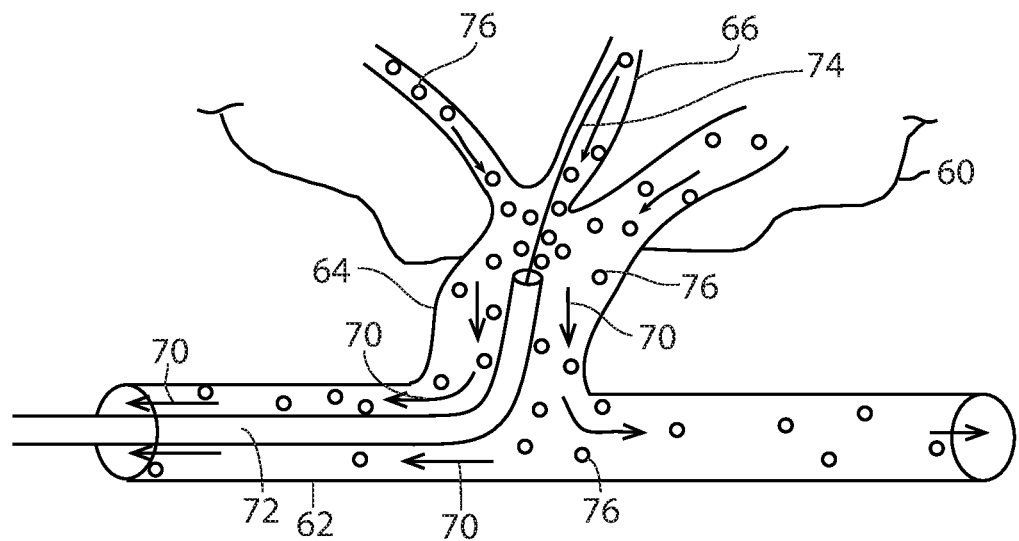
FIG. 12 illustrates a standard micro-catheter over a guidewire inside the tumor vasculature with injection.

FIG. 12 illustrates injection of fluid 76 using a standard micro-catheter 72 with tumor 60, main artery 62, side branch artery 64, tumor artery 66, guidewire 74 and retrograde arterial flow direction illustrated by arrows 70. In this instance, injection pressure and flow volume of the fluid 76 that may contain anti-cancer drugs, radioembolic substances, chemoembolic substances, embolic agents or the like, through microcatheter 72 is higher than the tumor vasculature can accept causing a reversal of fluid flow and blood flow in tumor artery 66, side branch artery 64 and main artery 62. This retrograde flow causes the injected fluid 76 to enter the main artery, flowing in both directions and into the general circulation resulting in the injected fluid traveling to non-target tissues and organs. This unintended delivery of fluid 76 to non-target sites is undesirable and must be avoided since it can cause serious complications. The present disclosure solves this problem by preventing reflux and associated non-target delivery of fluid 76.

Figure 13:
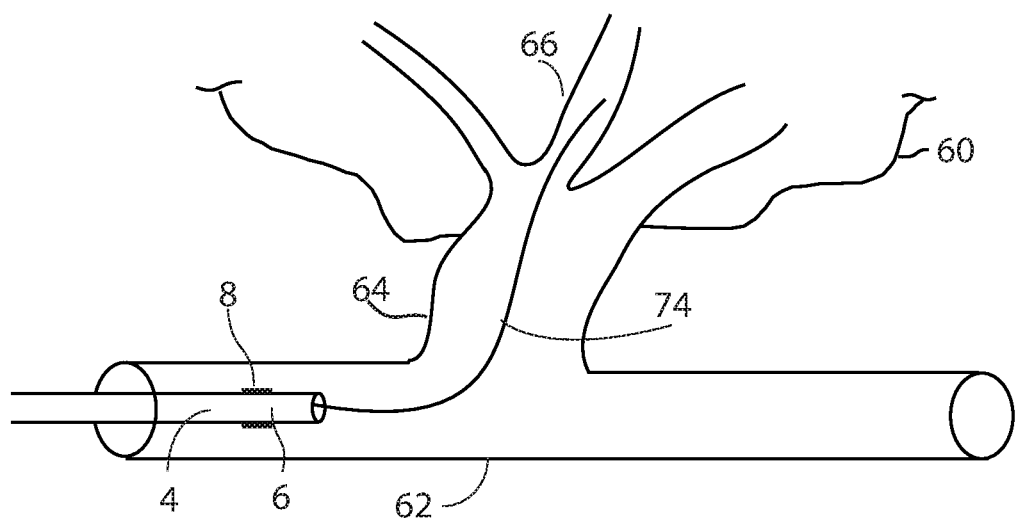
FIG. 13 illustrates a catheter of the present disclosure over a guidewire and inside a main artery

FIG. 13 illustrates catheter 4 of the present disclosure entering the main artery with balloon 8 and distal tip 6. Although the entry point from outside the body is typically through the femoral artery at the groin, any artery or vein from any location on the body can be used for access provided that it creates a pathway to the target vasculature.

Figure 14:
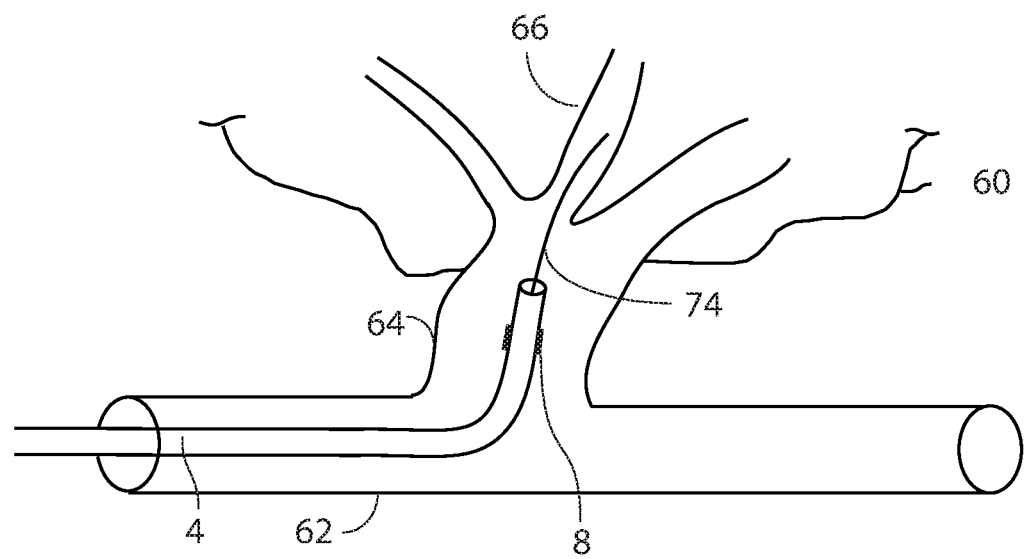
FIG. 14 illustrates a catheter of the present disclosure over a guidewire and inside the branch artery.

FIG. 14 illustrates catheter 4 with balloon 8, of the present disclosure, following guidewire 74 into side branch artery 64.

Figure 15:
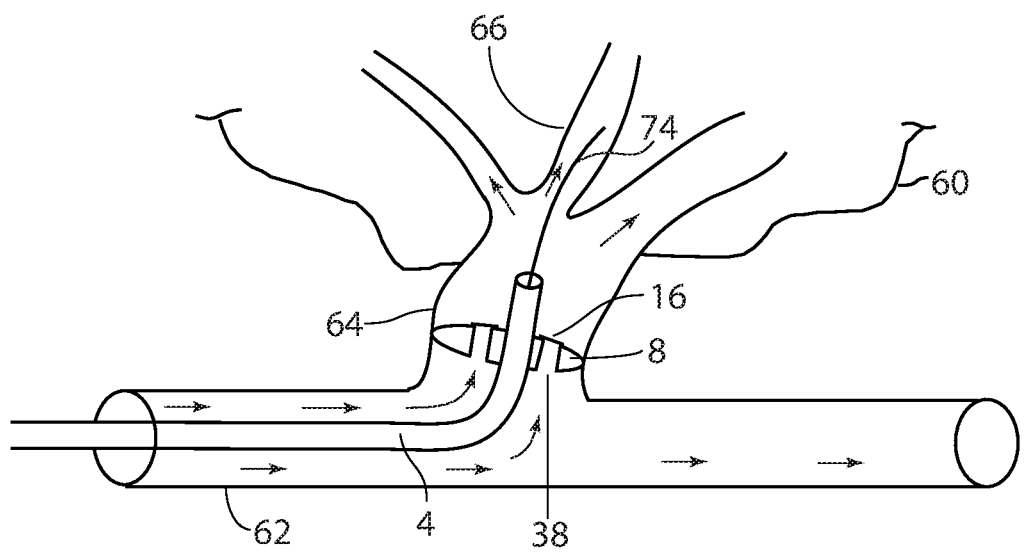
FIG. 15 illustrates a catheter of the present disclosure with inflated balloon and closed valves.

FIG. 15 illustrates catheter 4, inside the branch artery 64 with balloon 8 in the expanded configuration, channels 38 and valves 16. Valves 16 are illustrated in the closed position immediately following the inflation of balloon 8.

Figure 16:
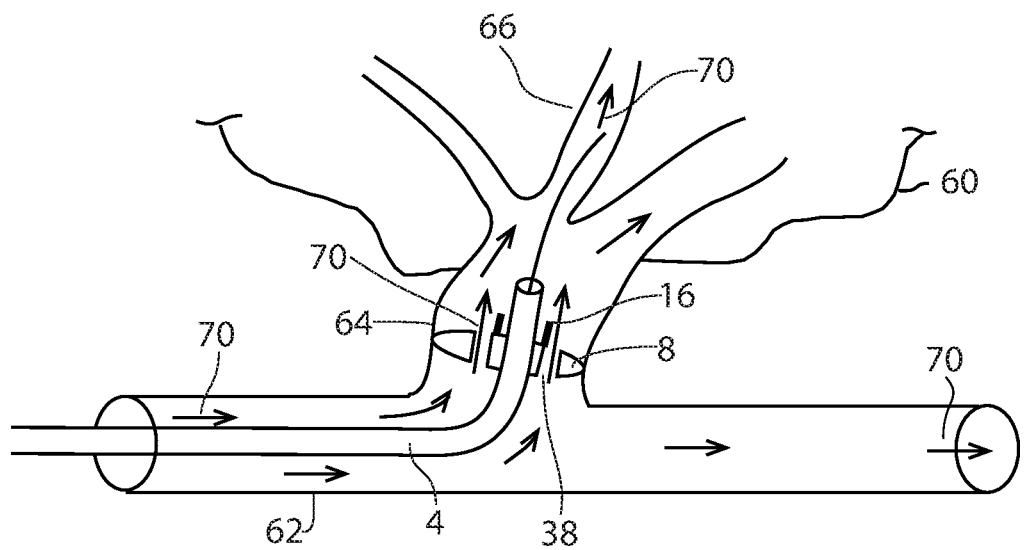
FIG. 16 illustrates a catheter of the present disclosure with inflated balloon and open valves.

FIG. 16 illustrates catheter 4, inside the branch artery 64 with balloon 8 in the expanded configuration, channels 38 and valves 16. Valves 16 are illustrated in the open position since anterograde blood flow as indicated by arrows 70 and associated blood pressure causes these valves to open and allow the blood to continue to flow in the anterograde direction and into the tumor vasculature.

Figure 17:
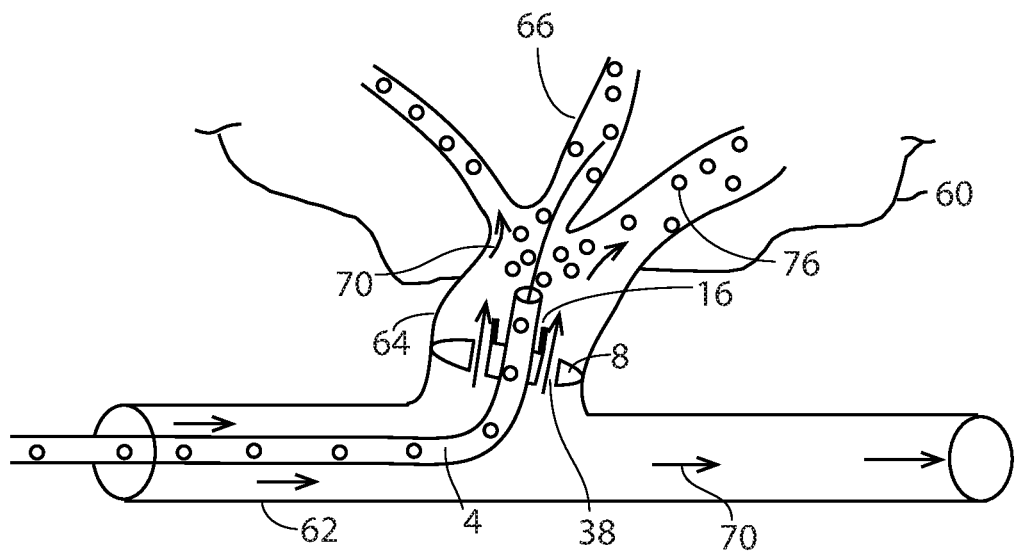
FIG. 17 illustrates a catheter of the present disclosure with inflated balloons, open valves and initiation of fluid injection.

FIG. 17 illustrates the initial injection of fluid 76 into side branch artery 64 through catheter 4, channels 38 and open valves 16. When the injection is initiated, the anterograde blood flow carries the injection fluid 76 into the tumor vasculature including tumor arteries 66, and capillaries 68.

Figures 18, 19:
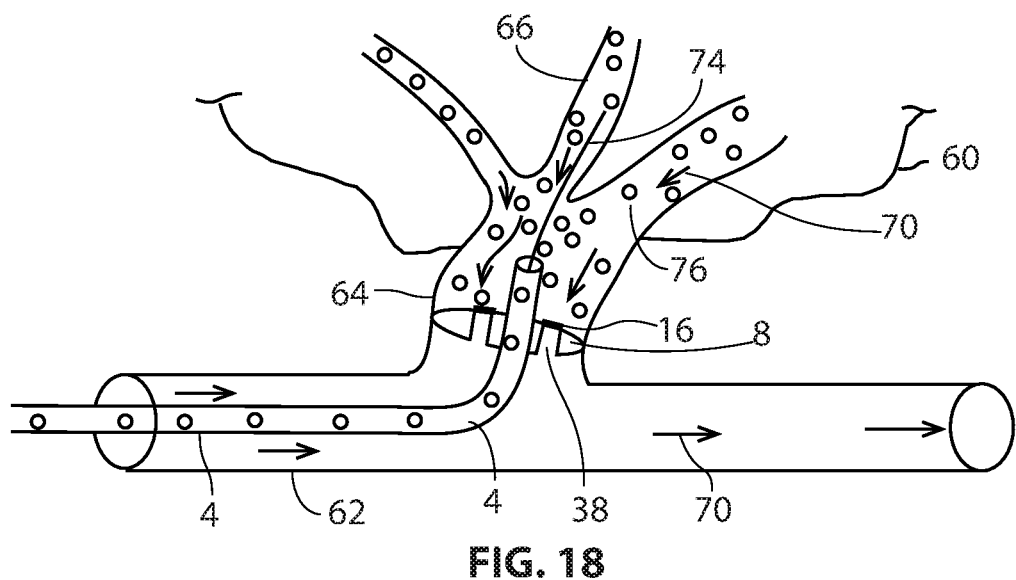
FIG. 18 illustrates a catheter of the present disclosure during injection with inflated balloons and valves closed.
FIG. 19 illustrates a catheter of the present disclosure at a period of time following the completion of injection with inflated balloon and open valves.

FIG. 18 illustrates injection of fluid 76 at a point when fluid pressure increases within the tumor vasculature and concomitant retrograde arterial blood flow and injection fluid flow in the direction as illustrated by arrows 70. Shown in this figure are catheter 4 of the present disclosure with tumor 60, main artery 62, side branch artery 64, tumor artery 66, and guidewire 74. Injection fluid 76, may contain anti-cancer drugs, radioembolic substances, chemoembolic substances, embolic agents or the like, which can cause serious complications if delivered to non-target sites. In this case, the retrograde pressure causes valves 16 to close and prevents the reflux of injection fluid into the general circulation, thereby preventing complications associated with delivery of injection fluid to non-target sites.

FIG. 19 illustrates a point in time following the completion of fluid injection. At this point, the pressure in the vasculature that is the distal to balloon 8, including side branch 64 and tumor artery 66, is reduced below normal blood pressure due to the gradual uptake of the injected fluid into the tumor vasculature. The blood pressure on the proximal surface of balloon 8 and valves 16 cause them to open allowing anterograde blood flow to be reestablished. When this occurs, the excess fluid 76 distal to balloon 8 and within the side branch artery 64 and tumor vasculature, including tumor artery 66 and tumor capillaries 68, is flushed forward and up into the tumor vasculature, thereby enabling delivery of the entire fluid dose and eliminating fluid reflux and associated complications.

Figure 20:
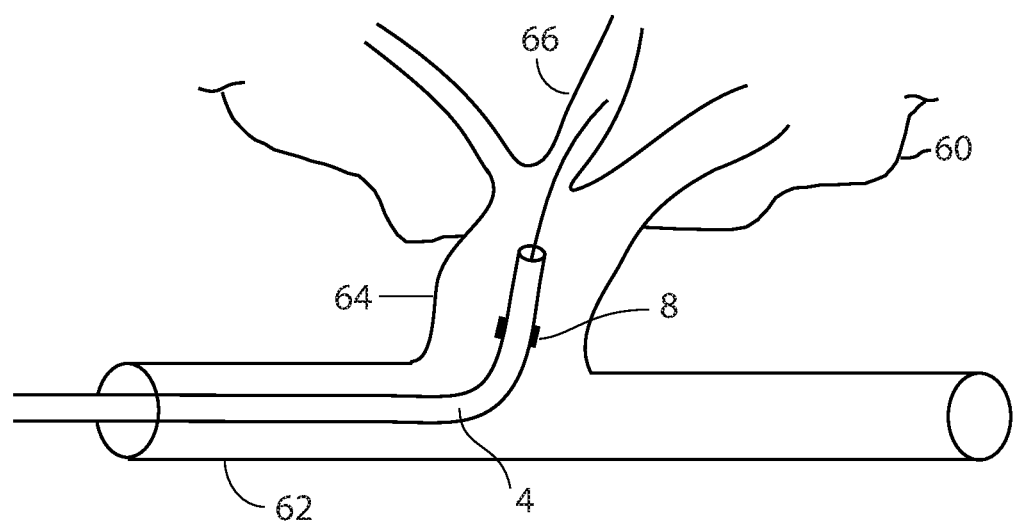
FIG. 20 shows the deflation of the balloon.

FIG. 20 illustrates the deflation of balloon 8 on catheter 4.

Figure 21:
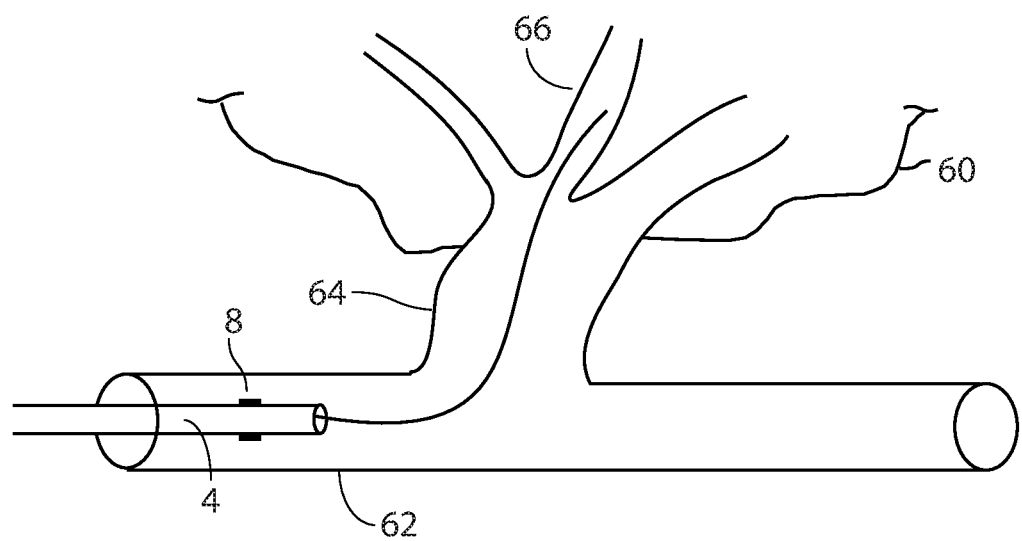
FIG. 21 shows the withdrawal of the catheter into a main artery.

FIG. 21 illustrates the withdrawal of catheter 4 into the main artery 62.

Figure 22:
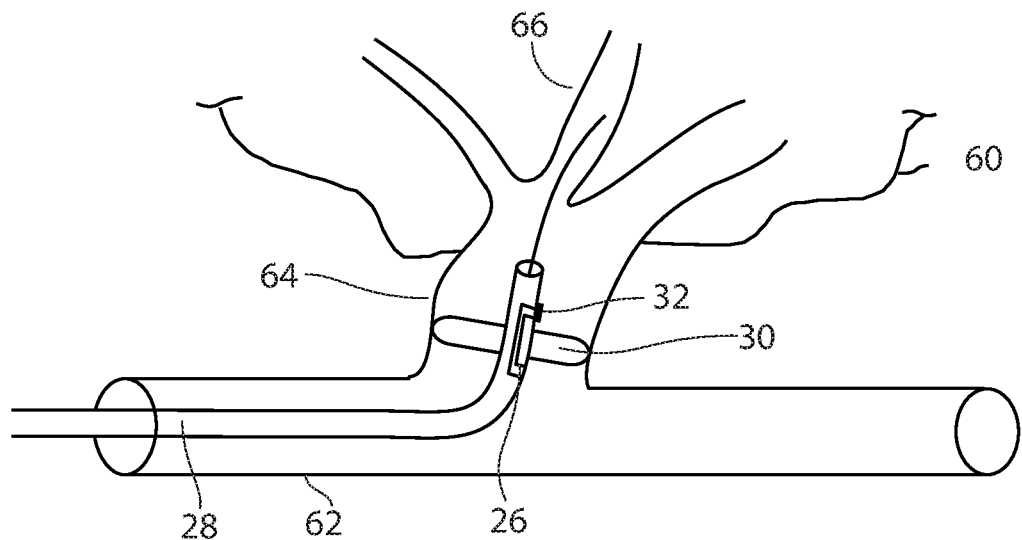
FIG. 22 shows an embodiment of the present disclosure with a channel within the catheter and closed valve.

FIG. 22 illustrates another embodiment of the present disclosure as described in FIGS. 6, 7 and 8. In this case valve 32 on the distal end of channel 26 of catheter 28 is in the closed position.

Figure 23:
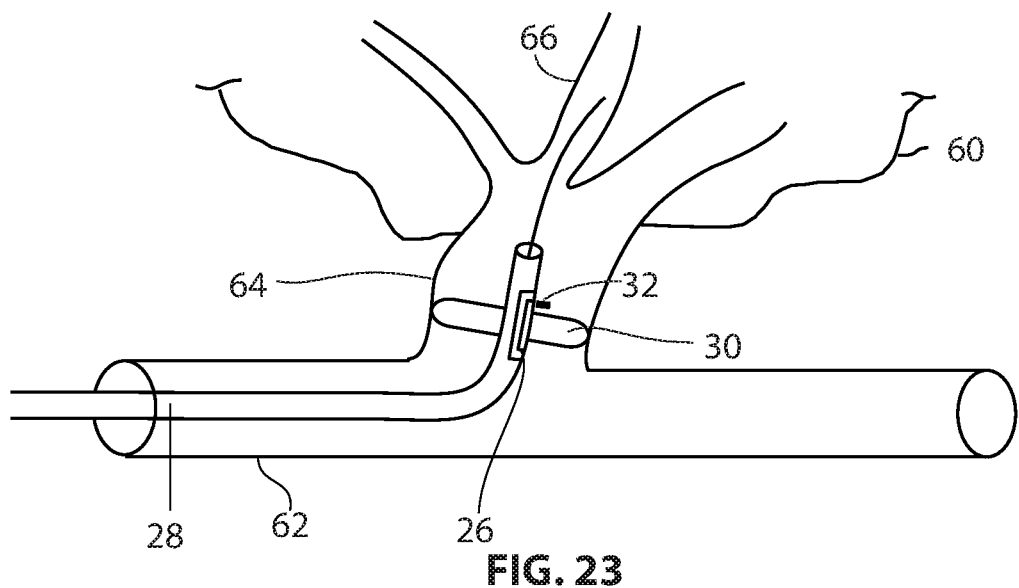
FIG. 23 shows an embodiment of the present disclosure with a channel within the catheter and open valve.

FIG. 23 illustrates an embodiment of FIG. 22 with valve 32 in the open position.

A Method, according to the present disclosure is illustrated by FIGS. 13 through 21; the method applies to both the embodiment illustrated in FIGS. 1B, 2, 3, 4 and 5 and the embodiment illustrated in FIGS. 1C, 6, 7, 8, 22 and 23.

Figure 24A:
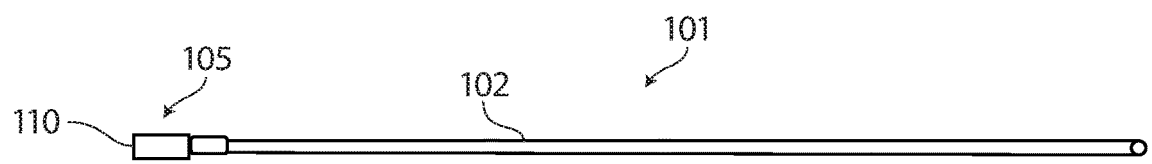
FIG. 24A illustrates a standard microcatheter.

Referring to FIG. 24A, a longitudinal cross section of a standard single lumen straight tip catheter 101, having a proximal and distal end, is shown with catheter body 102, and hub 105. Hub 105, positioned at the proximal end, further comprises guidewire/injection lumen 110, in fluid communication with a catheter lumen longitudinally oriented and extending from hub 105 and exiting at the distal end of the catheter body 102. The proximal hub connects to a syringe or other means to inject fluids via a luer fitting, thereby allowing injection of a fluid through the longitudinal lumen and exit at the distal end of catheter body 102.

Figure 24B:
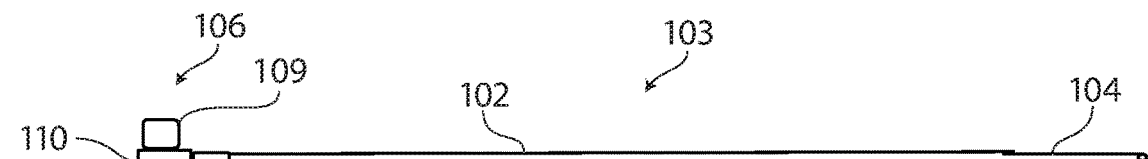
FIGS. 24B, 24C, 24D and 24E illustrate a cross sectional view of a sequential construction of an embodiment of the present disclosure.
Figure 24C:
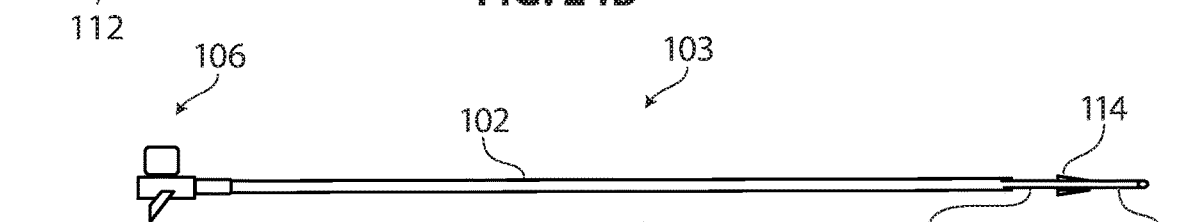
Figure 24D:
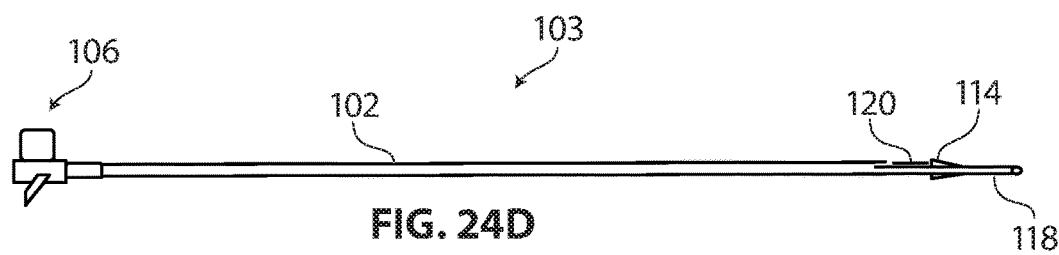
Figure 24E:
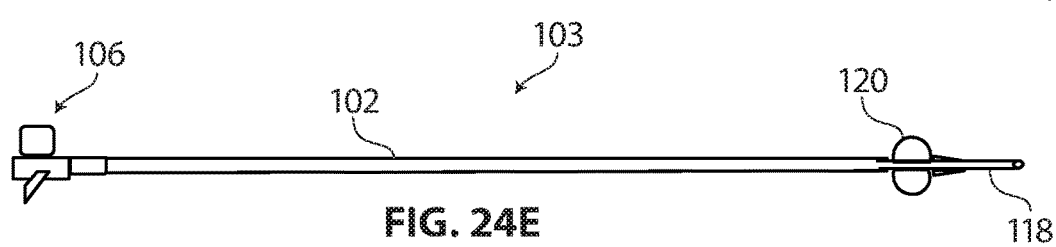

Referring to FIG. 24B through 24E, longitudinal cross-sections of a sequential assembly of a preferred embodiment of the present disclosure is shown. Referring to FIG. 24B, device 103 is shown, having a proximal and a distal end, catheter body 102, catheter extension 104 and hub 106. Hub 106 further comprises handle 109, guidewire/injection luer fitting 110 and balloon fill luer fitting 112. Luer fitting 110 is in fluid communication with a first longitudinal guidewire/injection lumen of catheter body 102, extending to the distal end of catheter extension 104, and luer fitting 112, in fluid communication with a second longitudinal balloon fill lumen of catheter body 102, extending to a balloon fill port located near the distal end of catheter body 102. FIG. 24C further comprises nose cone 114, positioned on catheter extension 104, forming balloon pocket 116 disposed between the distal end of catheter body 102 and nose cone 114. Further, a portion of catheter extension 104 can, if desired, extend distal to nose cone 114, thereby forming distal tip 118. FIG. 24C, further illustrates occlusion balloon 120 in a radially compressed configuration and FIG. 24E illustrating balloon 120 in a radially expanded configuration. Hubs 106 can be constructed from styrene, polyurethane, polypropylene, lipid resistant polycarbonate, polycarbonate, Pebax (polyether block amide), of any durometer, or any convenient material and can have any configuration, including, but not limited to, a solid structure comprising two lumens or tubular extensions of the lumens of catheter body 102, provided that they are in fluid communication as described above. Catheter body 102 can be formed from any plastic or thermoplastic material including polyurethane, PTFE, polyimide, polypropylene, Pebax or the like, and can comprise a single section or multiple sections of different diameter, durometer, braid or coil reinforcement or any convenient construction with a diameter of between 1 Fr and 10 Fr more typically of 2 Fr to 5 Fr. Catheter extension 104 can have a diameter of 0.5 Fr to 5 Fr, more typically of 1 Fr to 3 Fr and can be absent or can be of any length, typically 2 mm to 30 mm, more typically from 5 mm to 20 mm. If the catheter extension 104 extends beyond nose cone 114, the section distal to the nose cone forms the distal tip 118. Distal tip 118 is advantageous when injecting deep into the tumor vasculature is desired and will also help tracking of device 103 over a guidewire around sharp corners and through a tortuous vasculature path. Nose cone 114 can be made from any polymer or metal or can be formed from a radiopaque marker band. Balloon pocket 116 can be of any length between 2 mm and 50 mm, more typically between 5 mm and 20 mm. Occlusion balloon 120 has a longitudinal length of 1 mm to 30 mm, more typically of 2 mm to 10 mm and a diameter of 1 mm to 50 mm, typically from 2 mm to 10 mm and can be composed of silicone, polyurethane, polyethylene, PET (polyethylene terephthalate), nylon or the like and can be of any configuration or of any length or shape and can be glued, chemically bonded, heat bonded, RF welded, sonically fused, compressed or crimped under a collar to catheter 102 or catheter extension 104.

Referring to FIG. 25A, a distal section of a device 128 of a preferred embodiment of the present disclosure is shown and includes catheter body 102, catheter extension 104, nose cone 114, balloon pocket 116, balloon fill lumen 124, guidewire/injection lumen 126 and radially compressed balloon 120. Referring to FIG. 25B, balloon 120 is shown in its radially expanded configuration. Balloon fill lumen 124 can be of any convenient shape including but not limited to round, semicircular, or crescent or any shape, typically optimized to provide maximum area and flow rate. Guidewire/injection lumen 126 is typically round, having a diameter of 0.005" to 0.1", more typically from 0.01" to 0.05"; however, it can be of any desirable shape.

Referring to FIG. 26A, the distal end 133 of an embodiment of the present disclosure is shown with catheter body 102, catheter extension 104, nose cone 114, balloon pocket 116, balloon fill lumen 124, guidewire/injection lumen 126 and radially compressed balloon 120. In this instance, the balloon pocket 116 is formed between a proximal collar 130 and a distal collar 114, tapered forward thereby forming a nose cone. The balloon bonding tails 115 can be bonded within the pocket or compressed or bonded under collars 114 and 130. Distal collar 130 can comprise a metal, such as a radiopaque marker band or a plastic such as heat shrink tubing and can be 1 mm to 20 mm in length, more typically from 2 mm to 10 mm. Balloon fill lumen 124 is shown traveling under balloon pocket 116 and ending at its distal end. Guidewire/injection lumen 126 is shown traveling longitudinally through catheter 102 and catheter extension 104, ending at the distal end of the catheter. Balloon 120 is shown tucked into pocket 116 with outer diameter substantially no larger than the outer diameter of catheter body 102. FIG. 26B shows the same construction as FIG. 26A with balloon 120 in its radially expanded configuration.

Figure 27A:
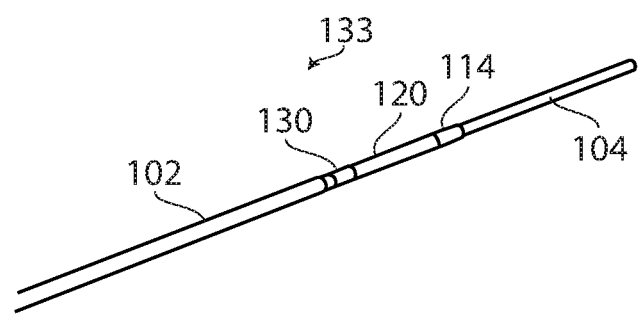
FIGS. 27A and 27B illustrate a distal catheter with and occlusion balloon unexpanded and expanded.
Figure 27B:
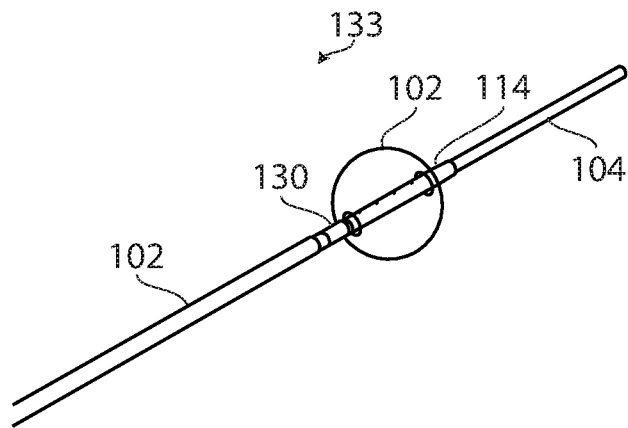

Referring to FIG. 27A, a view of distal section 133 is shown and further illustrates that the profile of a preferred embodiment of the present disclosure, including the radially compressed balloon 120, the distal collar 114 and the proximal band 130, have an outer diameter equal to or less than that of catheter body 102. FIG. 27B shows the same construction as FIG. 27A with balloon 120 expanded from pocket 116 and between collars 114 and 130.

Figure 28A:
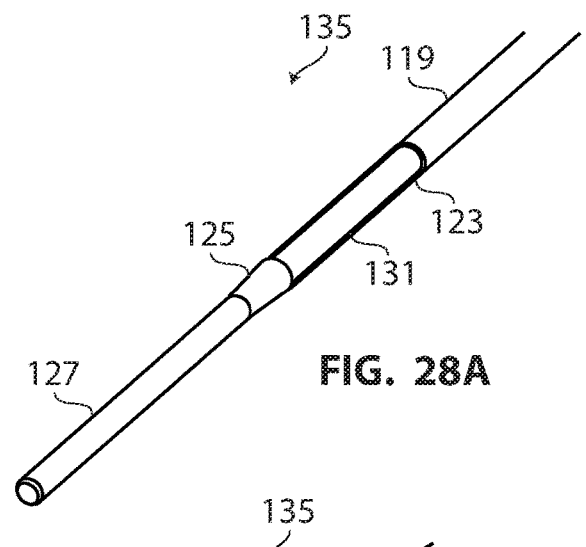
FIGS. 28A, 28B, 28C, and 28D illustrate an embodiment of the present disclosure including a two layer catheter.
Figure 28B:
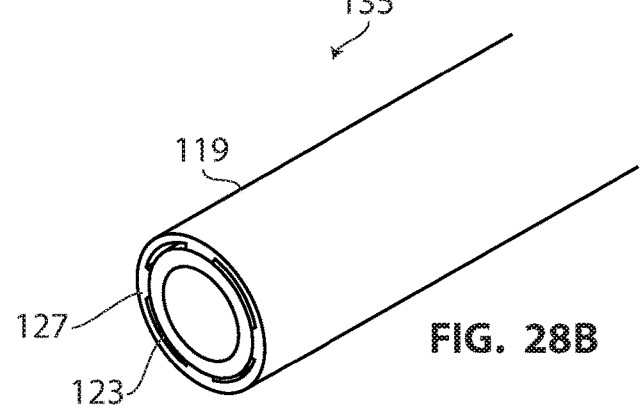
Figure 28C:
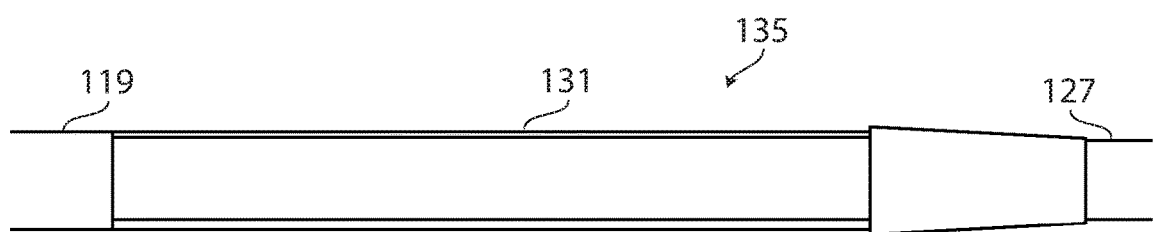
Figure 28D:
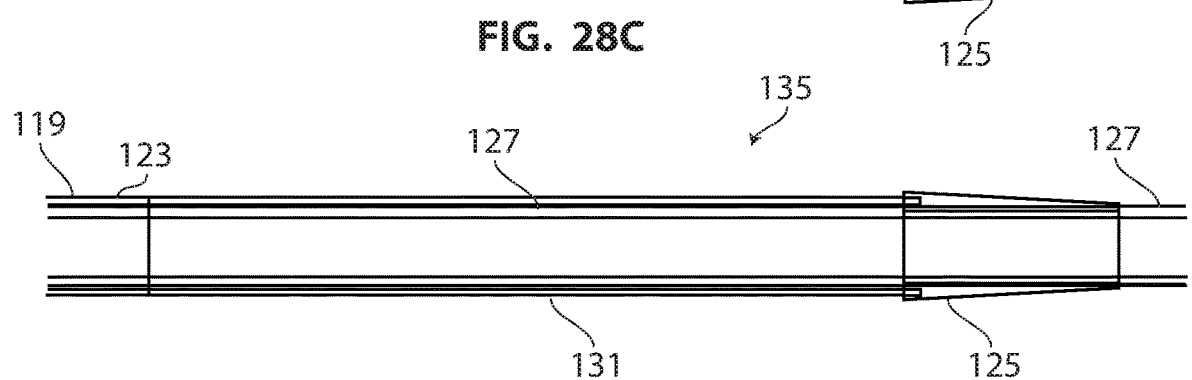

Referring to FIG. 28A, a distal section of an alternate embodiment 135 of the present disclosure is shown with outer catheter 119, inner catheter 127, nose cone 125, radially constrained balloon 131 and catheter channels 123. The outer catheter 119 is adapted over inner catheter 121, the catheters configured to provide a radially distributed space between inner and outer catheters extending longitudinally along the length of device 135. Outer and inner catheters can have a length of 10 cm to 250 cm, more typically 50 cm to 150 cm and a diameter of between 0.5 Fr and 10 Fr more typically of 1 Fr to 5 Fr. Inner catheter 127 can have a length less than, equal to, or longer than the outer catheter 119, however in the present figure, inner catheter 127 is shown to be longer than outer catheter 119, its distal end forming the catheter extension 127. Nose cone 125 is disposed along the distal extension of inner catheter 127 at some distance from the distal end of outer catheter 119, the distance being 2 mm to 50 mm, more typically between 5 mm and 20 mm. The balloon pocket is formed between the distal end of catheter 119 and the proximal end of nose cone 125. FIG. 28B shows an end view of outer catheter 119, disposed over inner catheter 127, with radially configured channels 123 and stand-offs 127 disposed between outer catheter 119 and inner catheter 127. Four channels are illustrated, however device 135 can have 0, 1, 2, 3, 4 or any number of channels and stand-offs, the stand-offs defining the outer edges of the channels 123 and can be formed on either the inner or outer catheter with a height limited only by the diameter of the inner and outer catheters and space there between. Although stand-offs are shown, they are not required, provided that the inner catheter OD is smaller than the outer catheter ID, thereby forming a space between the inner and outer catheters which allow fluid to flow longitudinally along device 135. Device 135 can comprise single layer inner and outer catheters or one or both can have multiple layers. In a preferred embodiment, outer catheter 19 is a three layer construction with an outer Pebax layer, a central polyimide layer including reinforcement such as a coil or braid and an inner Teflon layer. Inner catheter 127 is a single layer of low friction tubing, or tubing of similar construction to that described for the outer catheter 119. FIG. 28C shows a longitudinal view of device 135 with outer catheter 119, unexpanded balloon 131, nose cone 125 and a catheter extension of inner catheter 127. Balloon 131 is shown tucked within a pocket formed between the distal end of catheter 119 and the proximal end of nosecone 125. FIG. 28D shows a longitudinal cross section of device 135, showing balloon inflation channel 123 disposed between outer catheter 119 and inner catheter 121. In this instance, the distal end of balloon 131 is shown inserted into the proximal end of nose cone 125; however both proximal and distal balloon tails can be bonded directly to inner catheter 127, reflowed into catheter 119 or nose cone 125 or by any means, provided that the balloon tails are positioned approximately below the outer diameter of catheter 119.

Figure 29:
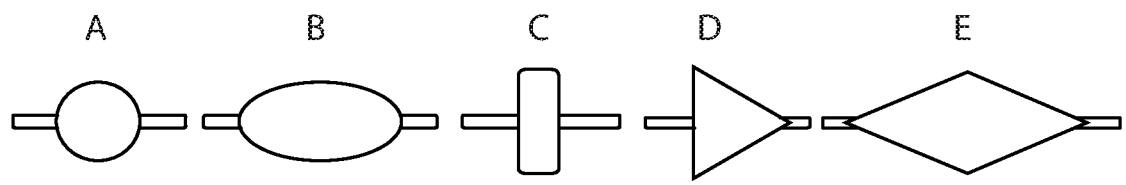
FIG. 29 gives examples of balloons used in various embodiments of the present disclosure.

Referring to FIG. 29A though FIG. 29E, examples of balloon configurations that may be used in the device of the present disclosure are shown which can be compliant or noncompliant, dilation or occlusion and can be made from any material including, but not limited to, silicone, polyurethane, polyethylene, PET (polyethylene terephthalate) and nylon.

Figure 30:
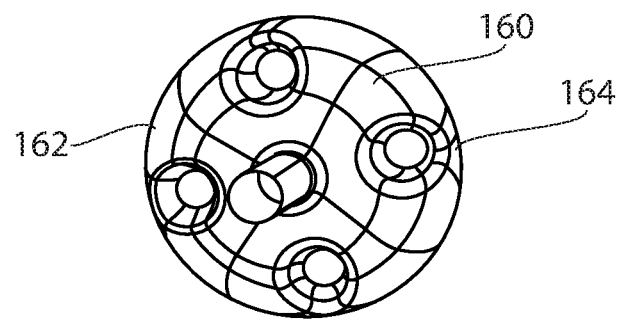
FIG. 30 shows a front view of a balloon with one-way bypass channels and valves.

Referring to FIG. 30, a surface view of balloon 160 is shown with one-way bypass channels 162 and valves 164, the balloon is described in detail in co-pending patent application No. 61/821,058.

Balloon 160 and valves 164 allow flow from the compartment proximal to the proximal surface of balloon 160 to the compartment distal to the distal surface of balloon 160 (anterograde flow) and prevents flow from the compartment distal to the distal surface of balloon 160 to the compartment proximal to the proximal surface of balloon 160 (retrograde flow). Balloon 160 can be disposed on the catheter of the present disclosure and held within a balloon pocket as illustrated in FIGS. 24-29 and enable anterograde injection of therapeutic agents from within an artery and into a target while maintaining normal (anterograde) blood flow through channels 162 of balloon 160 and prevent retrograde flow (reflux) of therapeutic agents backward over the catheter, even when pressure distal to balloon 160 is elevated above systolic.

Figure 31:
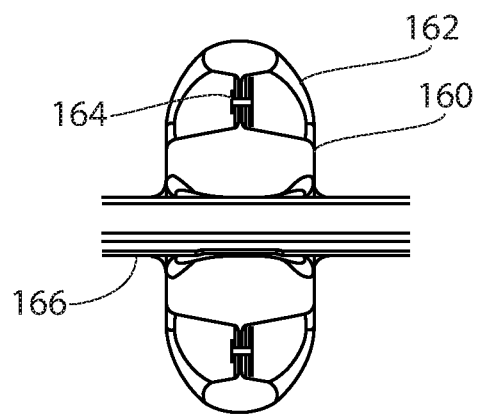
FIG. 31 shows a cross section through the balloon of FIG. 30.
Figure 32A:
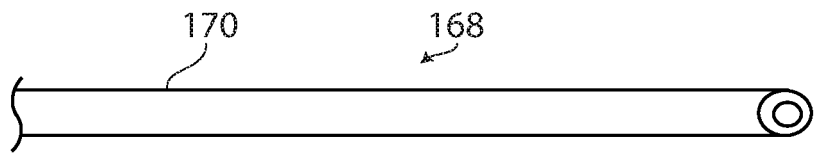
FIGS. 32A, 32B, 32C, 32D, 32E and 32F illustrate a cross sectional view of a sequential construction of an embodiment of the present disclosure including a balloon pocket and integral nose cone.
Figure 32B:
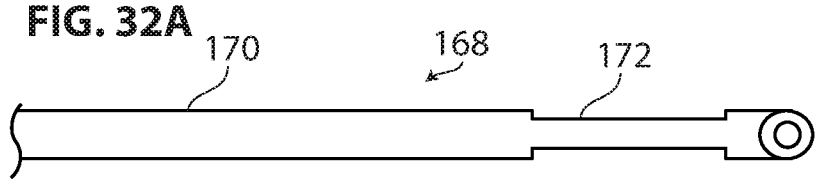
Figure 32C:
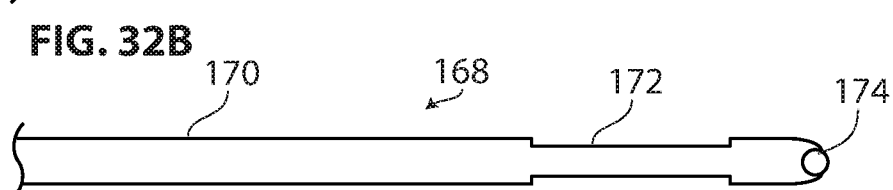
Figure 32D:
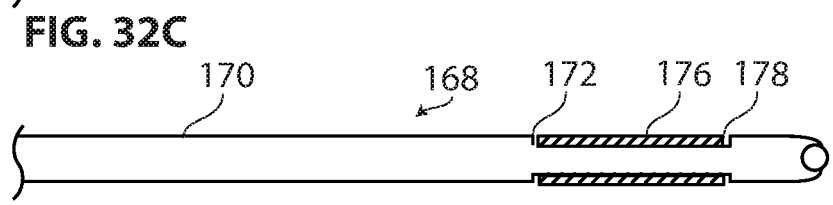
Figure 32E:
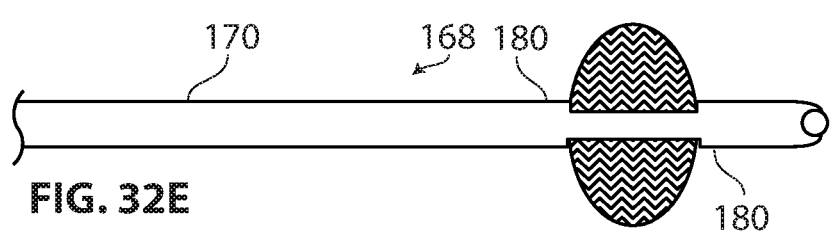
Figure 32F:
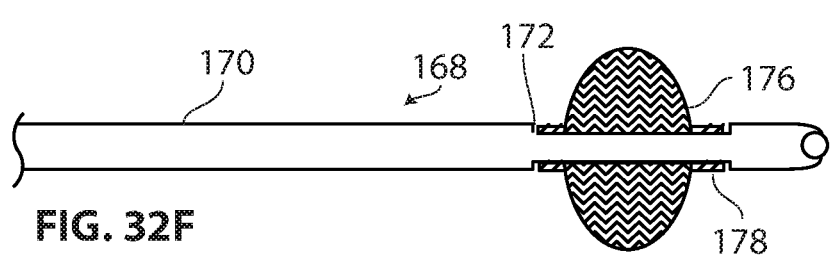

Referring to FIG. 31, a cross section of balloon 160 is shown with channels 162 and microvalves 164, positioned within channels 162.

FIG. 32 shows an example of a sequential assembly of an embodiment of the present disclosure. Referring to FIG. 32A, catheter 170 of device 168 is shown. FIG. 32B illustrates a first step in the construction of device 168 whereby a balloon pocket 172 is formed about a distal section of catheter 170 and a second step, as in FIG. 32C, whereby a rounded distal end 174 of catheter 170 is formed and a third step as in FIG. 32D whereby a balloon 176, with bonding tails 178 is disposed within pocket 172 of catheter 170 and a fourth optional step whereby catheter 170 or other material is reflowed at position 180 over balloon tails 178. FIG. 32F illustrates balloon 176 in its radially expanded configuration with balloon pocket 172 and tails 178 bonded in pocket 172 without being covered by reflow or other means.

Referring to FIG. 33, three alternate embodiments of the present disclosure are illustrated. FIG. 10A shows device 173 with catheter 181, balloon pocket 177, radially constrained balloon 178, catheter extension 171 and nose cone 182. FIG. 33B shows device 173 with radially expanded balloon 178 and bonding tails 183 bonded within balloon pocket 177. FIG. 33C illustrates device 175 with nosecone 182 and proximal bonding tail 191 reflowed into catheter 181 at position 179 and the distal balloon bonding tail 193 reflowed into or under nose cone 182 to catheter extension 171 at location 184. FIG. 33D illustrates device 179 with catheter 181, balloon 178, nose cone 182 and collar 186. Balloon 178 has a proximal tail 191 positioned under collar 186 and distal balloon tail 193 reflowed or bonded to catheter extension 171 and under nose cone 182 or into nose cone 182. FIG. 33E shows device 179 with balloon 178 expanded from within the balloon pocket formed between collar 186 and nose cone 182.

Figure 34:
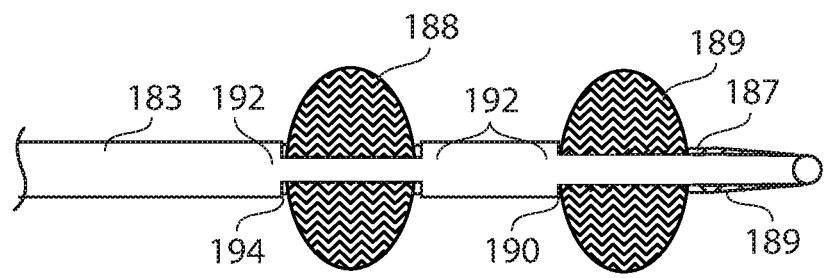
FIG. 34 illustrates an embodiment of the present disclosure with two balloons.

FIG. 34 shows yet another embodiment of the present disclosure with two balloons 188 and 189, catheter 183, balloon pockets 194 and 190, reflow areas 192 and nose cone 189. Although the example of FIG. 34 shows both balloon 188 and 189 positioned within pockets 194 and 190, only one balloon need be positioned within a pocket.

Figure 35:
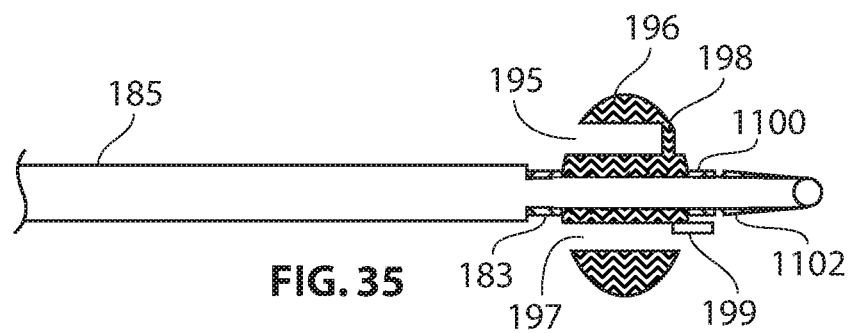
FIG. 35 illustrates an embodiment of the present disclosure including a balloon with valves.

FIG. 35 shows still another embodiment of the present disclosure with balloon 196 containing channels 195 and 197, valve 198 in the closed orientation, valve 199 in the open orientation, collar 183, nose cone 1102 and reflow area 1100. Although valve 198 is shown closed and valve 199 is shown open, they will typically act in unison and all either be simultaneously open or closed.

Figure 36:
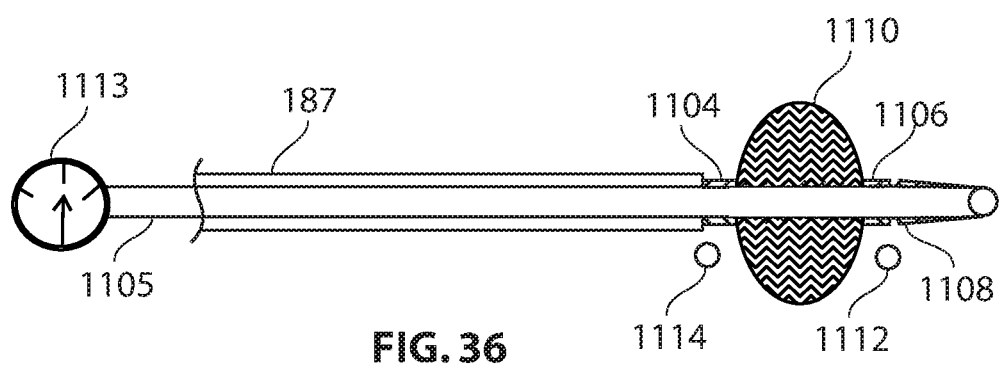
FIG. 36 illustrates an embodiment of the present disclosure with pressure sensors.

FIG. 36 shows still another embodiment of the present disclosure which includes two pressure sensors, positioned distal and proximal to balloon 1110, although a single pressure sensor positioned either distal or proximal to the balloon can be used. These pressure sensors can be used to monitor and, in conjunction with a syringe, control injection pressure either manually of by an automated means. Alternately pressure proximal or distal to the occlusion balloon can be measured through the catheter using an external pressure gauge (1113), the distal pressure being measured via the guidewire/injection lumen 1105 or any other catheter lumen or other tube. The pressure gauge can be connected to a pump, via a processor, allowing the pump to achieve a defined pressure or be programed to a specific set of pressures, volumes and/or flow rate as a function of time.

Referring to FIG. 37, four embodiments of balloon configurations are shown. FIG. 37A, shows device 1115 with balloon 1117 and catheter 1116. Balloon 117 in a radially expanded configuration, occupies only part of the circumference of catheter 1116. FIG. 37B illustrates device 1118 with catheter 1119 and balloons 1121 whereby the four balloons 1121, in radially expanded configurations are arranged circumferentially about catheter 1119, each occupying a part of the overall outer circumference of catheter 1119. FIG. 37C illustrates device 1123, with catheter 1125 and balloon 1127 in a radially expanded configuration, whereby balloon 1127, in a radially constrained configuration is positioned within a pocket of catheter 1125 and the radially outermost part of balloons 1127 is positioned approximately at or below the outer diameter of catheter 1125. FIG. 37D illustrates device 1131 with catheter 1135 and balloons 1137 in a radially expanded configuration, whereby balloons 1137, in a radially constrained configuration are positioned within a pocket of catheter 1135 and the radially outermost part of balloons 1137 are approximately positioned at or below the outer diameter of catheter 1135.

Figure 38A:
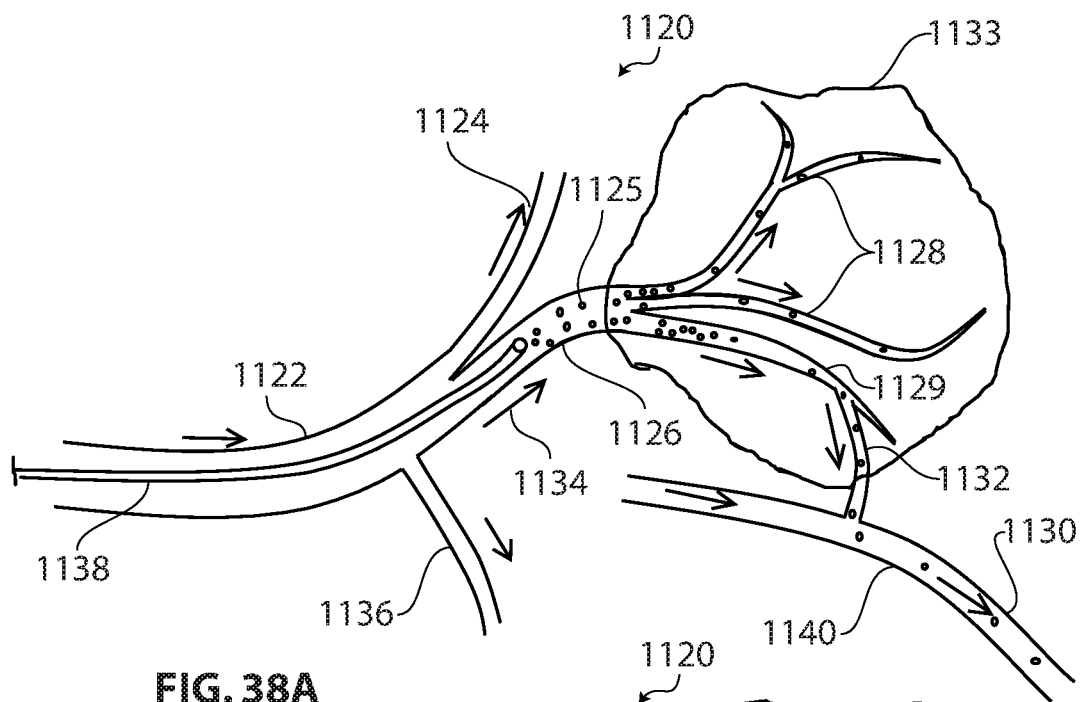
FIGS. 38A and 38B illustrate a tumor with vascular anatomy and embolization using a standard straight nose catheter.
Figure 38B:
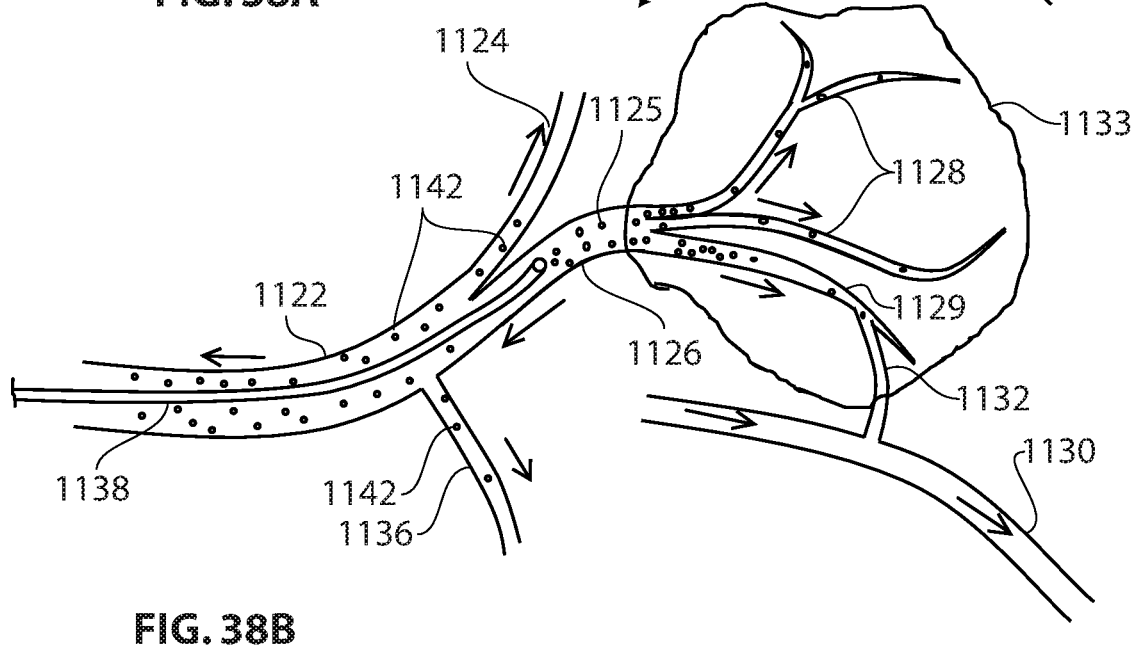

Referring to FIG. 38, an anatomical structure 1120 is shown with main artery 1122, right artery 1124, left artery 1126, right capillaries 1128, left capillary 1129, arterial side branch 1136, vein 1130, arteriovenus shunt 1132, tumor 1133, blood flow directional arrows 1134, standard straight tip catheter 1138, and embolization particles 1125. FIG. 38A illustrates the beginning of a transarterial embolization (TAE) procedure wherein the embolization particles 1125 are exiting the distal end of catheter 1138 and are carried by forward (antrograde) blood flow into tumor 1133 in a delivery method that is completely mediated by blood flow and normal blood pressure (flow mediated delivery). Capillary beds 1128 and 1129 of tumor 1133 begin to fill with embolic particles 1125 and arteriovenus shunt 1132 carries particles into vein 1130 causing anterograde reflux and non-target embolization. The flow through the areteriovenous shunt 1132 is rapid since the arterial pressure is significantly higher than venous pressure. Referring to FIG. 38B, continued injection of particles 1125 from the distal end of standard straight tip catheter 1138 results in the packing of particles and embolization of the distal ends of capillary beds 1128 and 1129. Distal capillary embolization causes the flow through arteriovenous shunt 1132 to stop and pressure to build in left artery 1126. As embolization progresses, the back pressure in artery 1126 continues to rise until embolic particles reflux in the retrograde direction 1142 causing non-target embolization of the right artery 1124, arterial side branch 1136 and main artery 1122. This situation can cause non-target embolization, loss of an unknown amount of particles, delivery of an unknown and irreproducible dose and non-optimal distribution of embolic particles in the tumor vasculature. In this instance, both anterograde and retrograded reflux can occur.

Figure 39A:
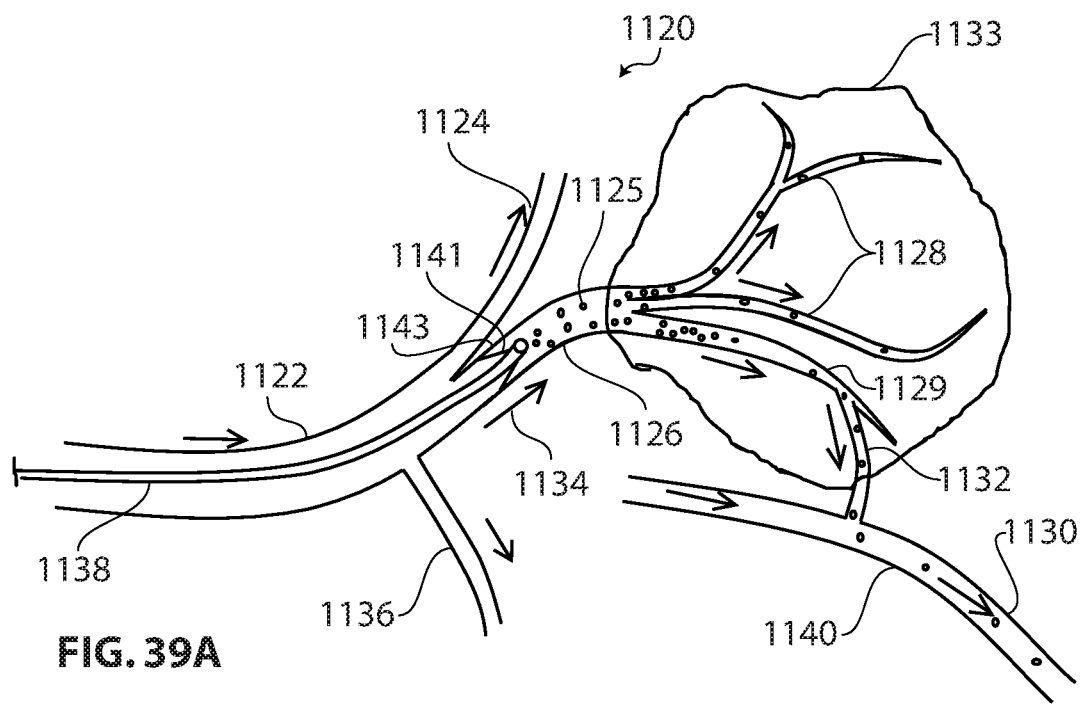
FIGS. 39A and 39B illustrate a tumor with vascular anatomy and embolization using a balloon including channels and valves.
Figure 39B:
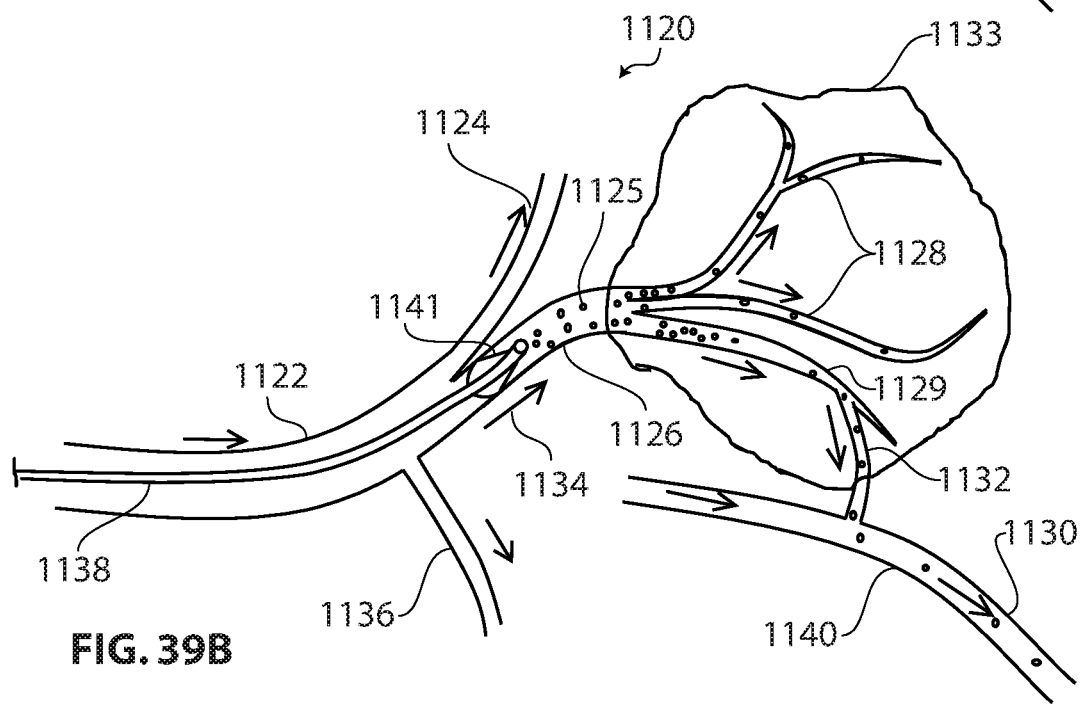
Figure 40A:
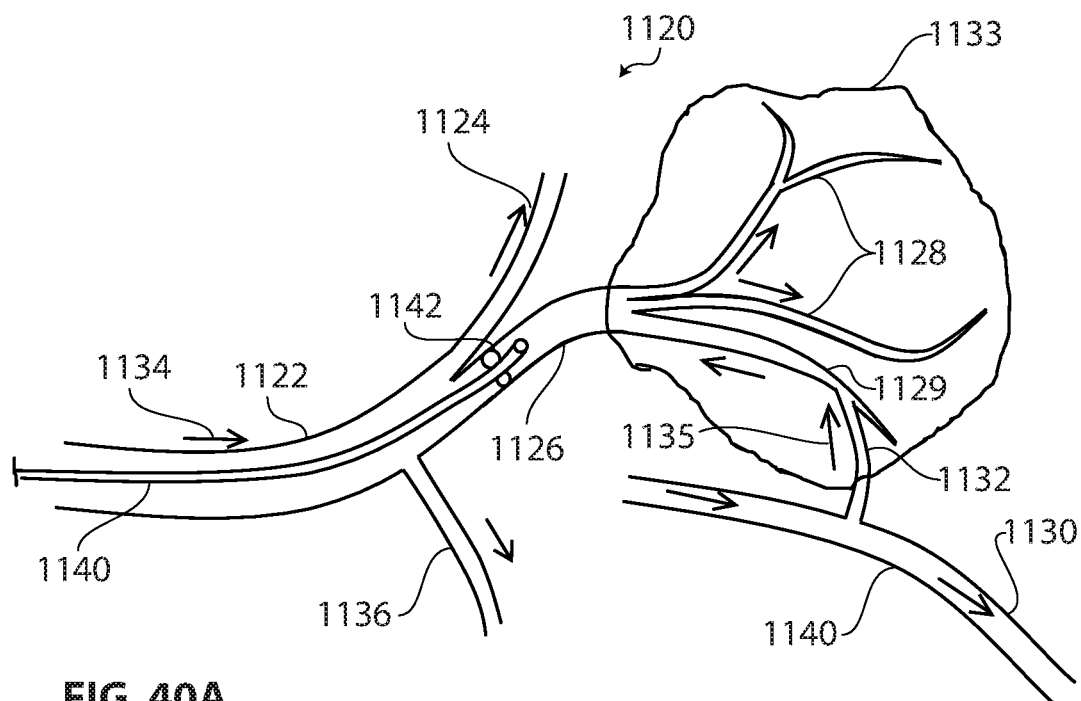
FIGS. 40A, 40B, 40C and 40D illustrate a tumor with vascular anatomy and embolization using an occlusion balloon.
Figure 40B:
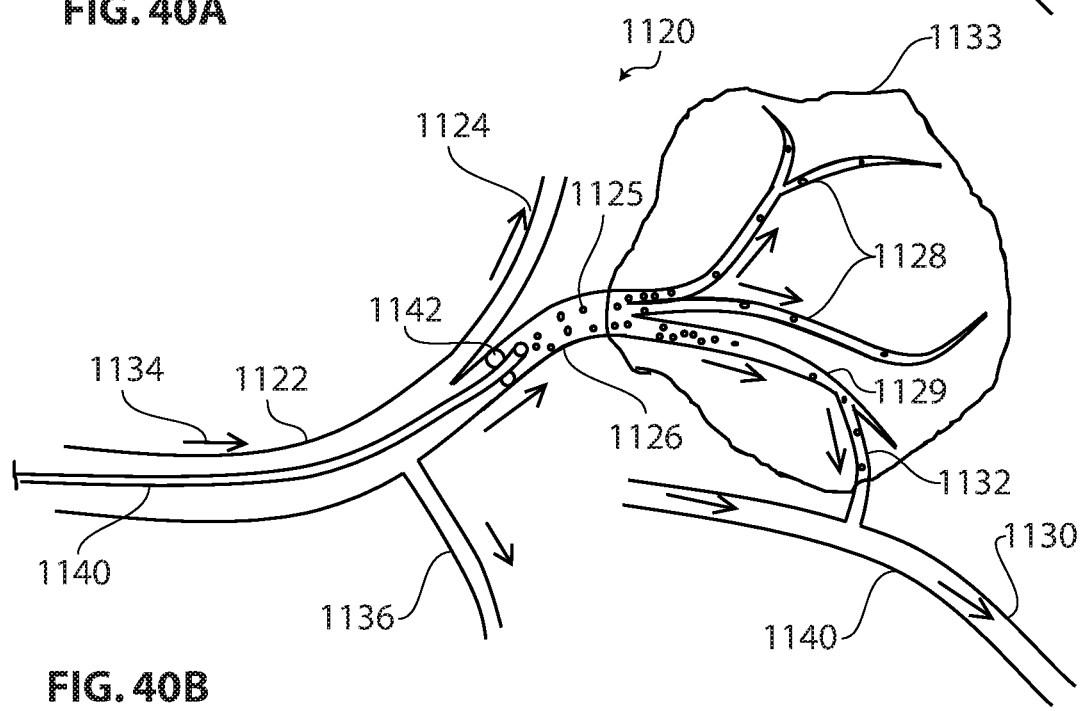
Figure 40C:
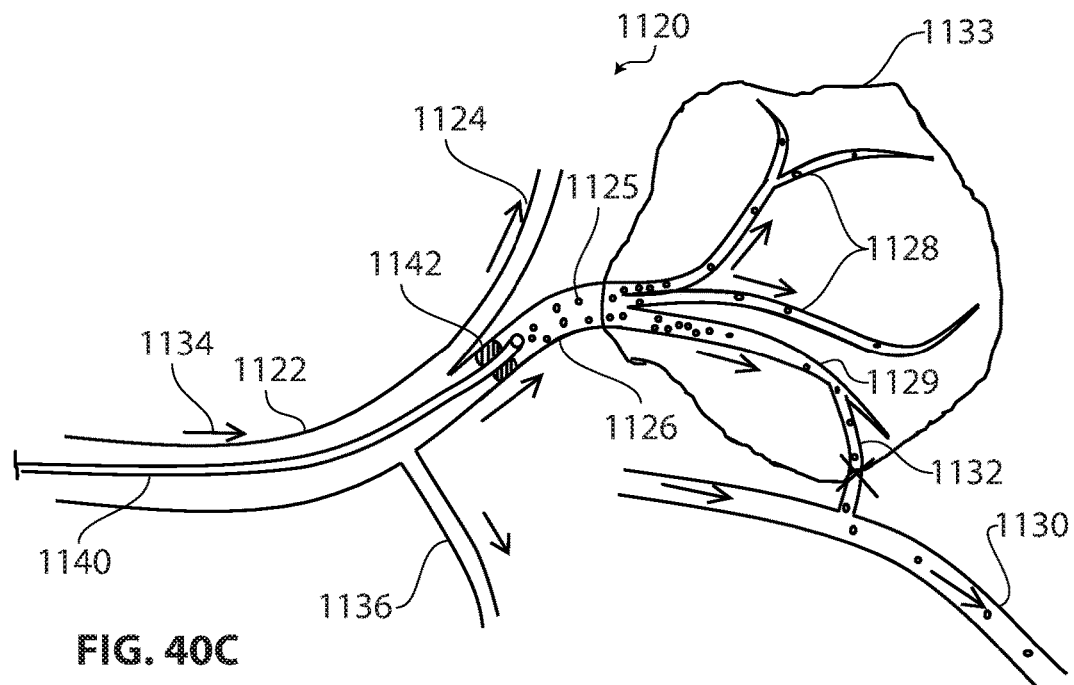
Figure 40D:
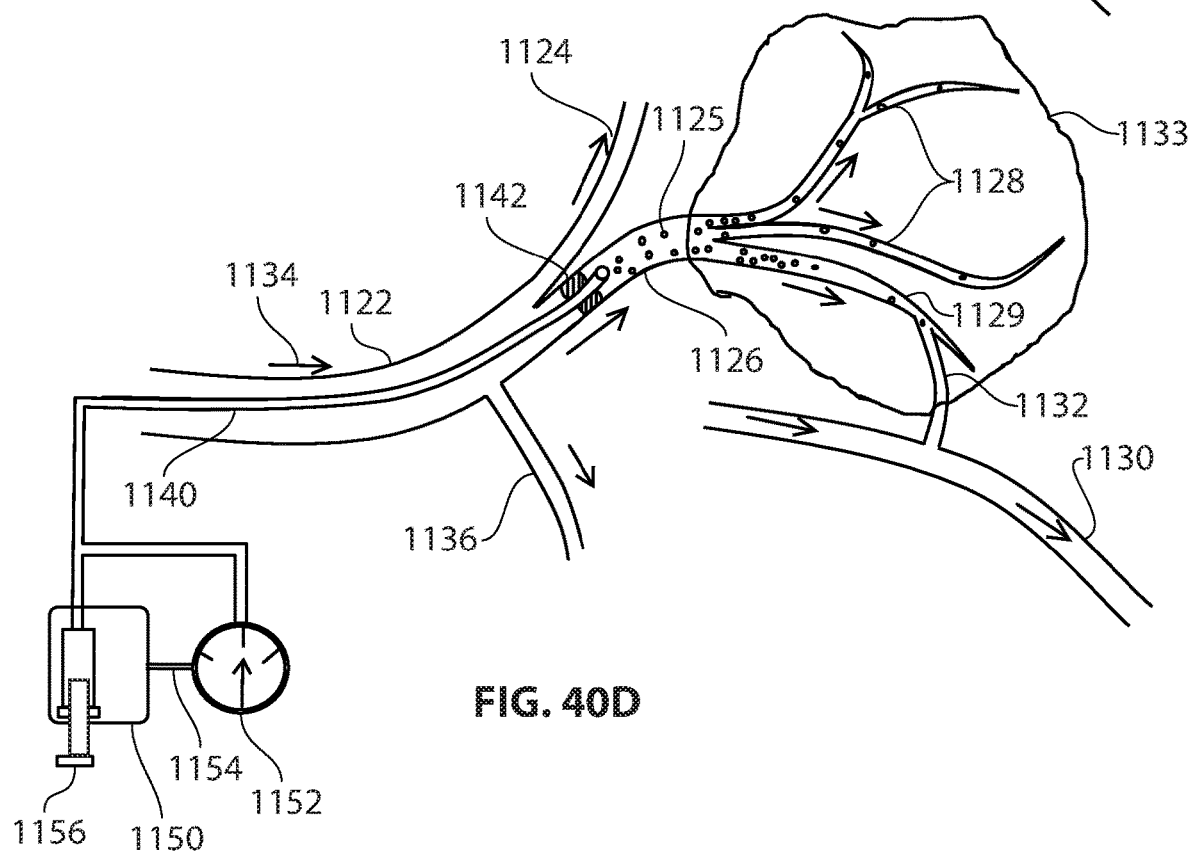

Referring to FIG. 39, anatomical structure 1120 is shown as in FIG. 38. In this instance, a balloon 1141, with channels 1143 and one-way valves (FIGS. 30 and 31) is positioned about the distal end of catheter 1139. Balloon 1141, so constructed, will allow only anterograde (normal) flow and prohibit retrograde flow. Referring to FIG. 39A, balloon 1141 is shown in its radially expanded configuration and blood is flowing through balloon channels 1143 as indicated by blood flow arrow 1134 and into the vasculature of tumor 1133. Embolic particles 1125 are released from the distal end of catheter 1139 and carried forward by blood flow into capillaries 1128 and 1129. Capillary beds 1128 and 1129 of tumor 1133 begin to fill with embolic particles 1125 and arteriovenus shunt 1132 carries particles into vein 1130 causing anterograde reflux and non-target embolization. The flow through the areteriovenous shunt 1132 is rapid since the arterial pressure is significantly higher than venous pressure. Referring to FIG. 39B, continued injection of particles 1125 from the distal end of balloon catheter 1139 results in the packing of particles and embolization of the distal ends of capillary beds 1128 and 1129. Distal capillary embolization causes the flow through arteriovenous shunt 1132 to stop and pressure to build in left artery 1126. As embolization progresses, the pressure in artery 1126 continues to rise, however the valves of balloon 1141 close and prohibit retrograde reflux. In this instance, continued injection will increase the packing pressure of particles 1125 and can increase packing density and increase flow into distal locations in the margins of a tumor or other structure thereby improving particle distribution throughout the target vasculature. As part of the present method, pressure distal to the balloon can be regulated between systolic and any pressure above systolic, provided that it is within a range that is safe for the patient. By way of example, injection pressure can be low at the onset of the embolization procedure and increased at some point thereafter to a pressure greater than systolic. Such a point may, for example, be chosen to coincide with the stoppage of flow through arteriovenous shunt 1132. This method may improve particle distribution and packing. Alternately, the injection pressure through catheter 1139 can be high at the onset, thereby forcing particles rapidly into the distal section of capillaries 1128 and 1129 and hasten embolization of arteriovenous shunt 1132, thereby reducing anterograde reflux. Alternately, according to this method, a low to high pressure gradient or a high to low pressure gradient can be used. The aim for the use of a pressure mediated delivery of particles is to optimize for a low level of anterograde reflux, substantial elimination of retrograde reflux, high particle distribution and high particle density. A pressure sensor as in FIG. 36 can be used on the proximal and/or distal side of balloon 1142 to monitor pressure and enable a selection of a procedural end point based on a definitive pressure reading.

Referring to FIG. 40, anatomical structure 1120 is shown as in FIG. 38. In this instance, an occlusion balloon 1142 is positioned about the distal end of catheter 1140. Referring to FIG. 40A, balloon 1142 of catheter 1140 is shown in a radially expanded configuration. Since expanded balloon 1142 completely occludes artery 1126, all arteries and capillaries distal to the balloon are isolated from the main artery 1122, right artery 1124 and side branch artery 1136 thereby causing blood pressure distal to the balloon to drop from approximately normal arterial pressure of about 80 mmHg to a pressure in the range of 0-50 mmHg. When this happens, blood flow through the arteriovenous shunt 1132 can reverse as shown by blood flow arrow 1135, or the anterograde flow slowed or stopped. Referring to FIG. 40B, initial injection of particles 1125 will be against a pressure, with a minimal anterograde flow or into a flow stasis. Retrograde pressure flow against the particle injection can result from the flow of venous blood from vein 1130, through arteriovenus shunt 1135 and into the arterial capillary 1129 or from arteriovenous capillary beds associated with capillaries 1128. As particles 1125 are injected, they fill capillaries 1128 and 1129; however, particles cannot easily flow through arteriovenous shunt 1132 because of the reversal or slowing of flow and pressure. Continued injection can result in embolization of the distal portion of capillary 1129 and blockage of arteriovenous shunt 1132 with concomitant reduction or elimination of anterograde reflux. Increasing injection pressure through catheter 1140 following embolization of arteriovenous shunt 1132, can result in a high levels of particle density and distribution. Alternately, according to this method, a gradient can be used. The profile of the pressure gradient can be any function of time and pressure including, but not limited to, a linear or step function from low to high, high to low, alternating high to low and low to high or any other function and can be administered manually, in a semi-automated manner or using a programmable delivery means. Alternately according to this method, a pressure sensor as in FIG. 36 can be used on the proximal and/or distal side of balloon 1142 to monitor pressure and select a procedural end point based on a definitive pressure reading. Referring now to FIG. 40D, the injection through catheter 1140 into tumor 1133 can be accomplished using an automated pump/pressure monitor system whereby the pressure distal to occlusion balloon 1142 is measured on gauge 1152, the pressure reading transferred through connection 1154 to pump 1150 which controls the injection of anti-tumor agents from syringe 1156. Pump 1150 can be controlled manually or programed to any function of flow rate, time and/or pressure. The endpoint can be selected at any desirable pressure.

The aim of the present method is to eliminate retrograde reflux, reduce or eliminate anterograde reflux, control the particle density and distribution, deliver an optimal dose, enable a defined pressure endpoint, improve efficacy and reduce toxicity.

Referring to FIG. 41A, a longitudinal cross section of a catheter is shown with proximal and distal ends, catheter body 204, distal tip 203 and proximally disposed hub 206. Catheter body 204 has two lumens that are in fluid communication with hub 206, a first lumen extending from port 208 of hub 6 to the distal tip 203 of catheter 204 whereby fluid can be injected from the proximal hub 206 and exit at the distal tip 203 of catheter 204 and a second lumen extending from port 210 of hub 206 to an intermediate location at some distance from the distal tip 203 of catheter 204, the second lumen adapted to communicate with a balloon for inflation and deflation.

Referring to FIG. 41B, a longitudinal cross section of a first embodiment of the present disclosure is shown with proximal and distal ends, catheter body 204, distal tip 203, and two layered occlusion balloon 214 with channels 205 and valves 207 and proximally located hub 206. Although balloon 214 is shown with two channels, each with a valve, balloon 214 can have 1, 2, 3, 4 or any number of channels and any number of valves or be without valves. In this instance, the valve configuration allows fluid to flow from the proximal side of balloon 214 to the distal side of balloon 214 and to restrict flow from the distal side of balloon 214 to the proximal side of balloon 214; however, the opposite valve orientation and flow direction is also part of the present disclosure. Catheter body 204 can have a diameter of between 1 Fr and 10 Fr, more typically 2 Fr to 5 Fr and a length of 10 cm to 250 cm, more typically 50 cm to 150 cm. Two layered occlusion balloon 214 can be from 1 mm to 30 mm in diameter, more typically 2 mm to 10 mm in diameter, in its radially expanded configuration.

Referring to FIG. 41C, an alternate embodiment of the device of the present disclosure is shown, having catheter body 218, distal tip 209, hub 206 and umbrella shaped occlusion structure 220. When in its radially expanded configuration, the occlusion structure will completely occlude the flow of the vessel. The umbrella shaped occlusion structure 220 is positioned at some distance from the distal end of catheter 216 and forms an umbrella shaped structure disposed circumferentially about catheter 216 with its outer diameter in contact with the vessel. Umbrella shaped occlusion structure 220 can be from 1 mm to 30 mm in diameter more typically 2 mm to 10 mm in diameter when in its radially expanded configuration and a longitudinal thickness of 0.25 mm to 10 mm, more typically 0.5 mm to 2 mm. Umbrella shaped occlusion structure 220 is shown with its closed end attached to the catheter distal to the open end of the V shape; however, it can be positioned in the opposite orientation or it can be positioned at a 90 degree angle with respect to catheter body 18.

Referring to FIG. 41D, device 222 of the present disclosure is shown having catheter 218, distal tip 209, hub 206, and a unidirectional umbrella occlusion structure 224 with channels 230 and valves 228. Occlusion structure 224 will allow proximal to distal flow and prevent distal to proximal flow.

Referring to FIG. 41E, device 232 is shown with catheter body 234, catheter distal extensions 235 and distal tip 211. Catheter extension 235 can have a diameter of 0.5 Fr to 5 Fr, more typically of 1 Fr to 3 Fr and can be absent or can be of any length, typically 2 mm to 30 mm, more typically from 5 mm to 20 mm.

Referring to FIG. 41F, a preferred embodiment of the present disclosure is shown with catheter body 237, catheter extension 235, distal tip 211, nose-piece 241 and two layered occlusion balloon 243 in its radially expanded configuration. In this instance, two layered occlusion balloon 243 is disposed within a pocket formed on distal catheter extension 235 and between the distal end of catheter body 237 and the proximal end of nose-piece 241. The nose piece can be a tapered nose cone, a distally rounded piece of tubing or catheter, a blunt tube or any structure with a diameter equal to less than the catheter body. When in the radially constrained configuration, the outer diameter of the two layered occlusion balloon 243 has an outside diameter that is about equal to the outer diameter of the catheter body 237.

Referring to FIG. 41G, yet another embodiment of device 245 of the present disclosure is shown, having catheter body 247, distal tip 234, nose-piece 241, proximal hub 206 and unidirectional umbrella shaped occlusion structure 224 with channels 230 and valves 228. In this instance, unidirectional umbrella occlusion structure 224 with channels 230 and valves 228 is disposed within a pocket formed on distal catheter extension 234 and between the distal end of catheter body 247 and the proximal end of nose-piece 241. The nose piece 241 can be a tapered nose cone, a radiopaque marker band, a distally rounded piece of tubing or catheter, a blunt tube or any structure of about equal diameter to the catheter body. When in the radially constrained configuration, the unidirectional umbrella shaped occlusion structure 224 has an outside diameter that is about equal to the outer diameter of the catheter body 247.

Referring to FIG. 42, four views of a preferred embodiment of the unidirectional occlusion structure of present disclosure is shown. FIG. 42A illustrates a two layered unidirectional occlusion structure 236 in its radially expanded configuration (also seen in FIGS. 41B and 41F), having a proximal end 238, a distal end 240, balloon 242, balloon sheath 244, channel 246, valve structure 250, outer balloon sheath tail 254, balloon tail 256, flow direction arrow 252 and flow exit 248. When occlusion structure 236 is disposed on a catheter as in FIG. 41F, fluid flows in the proximal to distal direction (anterograde) as indicated by arrow 252 through channel 246 and valve 250 and exits out the distal flow exit 248. The anterograde fluid pressure on the inner surface of balloon sheath 244 at the distal end of channel 246, causes distally directed displacement or deflection of the inner surface of balloon sheath 244 at valve 250, thus allowing fluid to pass through flow exit 248. When flow is reversed, fluid pressure on the outer distal surface of balloon sheath 244 at valve 250 causes the balloon sheath 244 to press against the distal surface of balloon 242, closing valve 250 and preventing retrograde flow. Placing the unidirectional occlusion structure 236 in the opposite direction on the catheter will result in distal to proximal flow and prohibit proximal to distal flow. Although the occlusion structure of FIG. 42A is shown with two layers including an inner balloon and an outer sheath, it is understood that the sheath need not be present and a balloon with channels from the proximal surface to the distal surface is considered part of the present disclosure. Balloon 242, including channels 246 can be formed by molding, extruding, vacuum forming or otherwise shaping a material to include the desired number and configuration of channels. Alternately, a standard balloon, including but not limited to, round or oval, can be modified to achieve proximal to distal channels. One method to modify a balloon is by forming longitudinal pleats circumferentially oriented, thereby forming V shaped channels that extend from the proximal surface of the balloon to the distal surface of the balloon. Placing a sheath over such a modified balloon in the same manner as described above would give the same result as the balloon shown in FIGS. 42A through 42D.

Figure 42A:
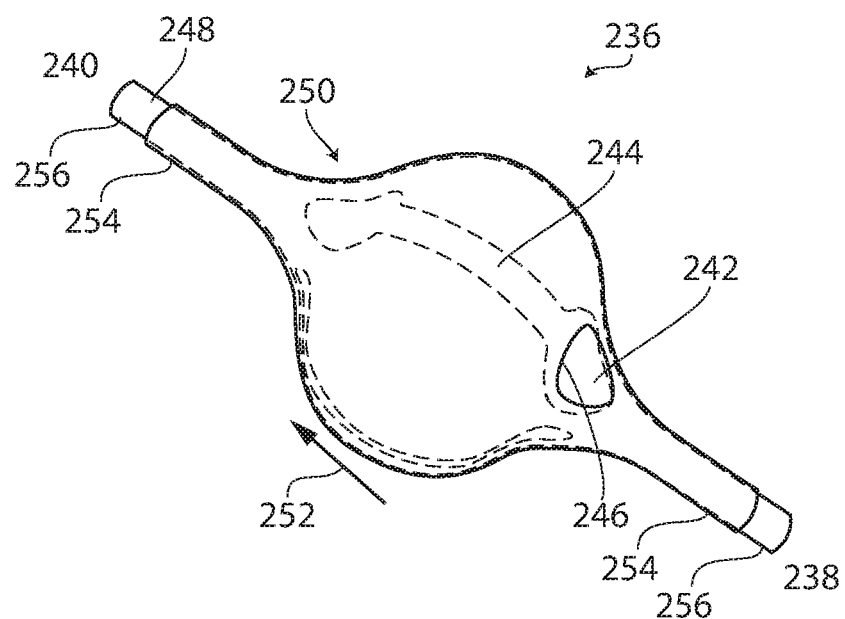
FIGS. 42A, 42B, 42C and 42D illustrate a two layer occlusion structure with unidirectional flow.
Figure 42B:
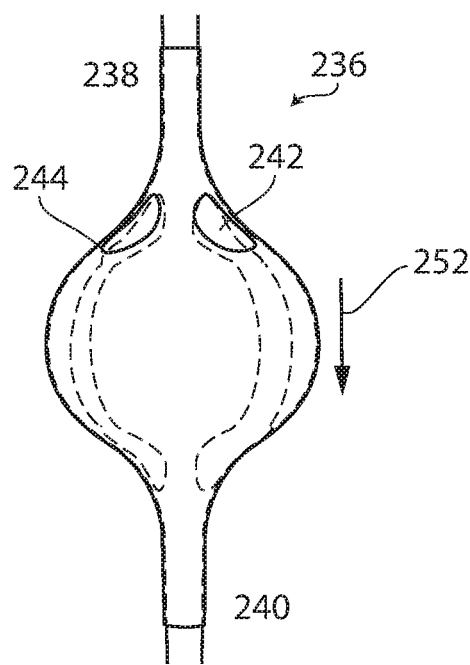

Referring to FIG. 42B, a side view of the unidirectional occlusion structure 236 of this disclosure is shown with proximal end 238 distal end 240, balloon 242, balloon sheath 244 and flow direction arrow 252.

Figure 42C:
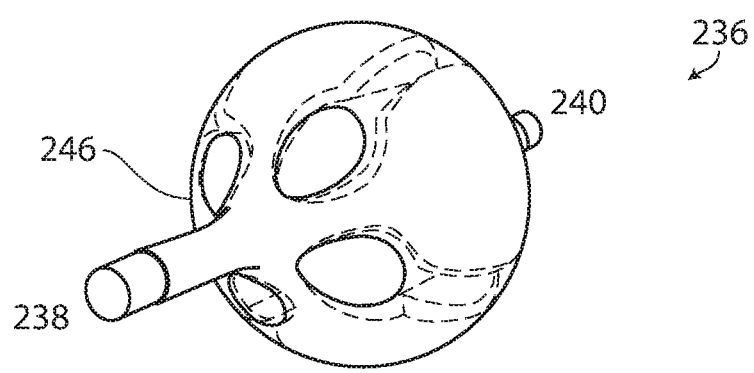

Referring to FIG. 42C, a proximal view of the unidirectional occlusion structure 236 is shown with proximal end 238, distal end 240 and channels 246.

Figure 42D:
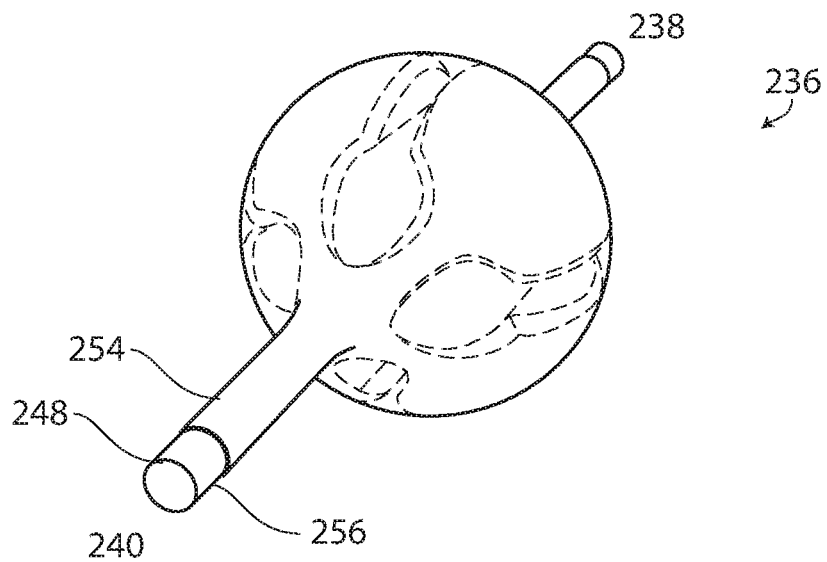

Referring to FIG. 42D, a distal surface view of the unidirectional occlusion structure 236 is shown with proximal end 238, distal end 240 and flow exit 248. Flow exit 248 is formed as a space between balloon tail 256 and balloon sheath 254. It is also possible to terminate balloon sheath 244 immediately below channels 246 forming a valve 250 that does not include balloon sheath tail 254.

Figure 43:
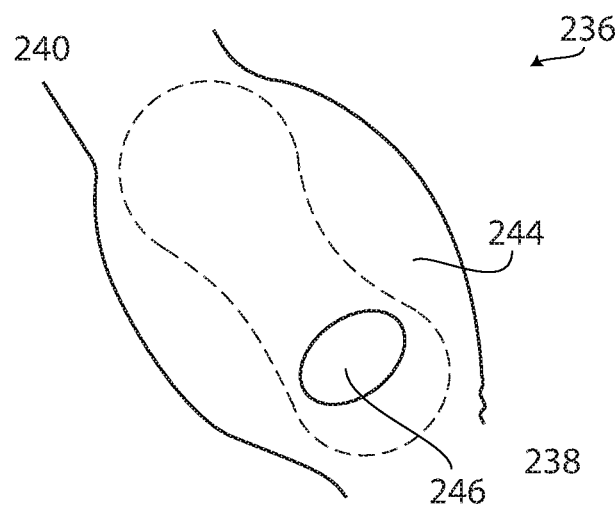
FIG. 43 illustrates a prototype of the occlusion structure of FIG. 42.

Referring to FIG. 43, an illustration of a prototype of the unidirectional occlusion structure 236 is shown in its radially expanded configuration with proximal end 238, distal end 240, balloon sheath 244, balloon 242 (positioned inside balloon sheath 244), and channel 246. This device was tested and will withstand at least 220 mmHg against its distal surface without retrograde flow.

Figure 44A:
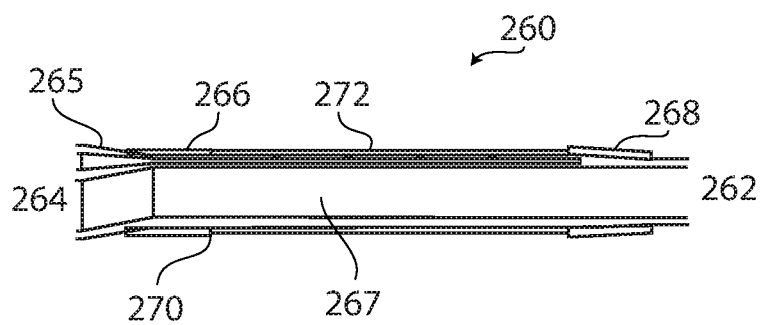
FIGS. 44A and 44B illustrate an embodiment of the present disclosure including a catheter with a pocket.

Referring to FIG. 44, device 60 illustrates the unidirectional occlusion structure 272 in a radially constrained configuration adapted to the distal extension 267 of a catheter 265 with distal end 262, proximal end 264, proximal collar 266, distal collar 268 (formed into a nose cone) and device pocket 270. Proximal collar 266 and distal collar 268 can comprise a metal, such as a radiopaque marker band, heat shrink tubing or any plastic material such as polyurethane, polyethylene, polystyrene, acetal, PTFE, nylon or the like, and can be 1 mm to 20 mm in length, more typically from 2 mm to 10 mm in length. In this instance, circumferentially oriented occlusion structure 272 is held within pocket 270 of catheter 265, with an outer diameter approximately equal to the outer diameter of catheter 265.

Figure 44B:
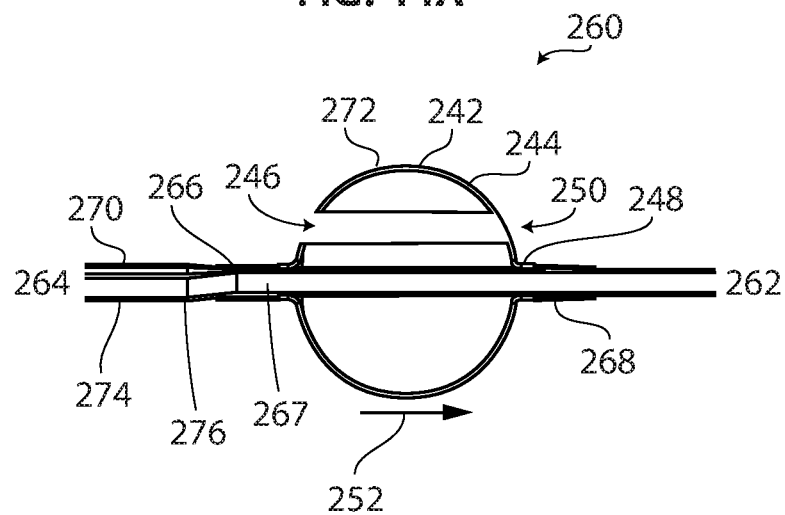

Referring to FIG. 44B, device 260 is shown with unidirectional occlusion structure 272 in its radially expanded configuration with proximal end 264, distal end 262, balloon 242, balloon sheath 244, valve 250, flow exit 248, channel 246, flow arrow 252, proximal collar 266, distal collar 268, catheter 274, balloon fill lumen 270 and guidewire/injection lumen 276. In this instance, there is no distal balloon sheath tail, the balloon sheath terminating on the balloon surface just below channel 246 and above the perimeter of catheter extension 267, thereby positioning the flow exit between the termination of the balloon sheath and the catheter.

Referring to FIG. 45A, device 280 is shown with catheter 282 and an umbrella shaped structure occlusion structure 2284 in its radially expanded configuration, whereby the umbrella shaped occlusion structure 284 is oriented circumferentially about catheter 282 such that its outer circumference is 360 degrees about catheter 282. When device 280 is placed in an artery or vein and umbrella shaped occlusion structure 284 is placed in its radially expanded configuration, the outer perimeter of occlusion device 284 will be at least in contact with the interior of the vessel wall and substantially occlude flow. FIG. 45A shows occlusion structure 284 in forward V orientation and FIG. 45B shows device 282 with the umbrella shaped occlusion device 288 in a reverse V configuration. The occlusion structure of the present disclosure can also have a 90 degree orientation with respect to the catheter when in its radially expanded configuration.

Referring to FIG. 46A, device 290 is shown with proximal end 292, distal end 294, catheter 296, two-way occlusion structure 299 in its radially expanded configuration, frame 298 and channels 2100, whereby fluid can flow from proximal to distal or distal to proximal through channels 2100. Although two channels are shown, two-way occlusion structure 298 can have 1, 2, 3 or any number of channels.

Referring to FIG. 46B, device 2102 is shown with proximal end 2104, distal end 2106, catheter 2108, and unidirectional umbrella shaped occlusion device 2110 comprising, frame 2111, channels 2112 and radial valve 2114, whereby fluid will flow from proximal to distal (anterograde) only, retrograde flow being prohibited by radial valve 2114. Although device 2102 will allow only anterograde flow, if desired, device 2110 of apparatus 2102 can be configured to allow only retrograde flow and/or have a forward V configuration as shown, or, if desired, a reverse V configuration or an orientation 90 degrees with respect to catheter 2108.

The frames 298 and 2111 of occlusion structure 2110 can be made of metal, such as shape memory metals nitinol or elgiloy, or plastic such as polyethylene, polyurethane, polystyrene, PTFE, acetal and nylon or elastic materials such as silicone or fabrics such as cotton and rayon and can include a mesh, a wire frame, a diaphragm and can be pleated or otherwise folded or can be any other convenient structure or material provided that it is of sufficient strength and porosity to occlude elevated vascular pressures and capable of integrating channels and valves. Valve 114 can be made from flexible or rigid plastics including polypropylene and polyurethane, elastomeric materials such as silicone and can have a configuration including a flap, sock, cone, duck bill and diaphragm or the like with a thickness of 1 mil to 50 mil, more typically 2 mil to 10 mil.

Referring to FIG. 47A, a distal surface view of a unidirectional occlusion structure 2120 of the present disclosure is illustrated with the catheter 2122 (extending forward), device frame 2124, radial valve 2125 and channels 2126 disposed under radial valve 2125. As shown, radial valve 2125 extends radially outward from catheter 290 and covers all four valves. Four channels are shown in this example; however, any number of channels can be used. This configuration allows flow from the proximal surface to the distal surface of unidirectional umbrella shaped occlusion structure 2120; however, the reverse flow is also possible.

FIG. 47B illustrates another embodiment of the present disclosure comprising unidirectional umbrella shaped occlusion structure 2128 with catheter 2130 (extending forward), device frame 2132, valves 2136 and channels 2134 disposed under valves 2136. In this instance, each channel has a separate valve and although four channels and valves are shown, the device of this disclosure can have any number of channels and valves limited only by the size of the valve and channel and the area of the frames 2124 and 2132. This unidirectional configuration allows flow from the proximal surface to the distal surface of umbrella shaped occlusion structure 2128; however, the opposite flow can be easily achieved by changing the flow direction of the valves or rotating the unidirectional occlusion device 180 degrees on catheters 2122 and 2130.

FIGS. 48A and 48B illustrate a prototype micro-valve 2140 configured from 5 mil polyurethane material. This device was tested and will restrain a fluid pressure of at least 220 mmHg applied against its distal surface.

Referring to FIG. 49A, device 2142 is shown with triangular shaped occlusion structure 2145 in its radially expanded configuration and adapted to catheter 2144 whereby the occlusion structure 2145 has frame 2146 oriented circumferentially about catheter 2144 such that its outer circumference comprises 360 degrees. When device 2142 is placed in an artery or vein, frame 2146 is placed in its radially expanded configuration and the outer perimeter of device frame 2146 will be at least in contact with the interior of the vessel wall and at least substantially occlude flow.

Referring to FIG. 49B, device 2148 is shown with catheter 2150 and a unidirectional triangular shaped occlusion structure 2151 comprising frame 2152, channels 2154 and radial valve 2158. Although reference has been made to a unidirectional occlusion valve with an umbrella shape or a triangular shape, it is understood that any shape including, but not limited to, rectangular, oval, conical, and round can be used. Yet another construction of a unidirectional occlusion structure is a dilation or occlusion balloon or any other medical balloon disposed with channels and valves, the valves extending from a proximal surface to a distal surface.

Referring now to FIG. 50A to 50C, a method of deploying an occlusion structure 2191 from a radially constrained configuration to a radially expanded configuration and then returning it to the constrained configuration is shown. FIG. 50A shows a longitudinal cross section of device 2180 with a proximal end 2182, a distal end 2184, outer catheter 2186, inner catheter 2188, nose cone 2190 and radially constrained unidirectional occlusion structure 2191 with frame 2192, valve 2194, and frame attachment point 2196. Unidirectional occlusion structure 2191 is attached to inner catheter 2188 at attachment point 2196 whereby occlusion device 2191 is preloaded with a force which encourages its distal end to pivot proximally outward at attachment point 2196. In this instance, the outer catheter 2186 constrains occlusion structure 2191 against the preloaded force. Device 2180 is first positioned in the vasculature at or in the vicinity of a target structure.

Referring to FIG. 50B, outer catheter 2186 is retracted proximally as shown by arrow 2200 while the inner catheter 2188 is held stationary, thereby removing the constraint on occlusion structure 2191, allowing it to pivot outward and in a proximal direction at attachment point 2196 and into its radially expanded configuration. Frame 2192 can be made from a memory metal such as nitinol or elgiloy and preformed at attachment point 2196 to the radially expanded configuration thereby pre-loading an outward force on occlusion structure 2191 as it is moved to its radially constrained configuration. If a braided nitinol tube is used, it can be pre-formed into a radially expanded configuration whereby occlusion structure 2191 is oriented circumferentially about catheter 2144 with an outer circumference of 360 degrees. As in this example, the mesh can be coated with polyurethane, PTFE, silicone or the like and channels formed through the mesh and valves placed over the channels.

Referring to FIG. 50C, outer catheter 2186 is retracted distally while holding inner catheter 2188 stationary thereby pivoting frame 2192 distally at attachment point 2198 and placing occlusion structure 2191 in its radially constrained configuration.

Referring to FIG. 51, an anatomical structure 2200 is shown with main artery 2202, right artery 2204, left artery 2206, capillaries 2208, tumor 2209 and blood flow directional arrows 2212. FIGS. 51A-51E illustrates a method of the present disclosure wherein a tumor is embolized with drug eluting beads as in Transarterial Chemoembolization (TACE).

Figure 51A:
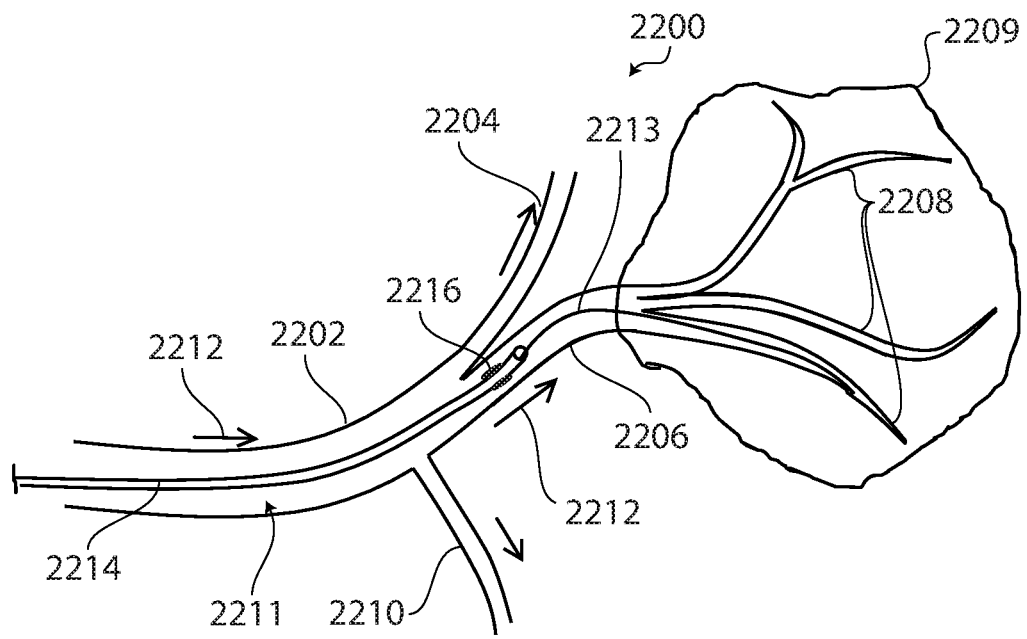
FIGS. 51A, 51B, 51C, 51D, 51E and 51F illustrate a method for delivery of embolic particles using a device of the present disclosure.

In a first step, device 2211, comprising a two lumen catheter 2214 and a radially constrained unidirectional balloon occlusion structure 2216 (also in FIG. 42), is advanced over a guidewire 2213 using lumen one (guidewire/injection lumen) of catheter 2214 from an entry point on the surface of the body, usually the femoral artery at the groin, and positioned at, or in the vicinity of, an artery feeding a tumor as in FIG. 51A. As indicated by arrows 2212, the blood flows in an anterograde direction over device 2211 and into capillaries 2208 of tumor 2209.

Figure 51B:
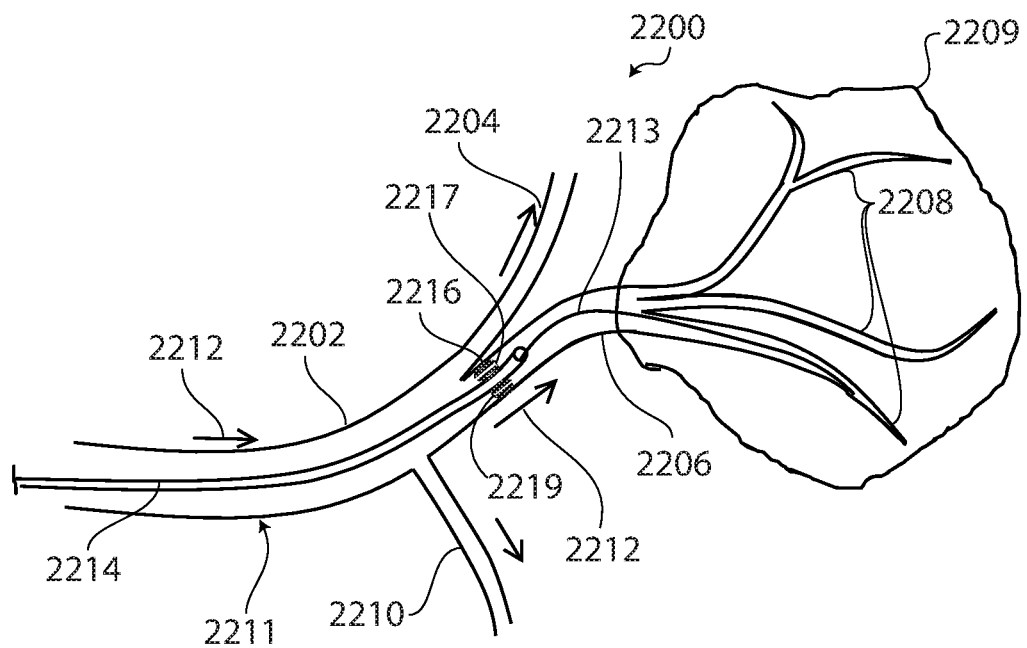

In a second step, the unidirectional balloon occlusion structure 2216 is placed in a radially expanded configuration by inflating the inner balloon of the two layered device of FIG. 42 using the second lumen of catheter 2214 (balloon inflation lumen) as seen in anatomical FIG. 51B. When placed in a radially expanded configuration, normal blood pressure between about 80 mmHg and 130 mmHg urges valves 2217 of occlusion structure 2216 to the open position, thereby allowing anterograde blood flow through channels 2219 and into the capillaries 2208 of tumor 2209.

Figure 51C:
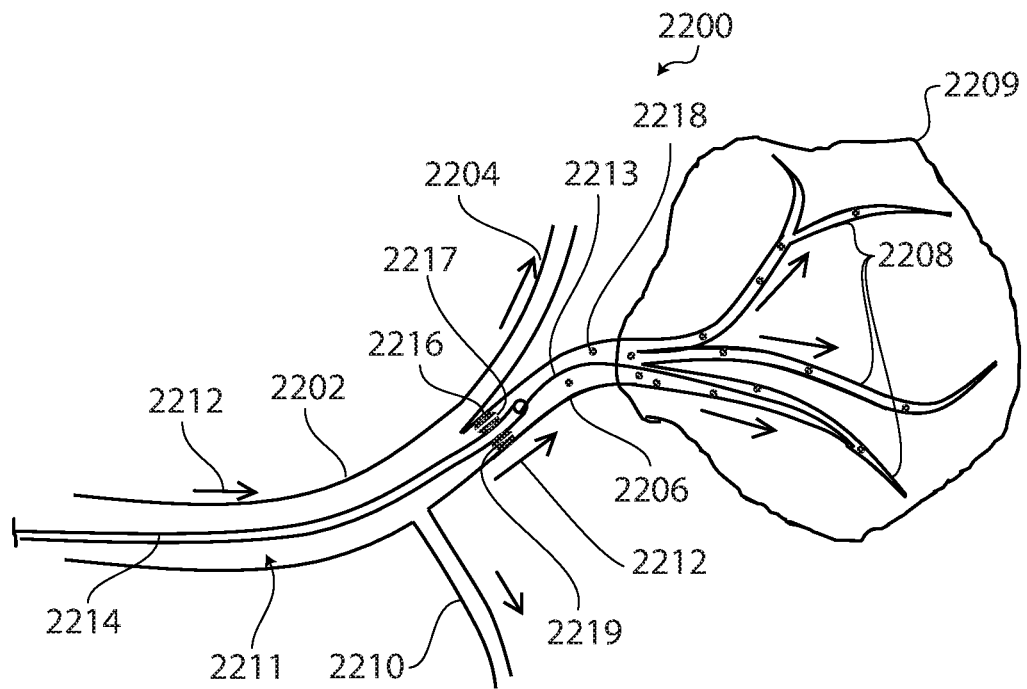

FIG. 51C illustrates a third step whereby chemoembolization particles 2218 are beginning to be injected into left artery 2206 and capillaries 2208 of tumor 209. At this point, valves 2217 of unidirectional occlusion structure 2216 are in the open position and blood is flowing in the anterograde direction through channels 2219 which continues to carry chemoembolization particles 2218 into the vasculature of tumor 2209.

Figure 51D:
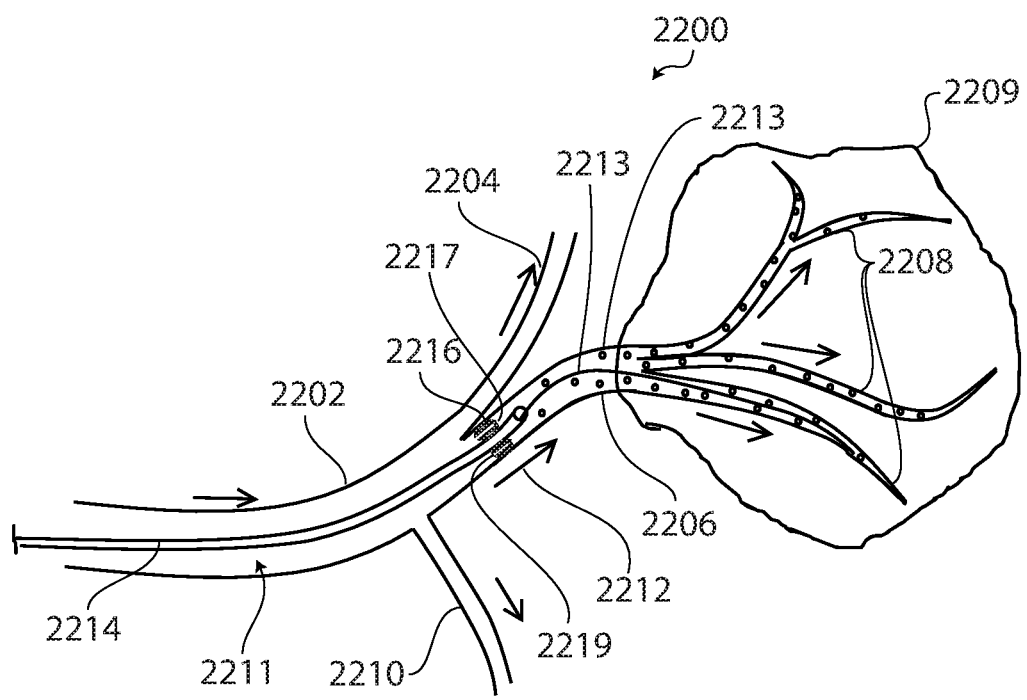

Referring to FIG. 51D, a fourth step is illustrated whereby chemoembolization particles 2218 begin to embolize the distal ends of capillaries 2208, increasing pressure in the proximal section of capillaries 2208 and left artery 2206. This back pressure causes blood flow and chemoembolization particles 2218 to flow in a retrograde direction; however, the back-pressure in left artery 2206 urges valves 2217 to close, thereby maintaining particles 2218 in the vascular compartment distal to occlusion device 2217. Using currently available straight tip catheters, the chemoembolization procedure would be terminated at this point since particles would reflux backward over the catheter and into the general circulation causing non-target embolization and associated complications.

Figure 51E:
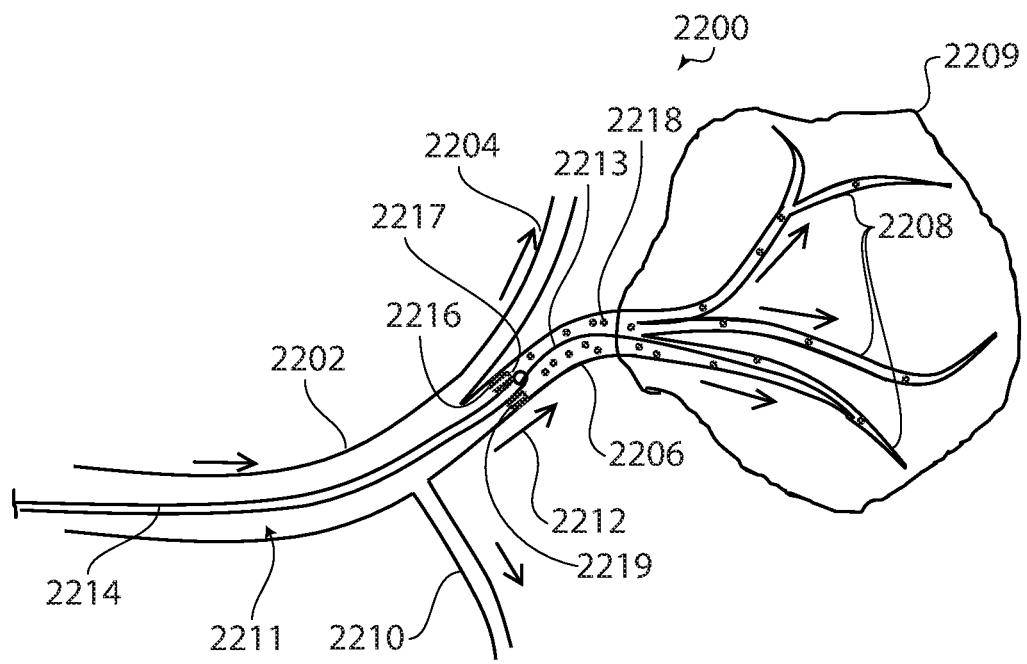

FIG. 51E illustrates a fifth step, not possible using present catheters, whereby embolization particles continue to be injected, without retrograde reflux, and further fill the vasculature of the tumor with particles 2218. This method can both prevent the complications associated with retrograde reflux and allow more particles to enter the tumor.

Figure 51F:
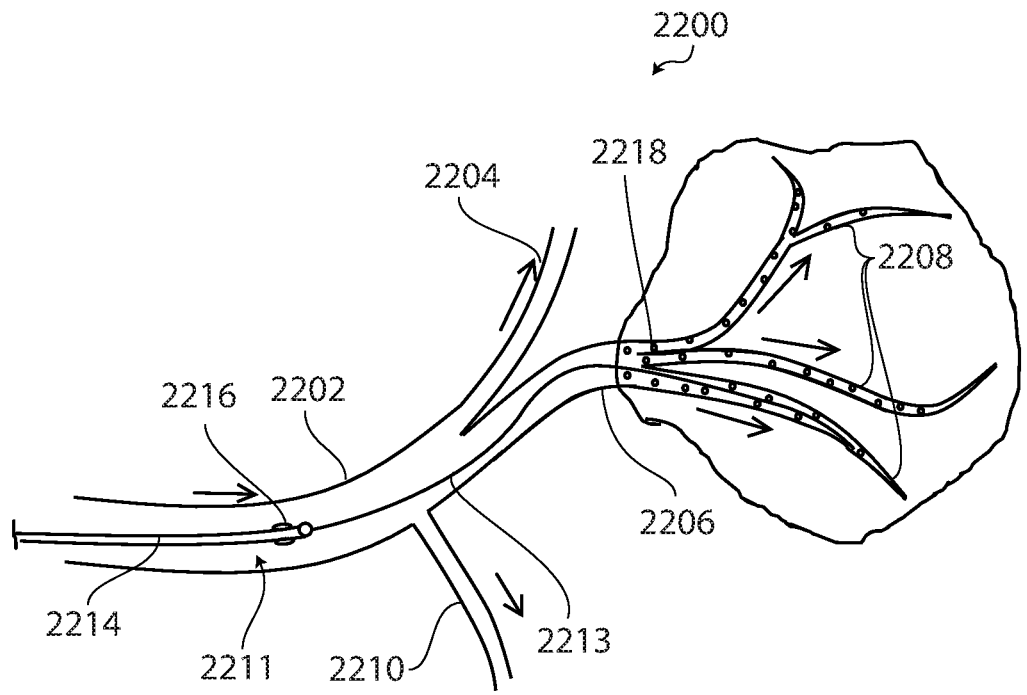

FIG. 51F is a final step in the present method whereby occlusion structure 2216 is placed in a radially constrained configuration and device 2211 is withdrawn from the body over guidewire 2213.

Although particular mention has been given to a device that is capable of transitioning from a radially constrained configuration to a radially expanded configuration, such a transition is not required. A unidirectional occlusion structure of the present disclosure can be configured in a permanently expanded configuration. In this instance, the occlusion structure may be a highly flexible material such as a low durometer plastic or rubber or a flexible mesh or any material or construction that provides sufficient strength and flexibility to navigate through vasculature and to a target and provide unidirectional occlusion.

Figure 52:
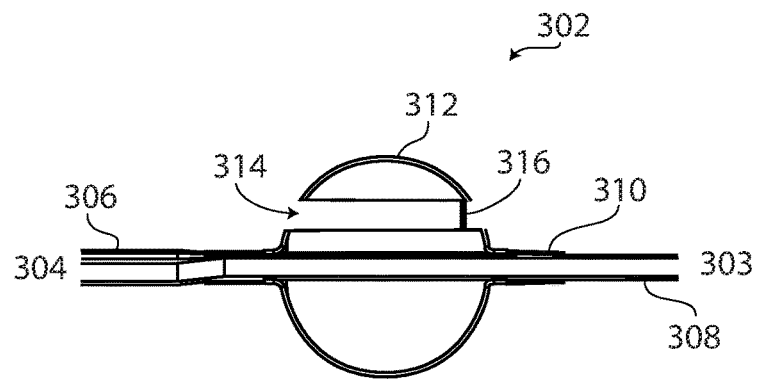
FIG. 52 illustrates a partial occlusion balloon with channel and valve.

Referring to FIG. 52, distal section 302 of a device is shown with distal end 303, proximal end 304, catheter body 306, distal tip 308, nose cone 310, partial occlusion balloon 312 in a fully expanded configuration, channel 314 and one-way valve 316. In this embodiment, flow is permitted in the proximal to distal direction through channel 314 and restricted, by one-way valve 316 to flow proximally. Partial occlusion balloon 312 can be any shape and diameters from 1 mm to 30 mm more typically from 2 mm to 10 mm.

Figure 53:
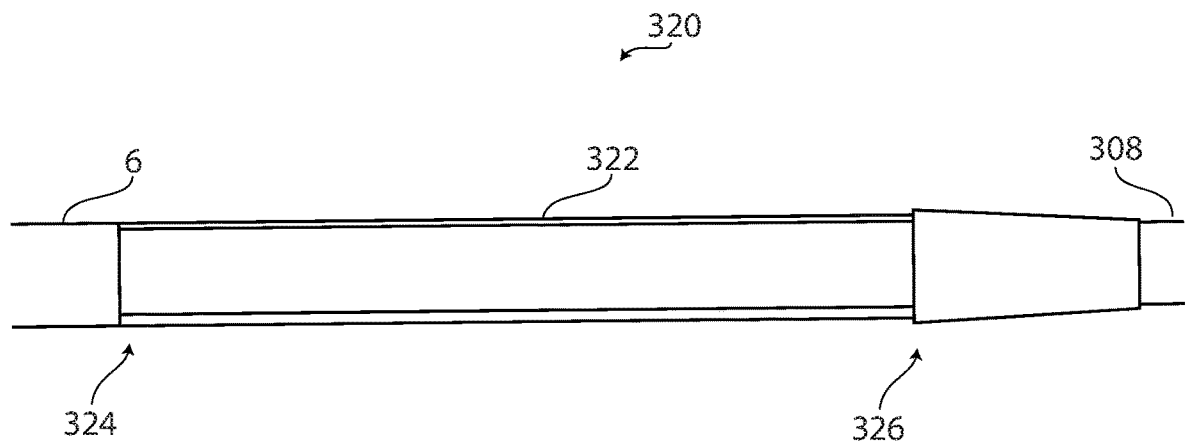
FIG. 53 illustrates a side view of constrained occlusion balloon in catheter pocket.

Referring to FIG. 53, a longitudinal section 320 of a distal section of the device of the present disclosure is shown with catheter body 306 distal tip 308, nose cone 310, radially constrained balloon 322, proximal balloon pocket boundary 324 and distal balloon pocket boundary 326. Radially constrained balloon 322 sits within the pocket defined by the distal end of catheter 306 at boundary 324 and the proximal end of nosecone 310 at boundary 326. The outer diameter of the constrained balloon is approximately equal to the outer diameter of catheter body 306. This allows the balloon to sit within the pocket and maintain the catheter at a desirable minimal diameter.

Referring to FIG. 54A, a distal section 330 of the device of the present disclosure is shown with catheter body 306, catheter extension 307, distal tip 308, nose cone 310, balloon pocket 332, guidewire and injection lumen 334 and balloon inflation lumen 336. The catheter body 306 has a diameter of 0.25 mm to 5 mm, more typically from 0.5 mm to 1.5 mm and a length of 10 cm to 240 cm more typically from 75 cm to 150 cm. The catheter extension 307 has a diameter of 0.25 mm to 3 mm more typically from 0.4 mm to 1 mm and a length of 5 mm to 100 mm more typically from 5 mm to 40 mm. The balloon pocket 332 has a depth equal to the difference in diameter of the catheter body 306 and the catheter extension 307 and a length of 1 mm to 50 mm more typically from 5 mm to 15 mm. The balloon wall thickness and inner diameter are selected, extruded or molded to fit into balloon pocket 332 with minimal balloon extending above of balloon pocket 332.

Referring to FIG. 54B, distal section 330 includes a balloon 338 in a radially constrained configuration held within balloon pocket 332 and having an outer diameter approximately equal to the outer diameter of catheter body 306.

Referring to FIG. 54C, distal section 330 includes balloon 338 in a radially expanded configuration with channels 314 and one-way valves 316 in a closed orientation. Partial occlusion balloon 338 can be any shape and diameters from 1 mm to 30 mm more typically from 2 mm to 10 mm and a length of 1 mm to 50 mm more typically from 5 mm to 15 mm. Channels 314 can be of any shape and configuration and an opening that is calibrated to the desired flow therethrough. In a preferred embodiment, the balloon will have a diameter of 6 mm and a channel diameter of 0.5 mm to 1.5 mm. Balloon 338, including channels 314 can be formed by molding, extruding, vacuum forming or otherwise shaping a material to include the desired number and configuration of channels. Alternately, a standard balloon, including but not limited to, round or oval, can be modified to achieve proximal to distal channels. One method to modify a balloon is by forming longitudinal pleats circumferentially oriented; thereby forming V shaped channels that extend from the proximal end of the balloon to the distal end of the balloon. Placing a sheath or film over such a modified balloon results in longitudinal channels and a one way valve as described in co-pending application 61/917,131.

Referring to FIG. 55A through 55C, a serial construction of the device of the present disclosure is illustrated.

Referring to FIG. 55A, a longitudinal view of device construction 350 with catheter body 306, distally located catheter extension 307 and proximally located hub 352 comprising guidewire and injection port 354 and balloon inflation/deflation port 356.

Referring to FIG. 55B, a longitudinal view of a device construction 350 is shown with added nose cone 310 and balloon pocket positioned between the distal end of catheter body 306 and the proximal end of nose cone 310.

Referring to FIG. 55C, a longitudinal view of the device 358 of the present disclosure is shown with catheter body 306, balloon 340 and hub 352. Balloon 340 is shown in a radially expanded configuration with channels 314 and valves 316 in the open position.

Figure 56:
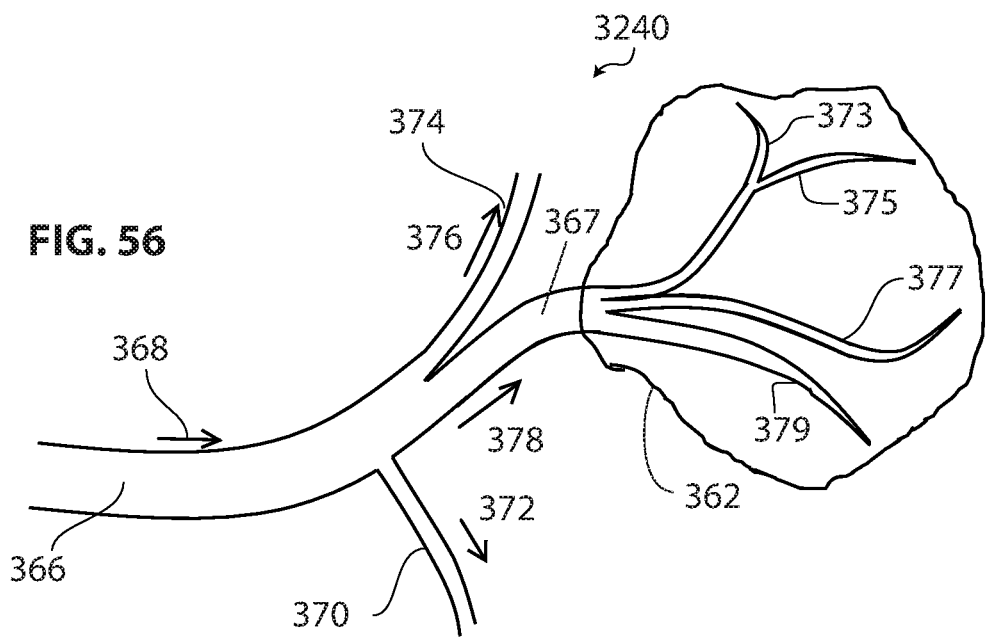
FIG. 56 illustrates liver vasculature and associated tumor vasculature.

Referring to FIG. 56, an anatomical structure 360 is shown with tumor 362, main artery 366, distal main artery 367, side branch arteries 370 and 374, tumor capillaries 373, 375, 377 and 379 and blood flow direction arrows 368, 372, 376 and 378. In the case of a tumor in the right liver lobe, artery 366 is the right hepatic artery and 367 is the distal right hepatic artery which flow toward the tumor as seen by flow direction arrow 368 and 378. In this instance, artery 370 is the gastroduodenal artery and artery 374 is a hepatoenteric artery such as the superduodenal artery, the normal flow of both is away from the hepatic artery, as shown by flow direction arrows 372 and 376, and into arterial networks which supply both the liver and gastrointestinal tract. Blood from the hepatic artery 366 also flows into the tumor capillaries 373, 375, 377, and 379. Normal blood flow through the right hepatic artery is in the range of 4 ml/sec.

Referring to FIG. 57A through 57H, a tumor embolization method according to current medial practice is shown. At least some of the steps shown are used in current catheter based embolization therapy in tumors of the liver The first step of the procedure is to advance guidewire 382 from the femoral artery at the groin, through the iliac artery, aorta, celiac artery, hepatic artery and into the right hepatic artery 366 as in anatomical structure 380 of FIG. 57A. The diameter of guidewire 382 is typically from about 0.25 mm to 1.25 mm more typically from 0.4 mm to 1 mm.

Figure 57A:
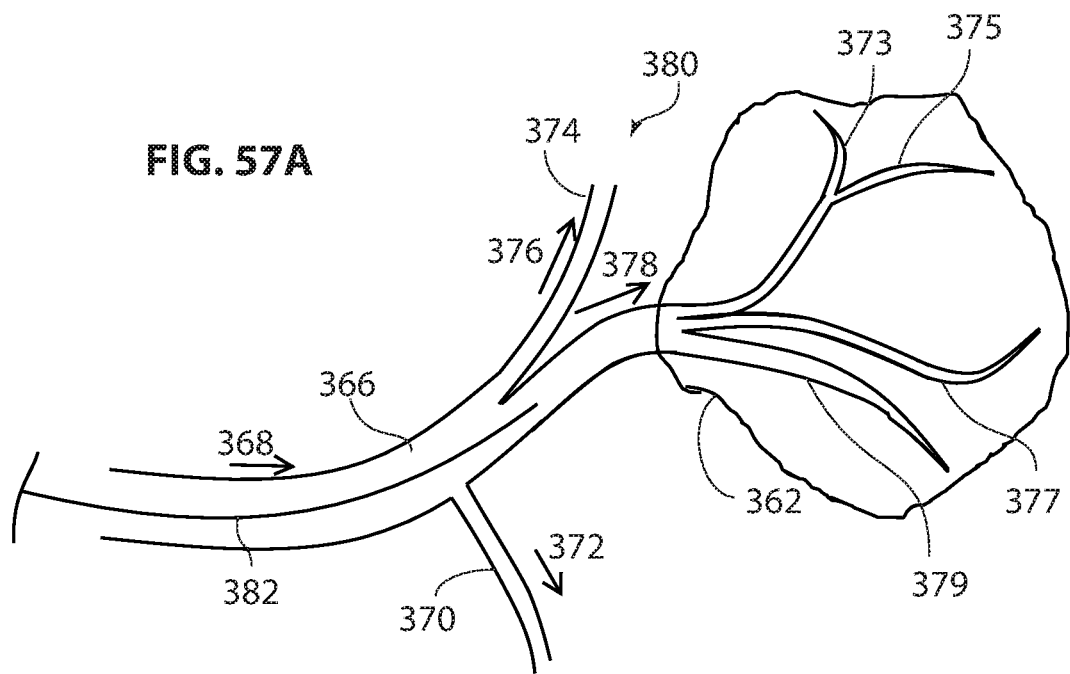
Figure 57B:
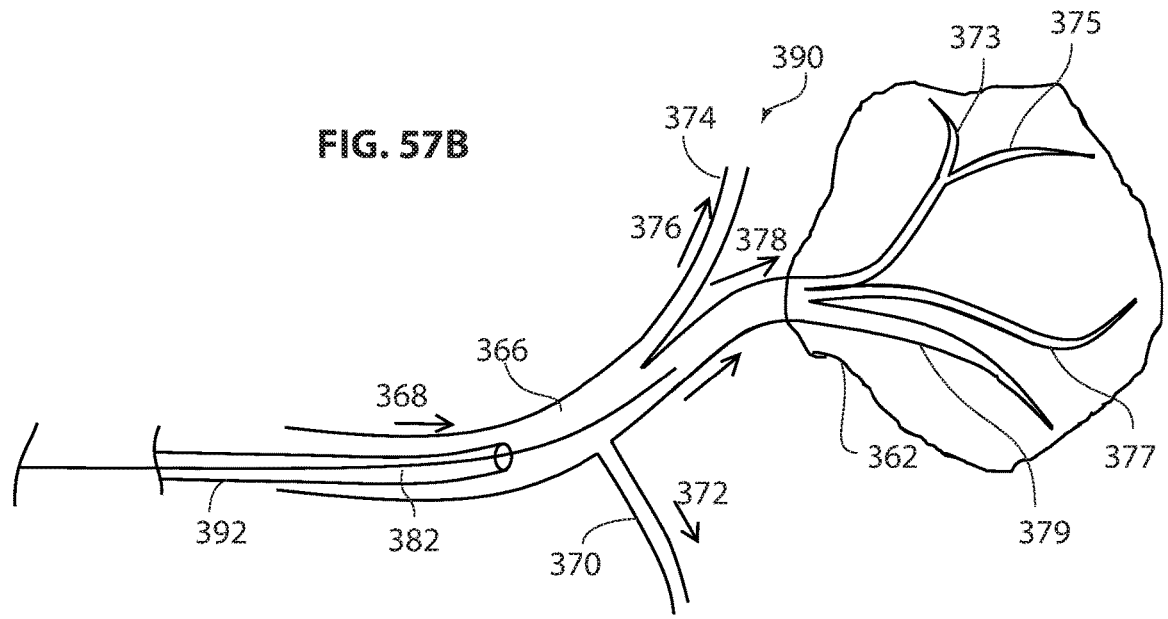

In the second step of the procedure, illustrated in FIG. 57B, guide-catheter 392 is advanced over guidewire 382 and along the same arterial path as for guidewire 382. Typically, the guide catheter has an outer diameter of about 1.5 mm to 2.5 mm and has a central lumen that can accept a microcatheter with an outer diameter of 0.5 mm to 1.5 mm. The guide catheter is too large to access the vasculature in the vicinity of the tumor and is typically advanced as far along the vascular path toward the tumor as possible. The blood flow follows the same normal pattern as in FIG. 56 and flows around the sides of guide catheter 392.

Figure 57C:
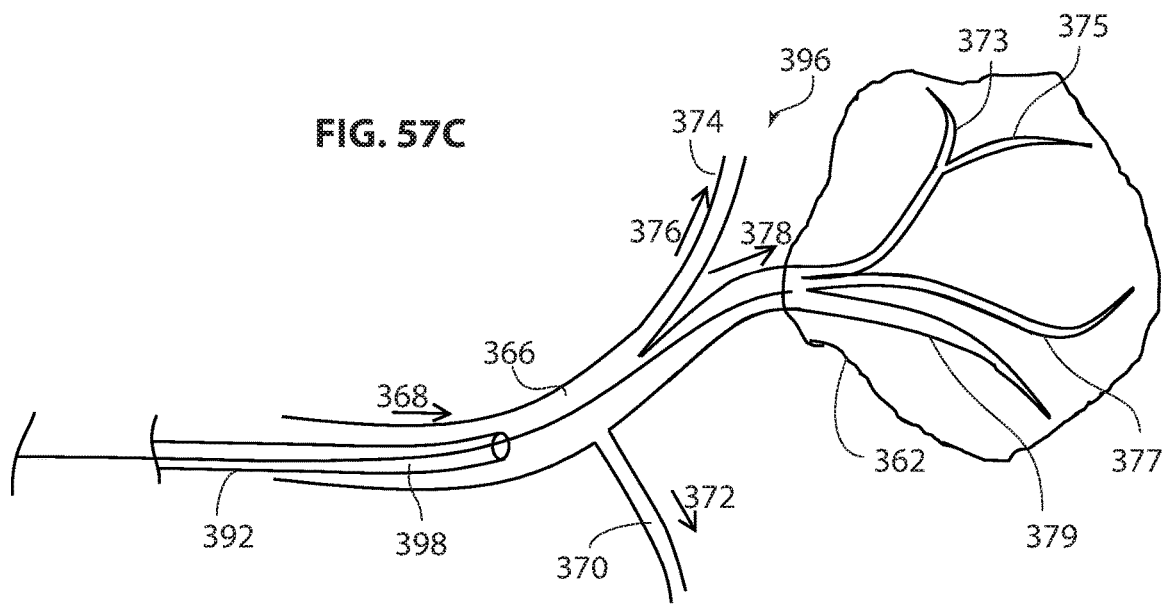

In the third step shown in FIG. 57C, guidewire 382 is optionally removed and replaced with a smaller diameter guidewire 398 that can fit in the central lumen of a microcatheter. Guidewire 398 typically has a diameter of 0.2 mm to 0.75 mm, more typically in the range of 0.25 mm to 0.6 mm.

Figure 57D:
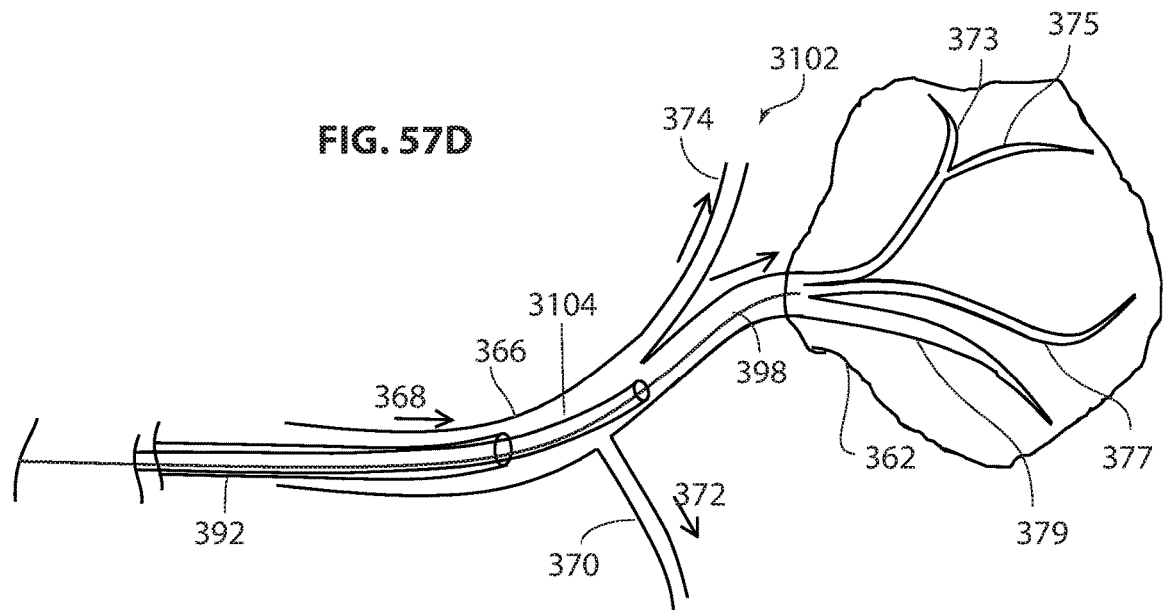

The fourth step of the procedure, microcatheter 3104 is advanced over guidewire 398 to a position beyond the distal end of guide catheter 392 and into the vasculature within or in the vicinity of the tumor as shown in anatomical structure 3102 of FIG. 57D. Microcatheter 3104 is advanced as close as is practical to the tumor and, if the anatomy allows, into the vasculature of the tumor as in superselective embolization. Microcatheter 3104 typically has a diameter of 0.75 mm to 1.5 mm, more typically at about 1 mm and a total length of 50 cm to 200 cm, more typically from 75 cm to 150 cm. The central lumen microcatheter 3104 is optimized to have an inner diameter as large as possible; however it is usually in the range of about 0.5 mm.

Figure 57E:
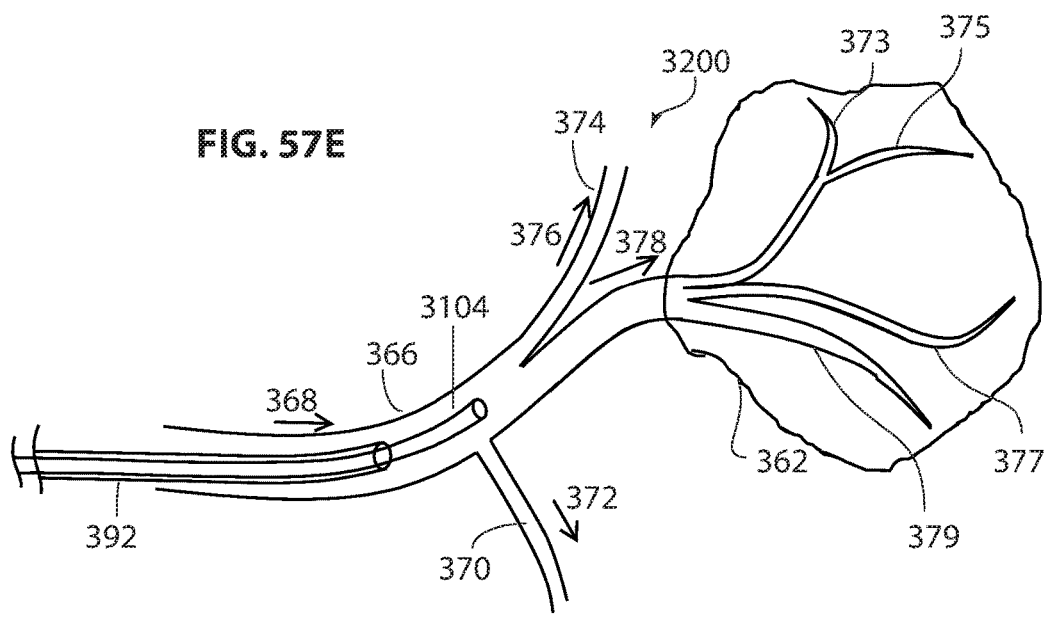

In a fifth step, guidewire 398 is removed from microcatheter 3104 as illustrated in anatomical structure 3200 of FIG. 57E. Removal of guidewire 398 allows the central lumen of microcatheter 3104 to be used to inject drug and/or embolic materials into the target site within the right hepatic artery and tumor. Blood continues to flow around guide catheter 392 and microcatheter 3104 and into capillaries 373, 375, 377, and 379 of tumor 362, gastroduodenal branch 370 and hepatoenteric branch 374 according to the normal flow pattern shown by arrows 368, 372, 376, and 378.

In a sixth step illustrated in anatomical structure 3208 of FIG. 57F, drug and or embolization agents are injected using a syringe or other means from the proximal end of microcatheter 3104 through guidewire/injection port 354 of hub 52 (FIG. 55), longitudinally through guidewire injection lumen 334 (FIG. 54), and out the distal end of catheter extension 307. In this instance, embolic particles 3210 are carried by normal blood flow into distal right hepatic artery 3214, tumor capillaries 373, 375, 377 and 379, as illustrated by flow arrow 3212, and into hepatoenteric artery 374 in the direction indicated by flow arrow 376. Drug and/or embolization agents that travel through gastroenteric branch artery 374 or any other arterial branch distal to the distal tip of microcatheter 3104, by normal forward flow, are deposited at non-target sites, including parts of the liver and intestine. This anterograde (to the catheter tip) bypass into distal hepatoenteric arteries can cause serious complications including damage or death to sections of the liver or intestine, gastric ulcers or even the death of the patient. Further, drug and/or embolic agents that travel to non-target sites, fail to enter the tumor; this resulting in a lower than optimal dose to be delivered to the tumor and a lower efficacy than desired. However, to avoid the aforementioned serious complications, physicians often under-embolize the tumor vasculature.

Referring to FIG. 57G, as forward flow mediated embolization progresses, the distal ends of capillaries 373, 375, 377 and 379 fill with particles 3210 and become embolized. This process dramatically slows the blood flow moving through the tumor and causes a sharp rise in pressure within the tumor vasculature and concomitant retrograde deflection of the high volume blood flow from the hepatic artery. Further, backpressure develops in the distal hepatic artery 3214, resulting in particles to flow in a retrograde direction as in flow direction arrow 3234. This can result in: (1) increased anterograde bypass into hepatoenteric branch 374, reflux over the catheter and into gastrodudenal artery 370 and (3) a signal to the physician that particle injection should stop, even though the tumor is only partially embolized. In this instance, it is possible that larger capillaries become embolized first, due to a larger blood flow while smaller capillaries remain un-embolized. The rapid rise in pressure is in part caused by distal capillary embolization and in part caused by the high volume blood flow from the hepatic artery. Given that embolization is the desired endpoint, it appears that slowing the forward flow of blood from the hepatic artery would allow the tumor to accept the blood and drug and/or embolic agent flow for a longer period of time and allow more embolization to occur and an improved distribution of particles in the tumor vasculature.

Figure 57H:
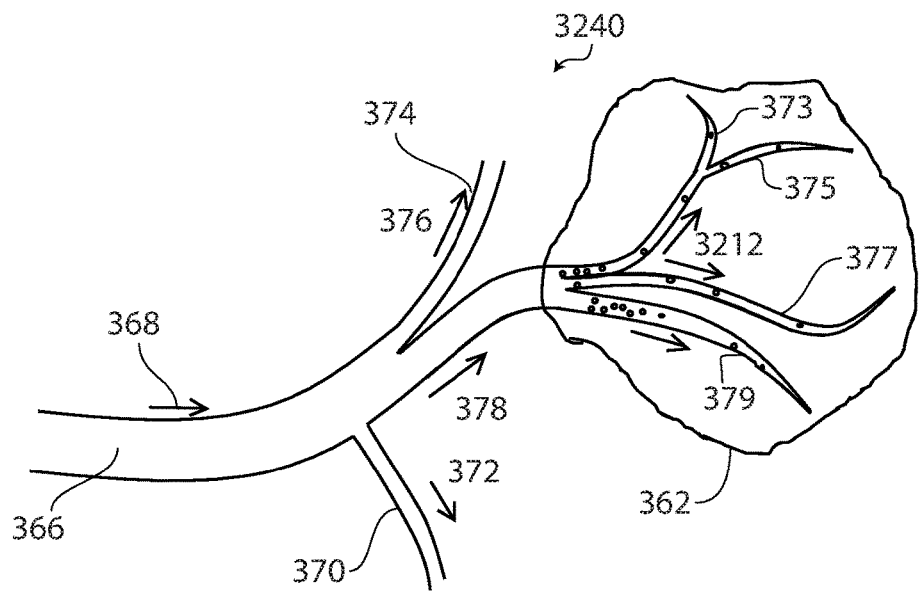

Referring to FIG. 57H, injection of drug and/or embolic agents is complete, microcatheter 3104 and guide catheter 392 are removed and the final embolization distribution in tumor capillaries 373, 375, 377 and 379 is shown where, in this example, lager capillary 379 is embolized to the greatest extent, smaller capillary 377 is embolized to a lesser extent and small capillary 373 remains un-embolized.

Referring to FIG. 58, a method of tumor embolization, according to the device of the present disclosure is shown. Steps 1 through step 5, shown in FIGS. 57A through 57E, are the same for both a standard catheter as shown in FIG. 57 and the device of the present disclosure and are not further illustrated.

Figure 58A:
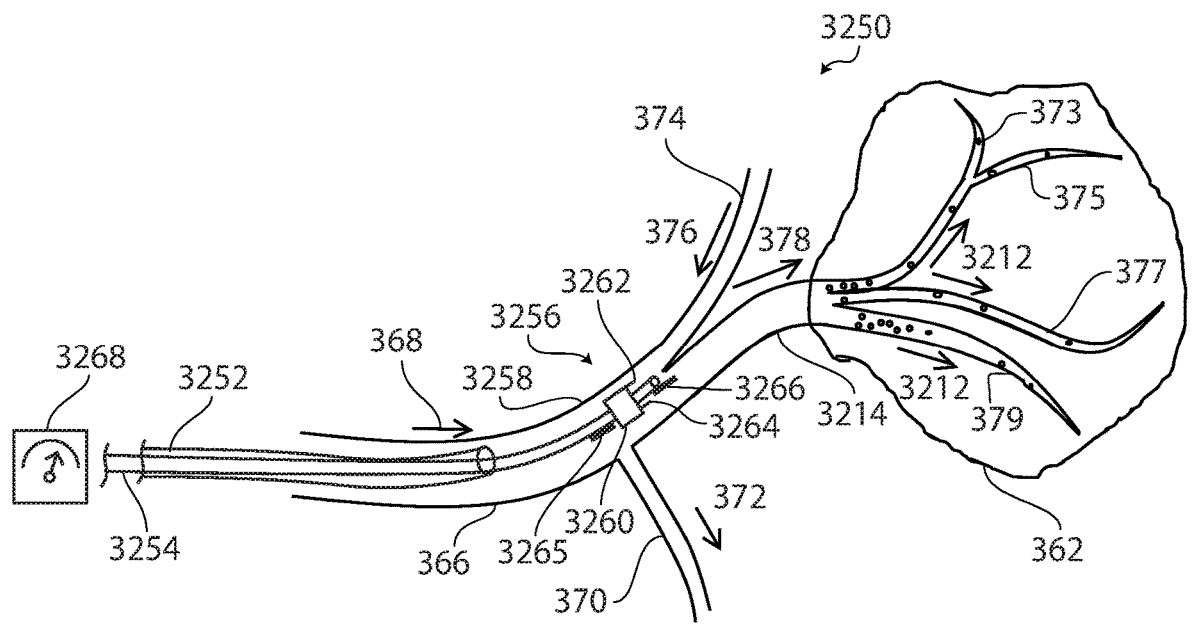
FIGS. 58A, 58B, 58C, 58D and 58E illustrate a tumor embolization method for the catheter of the present disclosure.

Referring to FIG. 58A, the device of the present disclosure is positioned in the distal right hepatic artery 3214, with partial occlusion balloon 3256 in its radially expanded configuration comprising channels 3258 and 3260, and one-way valves 3262 and 3264 that are in the open position. FIG. 58A shows two channels, however, one, two, three or any number of channels can be used. With or without valves. The maximum channel size is limited by balloon diameter, but can be as small as is practical. Valves 3262 and 3264 can be flap, duck bill, diaphragm, or any type of valve provided that it permits flow only in one direction. Optional pressure sensors 3266, which provides real time pressure measurement in the vascular space distal to partial occlusion balloon 3256 and pressure sensor 3265 which provides real time pressure monitoring in the vascular space proximal to the partial occlusion balloon 3256 are shown. Pressure sensor 3266 which measures pressure in the distal vascular space can be used to signal a procedural endpoint based on a predetermined or non-predetermined pressure reading. This will, for the first time, allow a quantitative and definitive pressure mediated endpoint rather than the present subjective flow mediated endpoint and will enable the procedure to be reproducible and able to be standardized allowing center to center and physician to physician consistency. This is possible only because the vascular space distal to the partial occlusion balloon 3256 is isolated from the vascular space proximal to partial occlusion balloon 3256, thereby allowing that the arterial pressure in the distal space to be closely related to the intra-tumor arterial blood pressure. Blood flow direction through hepatic artery 368, distal hepatic artery 3214 and proximal artery 370 are normal as seen in flow direction arrows 368, 372 and 378 as is the blood flow in tumor capillaries 373, 375, 377 and 379 and illustrated by flow direction arrows 3212. However, partial occlusion balloon 3256 causes a significant reduction in blood flow in distal right hepatic artery 214 and in tumor capillaries 373, 375, 377 and 379. Blood flow can be regulated by the partial occlusion balloon of the present disclosure such that total flow can range from near 100% (unconcluded flow) to near 0% as in full occlusion. Of most interest is partial occlusion that results in 1% to 25% flow as compared to the un-occluded artery. Therefore, channels 3258 and 3220 allow only a fraction of normal blood flow to pass distally. Blood pressure distal to partial occlusion balloon 3256 is also dramatically reduced by anywhere from about 5 mmHg reduction to 100 mmHg reduction, depending on the nature of the occlusion. This pressure drop causes branch artery 374 to reverse direction as seen by flow direction arrow 376 and now flow toward the distal main artery 3214 and tumor capillaries 373, 374, 377 and 379. The flow reduction and pressure reduction caused by partial occlusion balloon 256 also reduces the flow and pressure within the tumor capillaries 373, 374, 377 and 379. This is of significance because it allows more drug/embolization agents to enter the tumor before backpressure causes flow stasis and retrograde flow.

Figure 58B:
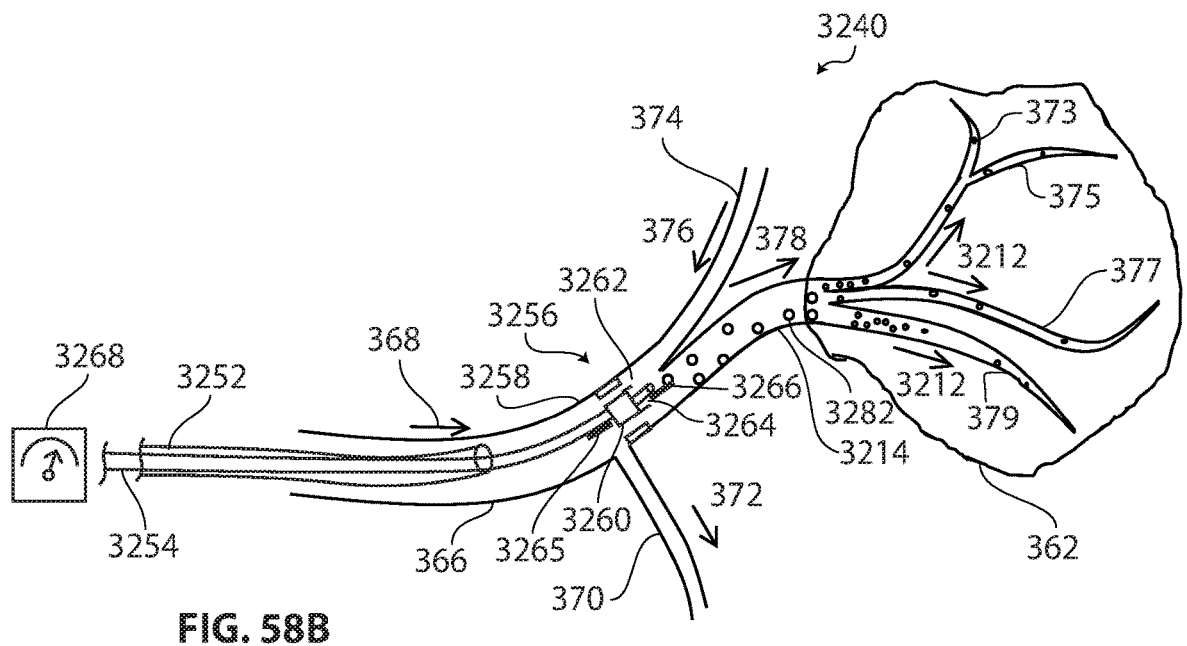

Referring now to anatomical structure 3280 of FIG. 58B, injection of drug and/or embolic agents is initiated. Blood flow from the proximal main artery 366 is attenuated as it passes through channels 3258 and 3260 and into distal main artery 3214. The anti-cancer agents are carried by the attenuated forward blood flow through distal main artery 3214 and into tumor capillaries 373, 375, 377 and 379. Valves 3262 and 3264 are in the open position as pressure in the distal vascular space is lower than the blood pressure in the vascular space proximal to partial occlusion balloon 3256. Branch artery 374 continues to flow in the reverse direction as indicated by flow direction arrow 376 since blood pressure in the distal right hepatic artery is lower than that of the arterial network connected to the distal end of branch artery 374. In this instance, anterograde drug/embolic agents are prevented from flowing into branch artery 374 and anterograde bypass and non-target delivery does not occur. Optional pressure sensors 3266 and 3265 or pressure measurement through guidewire/injection lumen 334 of catheter 6 (FIG. 54A) can be used to monitor real-time pressure.

Figure 58C:
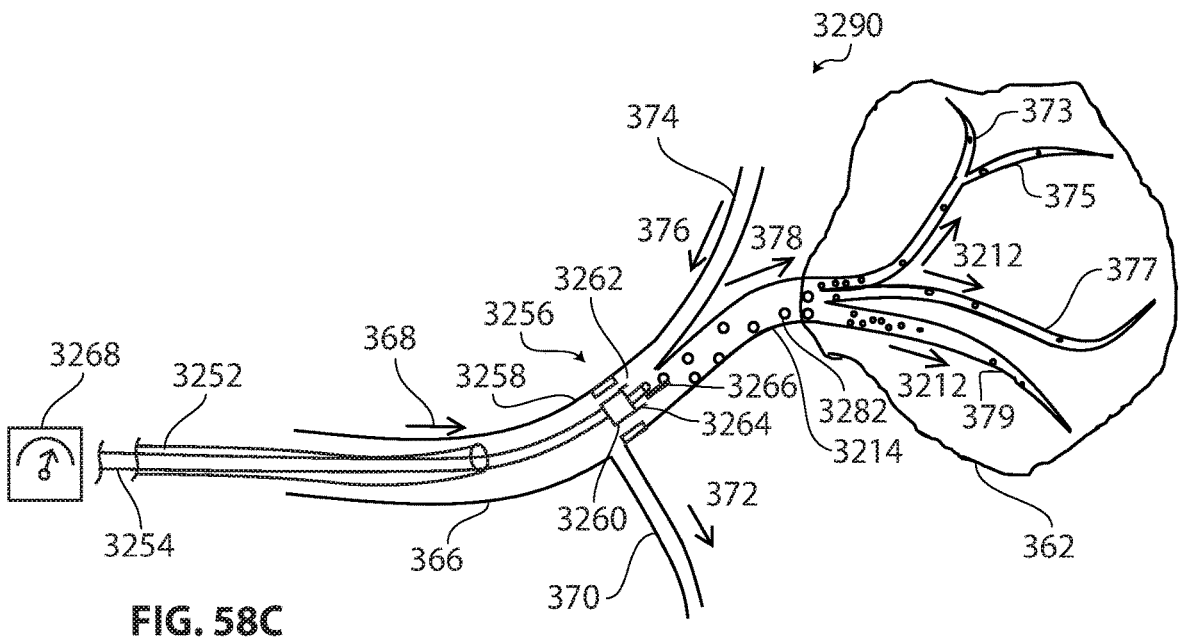
Figure 58D:
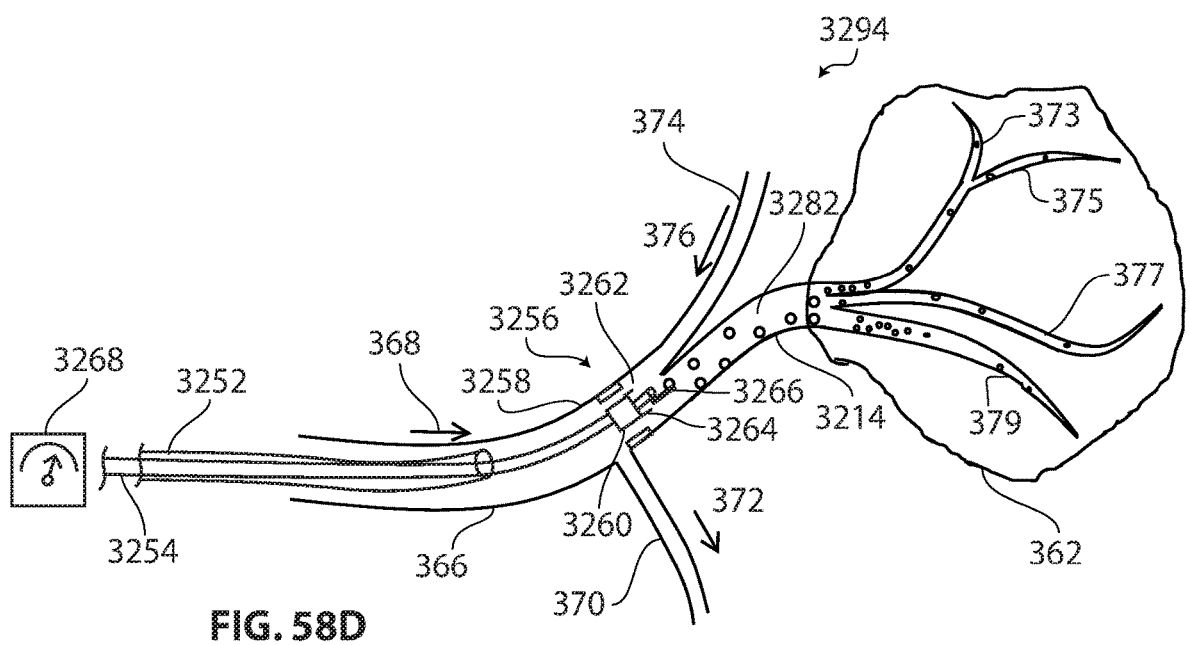

Referring to FIG. 58C, and looking at anatomical structure 3290, a slower rate of blood flow and lower pressure through distal hepatic artery 3214 allows tumor capillaries 373, 375, 377 and 379 to fill at a slower pace and to a greater distribution than in the current method of full unregulated forward flow. At some point, however, the embolization of tumor capillaries will cause retrograde deflection of blood and anti-tumor agents and a pressure build up in distal hepatic artery 3214 as in FIG. 58D. At this point, the increased pressure in distal right hepatic artery 3214 causes valves 3262 and 3264 to close, preventing retrograde flow and non-target embolization through branch artery 370 or any other arteries proximal to partial occlusion balloon 3256. This retrograde deflection and pressure build up will progress at a slower rate as compared to the current standard method of FIG. 57. The slower buildup of pressure and retrograde flow allows a larger time window for the physician to terminate the procedure. If pressure monitoring is done, a defined pressure can be used to terminate the procedure. If the back pressure in distal hepatic artery 3214 exceeds about systolic pressure, branch artery 374 will again follow in the normal flow pattern as illustrated in the flow direction arrow 376 of FIG. 56. This situation will allow anterograde drug and/or embolic agents to flow in branch artery 374 and to non-target sites. However, visual observation of contrast movement in branch artery 374 or a defined pressure measurement at or below the flow reversal pressure of branch artery 374 can be used as a procedural endpoint signal.

Figure 58E:
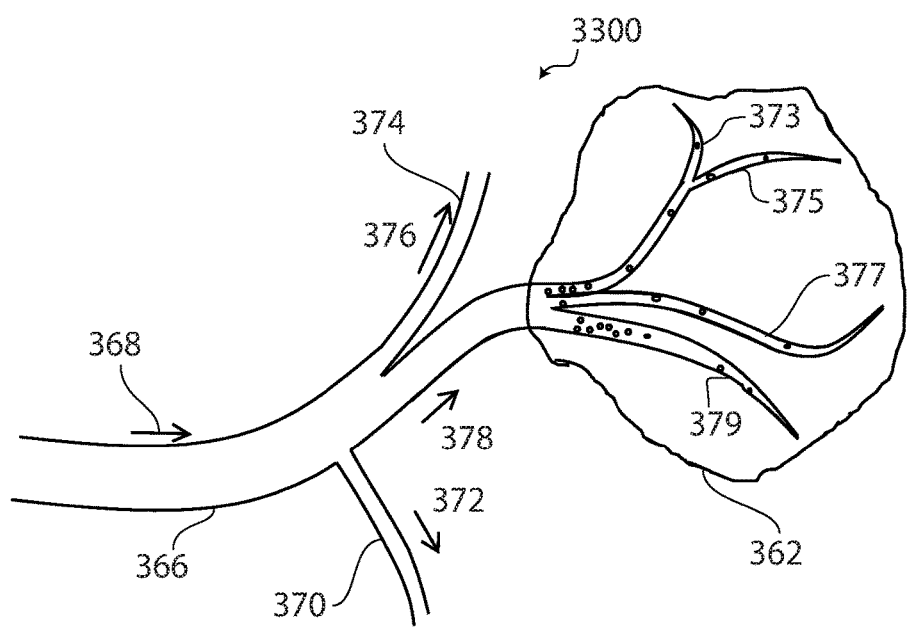
Figure 59A:
FIGS. 59A, 59B, 59C and 59D illustrate fabrication steps of the distal end of an occlusion catheter according to aspects of the present disclosure.
Figure 59B:
Figure 59C:
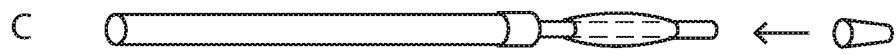
Figure 59D:
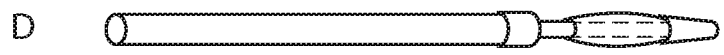

Referring now to anatomical structure 3300 of FIG. 58E, the procedure is complete and catheter 3254, of the present disclosure, and guide catheter 3252 are removed. The distribution and filling of tumor capillaries 373, 375, 377 and 379, using the device of the present disclosure, are improved as compared to the distribution and filling associated with the current microcatheter 3104 of FIG. 57H.

In some embodiments, a pressure feedback loop is implemented to control the rate of fluid introduction (e.g. the rate of embolic bead injection). In such embodiments, a blood pressure sensor may be located at the distal tip of the catheter to monitor the pressure of the vasculature distal to the occlusion or partial occlusion structure. In some embodiments, a predetermined pressure set point may be used. The set point may be an absolute pressure, or a percentage of systolic pressure (such as about 100% of systolic pressure). Such systems can be programmed to maintain the distal vasculature at or below the set point by automatically controlling the infusion rate (e.g. the rate or pressure of an injection pump.) By ensuring that the pressure of the distal vasculature does not exceed systolic pressure, retrograde and/or other undesirable blood flows can be prevented.

In some embodiments, a rate of pressure change can be used instead of or in addition to a preset pressure in the pressure feedback loop. For example, if the distal vasculature pressure begins to rise faster than a predetermined rate, the rate of embolic substance injection can be slowed, temporarily stopped, or a procedural endpoint may be signaled. The endpoint signal may be an audible, visual, tactile or other signal to persons involved in the procedure, and/or may be a signal that automatically shuts off or changes the state of medical equipment used in the procedure.

FIGS. 59A-59D show the fabrication steps of the distal end of an occlusion catheter 400 according to aspects of the present disclosure.

Figure 60:
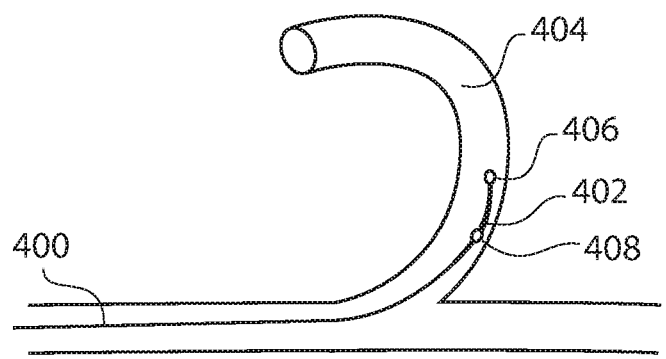
FIG. 60 illustrates the completed distal end of the occlusion catheter of FIGS. 59A-59D being introduced into small branches of a vascular system.

FIG. 60 shows the completed distal end 402 of the occlusion catheter 400 of FIGS. 59A-59D being introduced into small branches of a vascular system 404. The two enlarged contact points 406 and 408 of this design allow the catheter 400 to be navigated into smaller vasculature than can be navigated by conventional catheter tips.

Figure 61A:
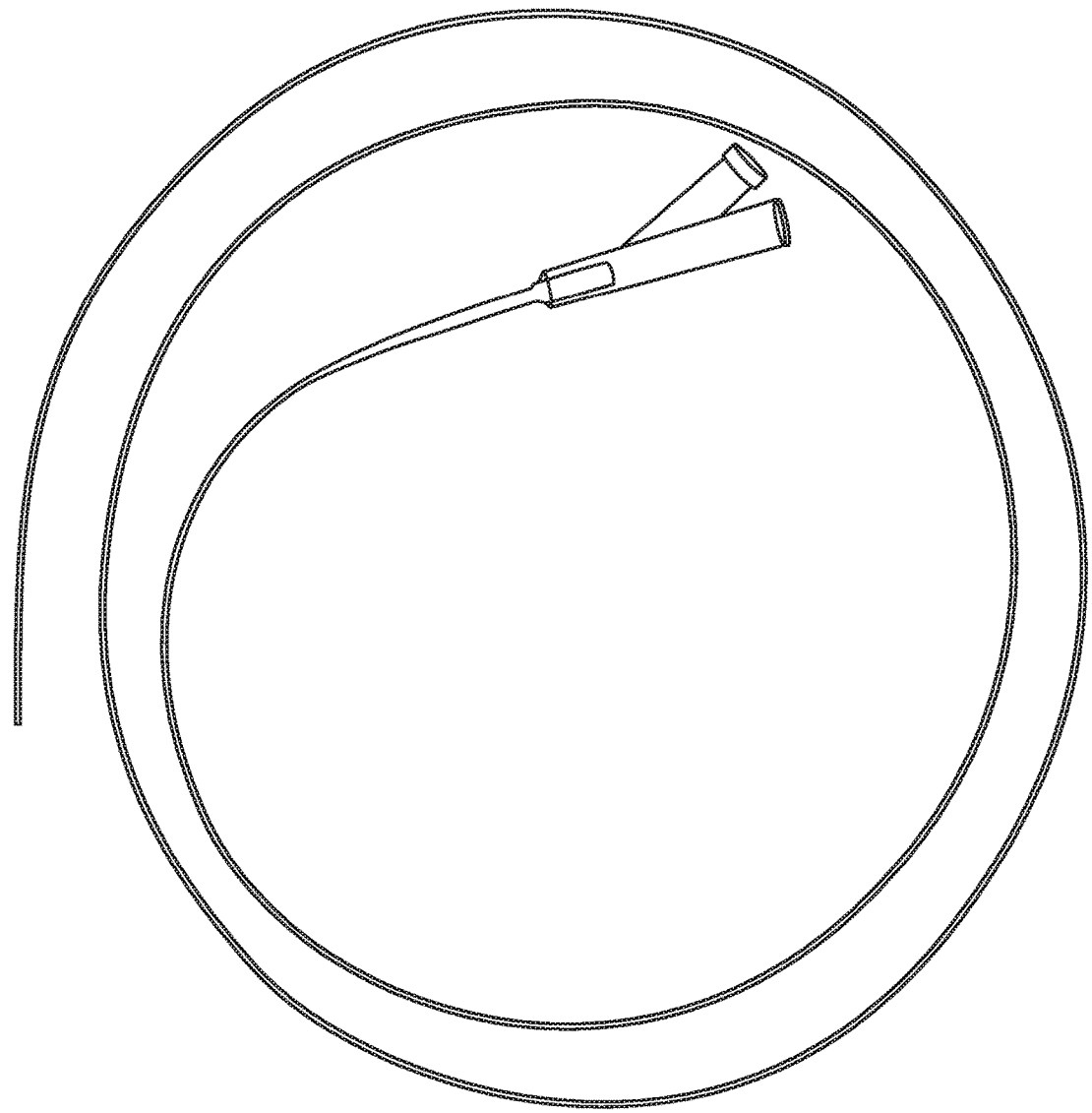
FIG. 61A shows an entire occlusion catheter constructed according to principles of the present disclosure.
Figure 61B:
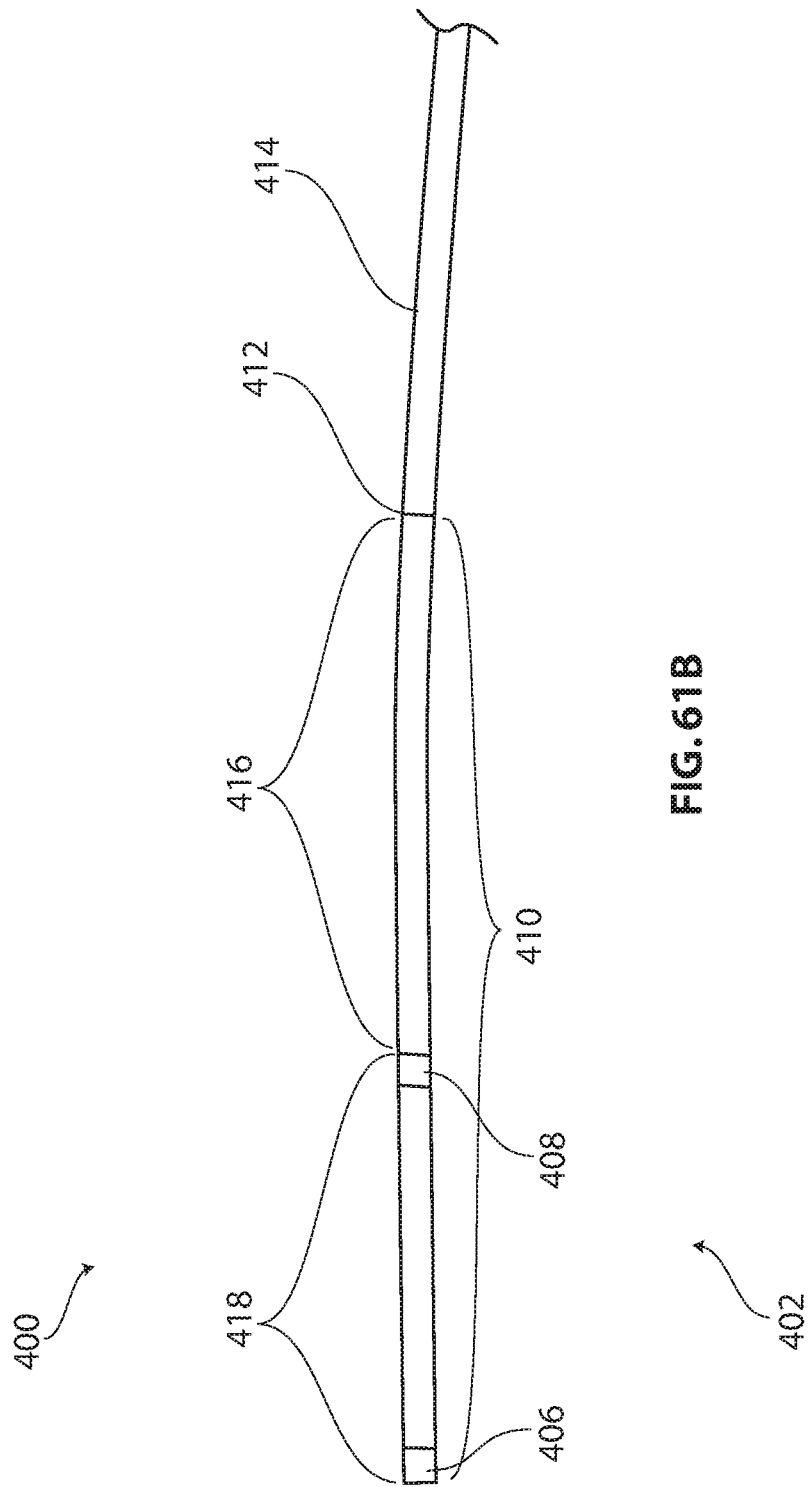
FIG. 61B shows details of construction features on the distal end of the occlusion catheter of FIG. 61A.

FIG. 61A shows an entire occlusion catheter constructed according to principles of the present disclosure. FIG. 61B shows details of construction features on the distal end 402 of the occlusion catheter 400 of FIG. 61A. These details include a catheter extension 410 attached to the distal end 412 of the catheter body 414, which includes a balloon pocket section 416 and a distal tip section 418. A nose cone radio-opaque marker 408 is located at the proximal end of the distal tip section 418, and a radio-opaque marker 406 is located at the distal end of the distal tip section 418. As previously mentioned, both markers 406 and 408 have enlarged diameters as compared with the diameter of the adjacent distal tip section 418.

It is important to note that the device of the present disclosure regulates flow and pressure in the arterial space distal to the partial occlusion balloon, significantly reduces flow rate and pressure in tumor capillaries and causes flow reversal of distal branch arteries. The aforementioned device and method thereby enable substantial elimination of retrograde and anterograde bypass to non-target sites and a more complete filling of the tumor vasculature with drug and or embolic agents and should improve efficacy and reduce complications over standard devices and methods.

What is claimed is:

1. A method of embolizing a tumor, the method comprising:
    advancing a distal end of a device including a catheter body and an occlusion structure to a target tumor site within a blood vessel of a body, wherein the device comprises a catheter extension that extends axially beyond a distal end of the catheter body, wherein the catheter extension comprises an outer diameter less than an outer diameter of the catheter body, wherein a nose piece is adapted to the catheter extension, and wherein the occlusion structure comprises an inflatable balloon disposed on the catheter extension in a pocket between the distal end of the catheter body and a proximal end of the nose piece such that the inflatable balloon has an outer diameter approximately equal to the outer diameter of the catheter body when the inflatable balloon in disposed in the pocket in a deflated state;

activating the occlusion structure within the blood vessel;

monitoring a real time pressure measurement in the vascular space distal to the activated occlusion structure;

waiting for a pressure drop in a vascular space distal to the activated occlusion structure and for the pressure drop to cause a blood flow reversal in branch vessels antegrade to the occlusion;

injecting an embolic substance from the distal end of the delivery device to permit the reversed blood flow to carry the embolic substance into the vasculature of the target tumor; and withdrawing the device from the body.

2. The method of claim 1, further comprising a step of signaling a procedural endpoint based on the monitoring of the pressure measurement.

3. The method of claim 2, wherein the signaling of the procedural endpoint occurs when a predetermined pressure is reached in the vascular space distal to the activated occlusion structure.

4. The method of claim 3, wherein the predetermined pressure is a predetermined percentage of an un-occluded systolic pressure.

5. The method of claim 4, wherein the predetermined percentage is in the range of about 50% to 100%.

6. The method of claim 1, wherein the occlusion structure comprises an inflatable balloon.

7. The method of claim 6 wherein the balloon is provided with a plurality of channels that extend from a proximal end to a distal end of the balloon, the channels configured to provide fluid communication between a proximal surface of the balloon and a distal surface of the balloon.

8. The method of claim 7, wherein the channels are offset from a central longitudinal axis of the balloon and are equally spaced about the circumference of the catheter to provide symmetrical blood bypass through the balloon.

9. The method of claim 7, wherein the balloon comprises valves configured to affect fluid flow through the channels.

* * * * *